(12) United States Patent
Guevel et al.

(10) Patent No.: US 7,838,533 B2
(45) Date of Patent: Nov. 23, 2010

(54) AZAINDOLE INHIBITORS OF MTP AND APOB

(75) Inventors: Alyx Caroline Guevel, Villeurbanne (FR); Catherine Vidal, Lyons (FR); Bruno Roux, Lyons (FR); Olivier Chevreuil, Condeissiat (FR)

(73) Assignee: Merck Patent GmbH, Darmstadt (DE)

( * ) Notice: Subject to any disclaimer, the term of this patent is extended or adjusted under 35 U.S.C. 154(b) by 971 days.

(21) Appl. No.: 11/658,596

(22) PCT Filed: Jun. 28, 2005

(86) PCT No.: PCT/EP2005/006930

§ 371 (c)(1),
(2), (4) Date: Jan. 26, 2007

(87) PCT Pub. No.: WO2006/010423

PCT Pub. Date: Feb. 2, 2006

(65) Prior Publication Data

US 2009/0036481 A1    Feb. 5, 2009

(30) Foreign Application Priority Data

Jul. 27, 2004    (FR) ................... 04 08302

(51) Int. Cl.
  *C07D 471/02*    (2006.01)
  *A61K 31/437*    (2006.01)

(52) U.S. Cl. ...................... 514/300; 546/113

(58) Field of Classification Search ................ 514/300; 546/113
See application file for complete search history.

(56) References Cited

U.S. PATENT DOCUMENTS

| | | | |
|---|---|---|---|
| 3,362,956 A * | 1/1968 | Archer | 544/363 |
| 3,511,841 A * | 5/1970 | Archer | 544/362 |
| 4,939,159 A | 7/1990 | Anderson et al. | |
| 5,684,014 A | 11/1997 | Mueler et al. | |
| 6,979,692 B2 | 12/2005 | Bertinato et al. | |
| 2005/0239780 A1 | 10/2005 | Suga | |
| 2006/0100230 A1 | 5/2006 | Bischoff et al. | |

FOREIGN PATENT DOCUMENTS

| | | |
|---|---|---|
| EP | 1 367 058 A | 12/2003 |
| WO | WO 03/002533 A | 1/2003 |
| WO | WO 2004/005253 A | 1/2004 |

* cited by examiner

*Primary Examiner*—D. Margaret Seaman
*Assistant Examiner*—Niloofar Rahmani
(74) *Attorney, Agent, or Firm*—Millen, White, Zelano & Branigan, P.C.

(57) ABSTRACT

The present invention relates to 7-azaindole-based compounds, to processes for the preparation thereof, to pharmaceutical compositions comprising them, and to the use thereof in the preparation of medicaments that are useful as inhibitors of MTP and of ApoB secretion.

15 Claims, 4 Drawing Sheets

AZAINDOLE INHIBITORS OF MTP AND APOB

The present invention relates to 7-azaindole-based compounds, to processes for the preparation thereof, to pharmaceutical compositions comprising them, and to the use thereof in the preparation of medicaments that are useful as inhibitors of MTP and of ApoB secretion.

PRIOR ART

MTP (microsomal triglyceride transfer protein) is a transfer protein located in the reticulum of hepatocytes and enterocytes, which catalyses the assembly of biomolecules that transport triglycerides, the ApoB lipoproteins.

The term ApoB more particularly denotes apoprotein B 48' of the intestine and apoprotein B 100 of the liver.

Mutations in MTP or in the B apoproteins are reflected in man by very low levels or even an absence of ApoB lipoproteins. The lipoproteins containing ApoB (chylomicrons, very low density lipoproteins) and their metabolic residues (chylomicron remnants, low density lipoproteins) are recognised as being a major risk factor in the development of atherosclerosis, a major cause of death in industrialised countries. It is observed that, in individuals who are heterozygous for these mutations, levels reduced on average by a half are associated with a low cardiovascular risk (C. J. Glueck, P. S. Gartside, M. J. Mellies, P. M. Steiner, *Trans. Assoc. Am. Physicians*, 90, 184 (1977)). This suggests that modulation of the secretions of triglyceride-rich lipoproteins by means of MTP antagonists and/or of ApoB secretion might be useful in the treatment of atherosclerosis and more broadly of pathologies characterised by an increase in ApoB lipoproteins.

Molecules that inhibit MTP and/or the secretion of ApoB might thus be useful for the treatment of hypertriglyceridaemia, hypercholesterolaemia and diabetes-related dyslipidaemia, and also for the prevention of and treating obesity.

Anti-atherosclerosis compounds are described especially in document. EP 802 188 in the name of Bayer, but do not, however, have a chemical structure similar to that of the compounds of the present invention.

Document U.S. Pat. No. 6,335,342 in the name of Pharmacia & Upjohn describes 7-azaindole-based compounds. These derivatives have a chemical structure different from that of the compounds of the invention and are moreover antitumoral.

The inventors have now discovered a family of compounds, whose structure is different from that of the compounds described in the prior documents mentioned above, which afford particularly effective inhibition of MTP and also excellent inhibition of apoprotein B (ApoB) secretion.

SUMMARY OF THE INVENTION

The present invention relates to 7-azaindole-based compounds of the general formula (I), to acidic precursors thereof, and to processes for the preparation thereof.

The present invention is also directed towards pharmaceutical compositions comprising an effective amount of at least one of these compounds, in combination with a pharmaceutically acceptable vehicle.

The present invention also relates to the use thereof or to the use of the said compositions in the preparation of medicaments that are useful as inhibitors of MTP and of ApoB secretion, which are more especially useful in the treatment of the following diseases: hypercholesterolaemia, hypertriglyceridaemia, hyperlipidaemia, pancreatitis, hyperglycaemia, obesity, atherosclerosis and diabetes-related dyslipidaemia.

The present invention will now be described with the aid of illustrative examples with reference to tables and attached figures in which.

DETAILED DESCRIPTION OF THE INVENTION

Figure 1:
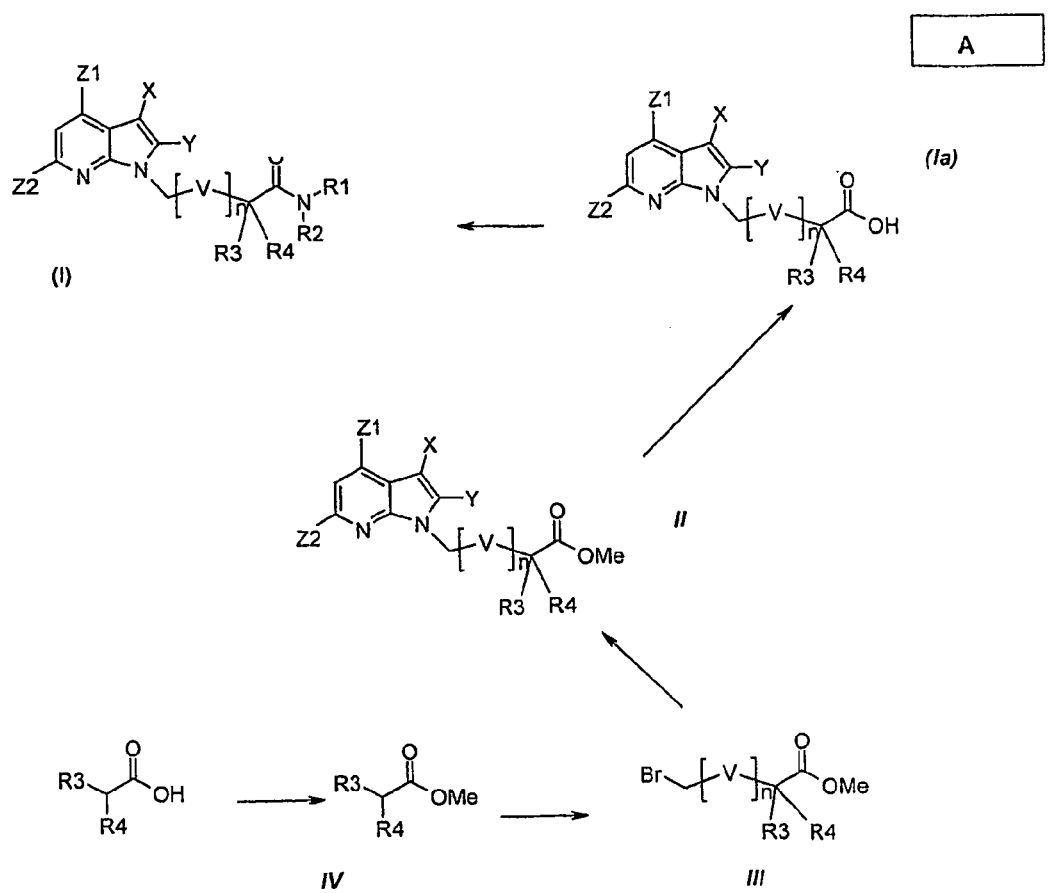
FIG. 1 is a general scheme of synthetic route A for the compounds of the invention.
Figure 2:
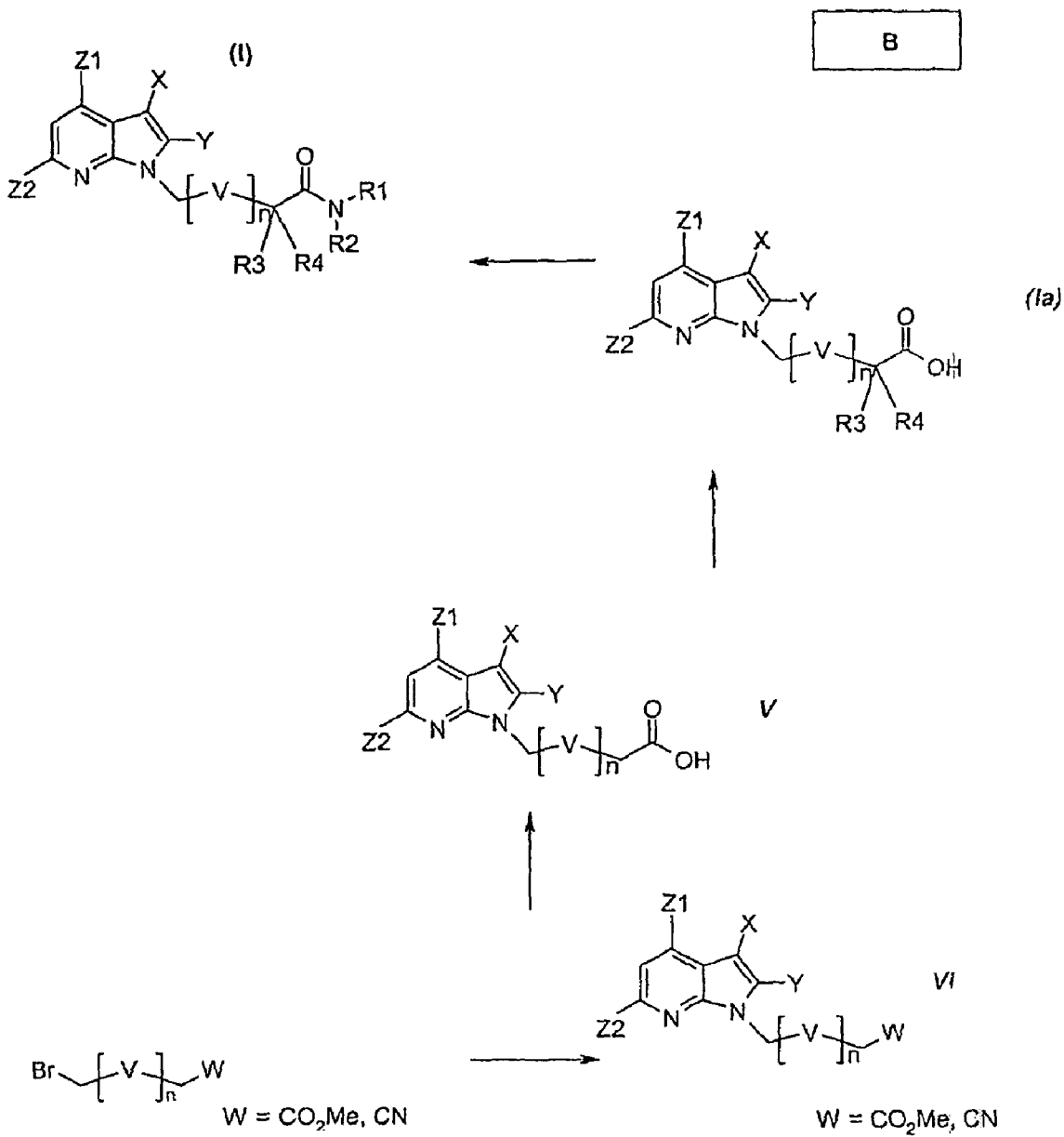
FIG. 2 is a scheme of synthetic route B for the compounds of the invention.
Figure 3:
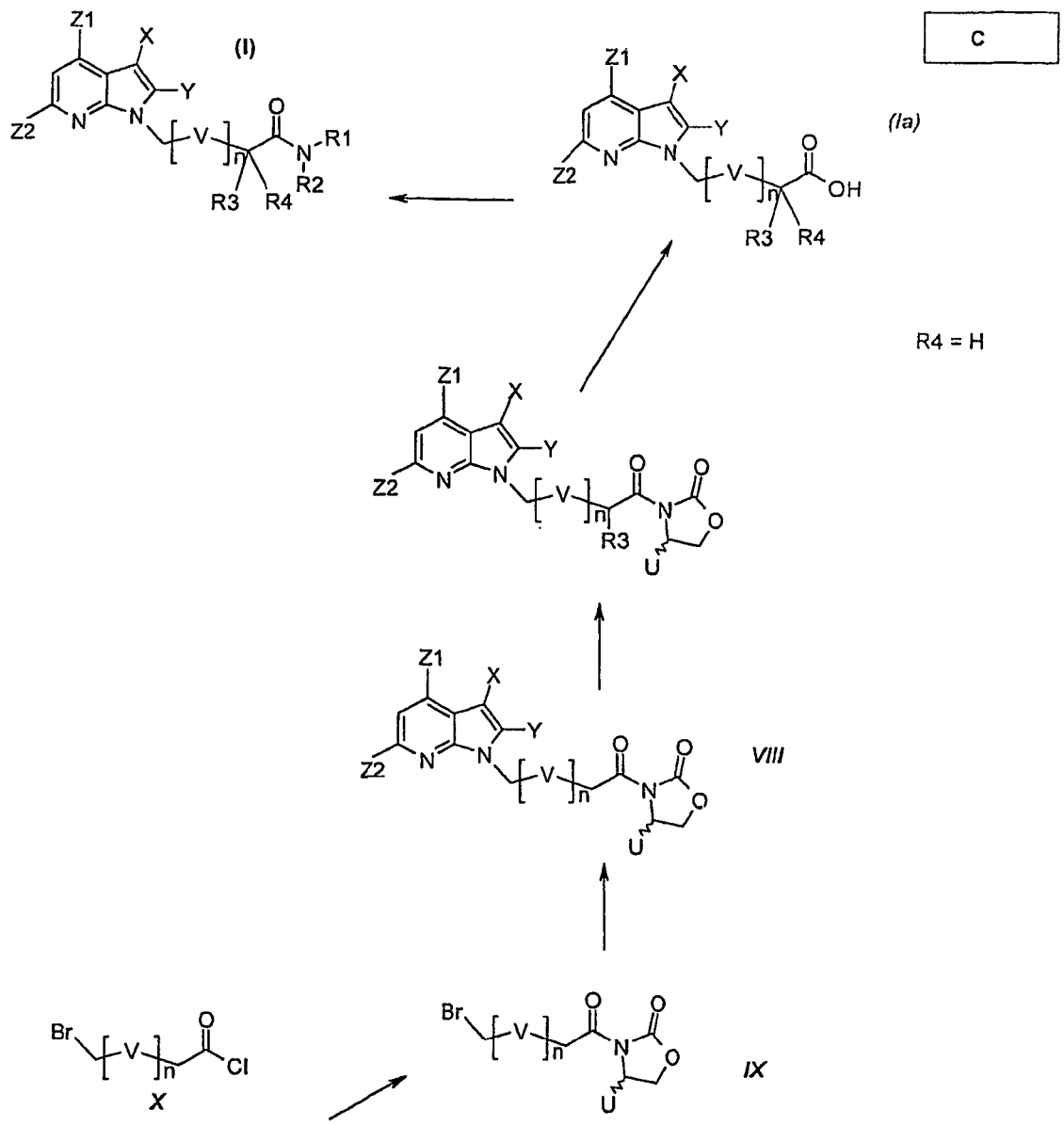
FIG. 3 is a scheme of synthetic route C for the compounds of the invention.
Figure 4:
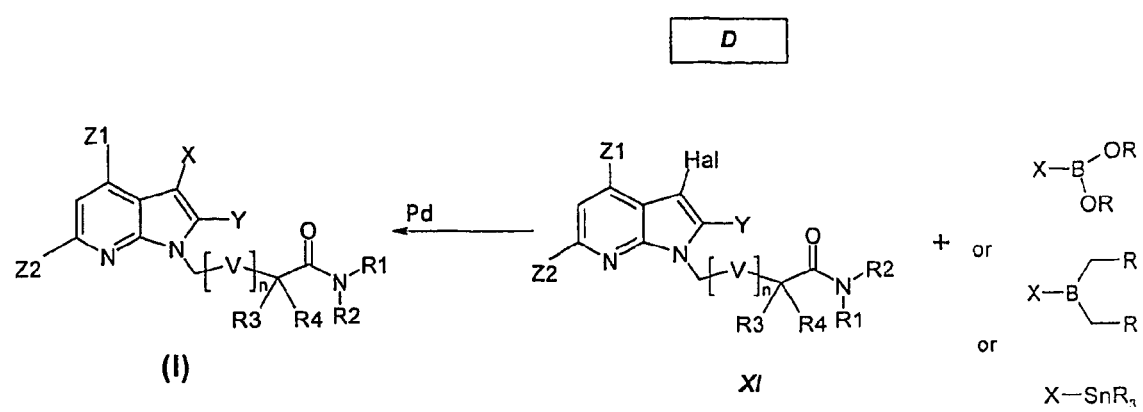
FIG. 4 is a scheme of synthetic route D for the compounds of the invention.

More particularly, the present invention relates to the 7-azaindole-based compounds of the formula (I) below:

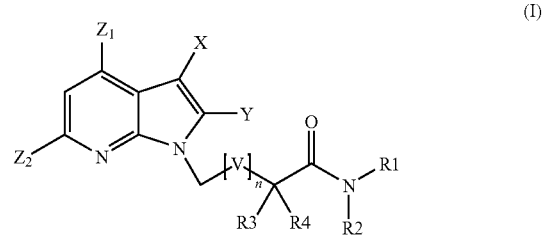

(I)

and also the salts, N-oxides, stereoisomers and mixtures of stereoisomers thereof, in which V is a linear or branched saturated hydrocarbon-based chain, n denotes the number of —$CH_2$— radicals, the said chain being optionally interrupted by one or more hetero atoms, especially oxygen;

Z1 represents a hydrogen atom or a radical —NR11R12 in which R11 and R12 independently represent a hydrogen atom or an alkyl, aryl or aralkyl radical; preferably, —NR11R12 represents a radical —N(alkyl)$_2$, such as —NMe$_2$, or a radical —N(alkyl)(aryl), such as —N(Me)(phenyl);

Z2 represents a hydrogen atom or a radical —Oalkyl, such as —OMe;

X and Y are, independently of each other:

a hydrogen atom, optionally substituted (C1-C6)alkyl, especially methyl, isopropyl or n-hexyl, optionally substituted (C1-C6)alkenyl, especially trans-1-hexen-1-yl or trans-2-(4-fluorophenyl)vinyl, a halogen atom, in particular bromine, nitrilo or nitroso, trans-beta-styrenyl, 4-(tert-butyldimethylsilyloxy), optionally substituted aryl, in particular naphthyl, preferably phenyl or phenyl substituted by at least one radical, such as methyl, hydroxyl, methoxy, ethoxy, propoxy, isopropoxy, butoxy, methoxyethoxy, phenoxy, benzyloxy, fluoro, chloro, methylthio, methylsulfonyl, ethylthio, acetyl, cyano, trifluoromethyl, trifluoromethoxy, vinyl, carboxyl, nitro, 4-(N,N-dimethylamino), bromo, tert-butyl, hydroxymethyl, phenyl, ethyl, acetate, carbonate, heteroaryl, optionally substituted especially by chloro, methyl or acetyl, in particular thienyl, furanyl, benzo[b]furanyl, benzo[b]thienyl, 1H-pyrazolyl, pyridyl or thianaphthyl;

3,4-methylenedioxyphenyl;

X and Y do not together form a ring or heterocycle;

R1 and R2 are, independently of each other:

a hydrogen atom, optionally substituted (C1-C10)alkyl, in particular methyl, n-hexyl, n-heptyl, n-octyl or trans-2-phenylcyclopropyl, —CH$_2$—OH, —COO-Et, cycloalkyl, especially cyclohexyl, which is optionally substituted and/or fused, especially with a benzene nucleus;

indanyl, benzocyclopentyl, optionally substituted alkenyl, preferably allyl, or an optionally substituted acyclic terpenic radical, preferably geranyl;

optionally substituted aryl, in particular phenyl, especially phenyl para-substituted by isopropyl, OMe, COOMe, EtOCO or MeCO, or meta- and para-substituted by methyl; or alternatively (diEtO)PO—CH$_2$-phenyl, optionally substituted heteroaryl, especially imidazolyl, in particular: 3-(1-benzyl)imidazolyl, 5-(2-methyl-4-methoxyphenyl)imidazolyl; thiazolyl, pyridyl, piperidyl, in particular: 2-aminopiperidyl, 4-(1-ethoxycarbonyl)piperidyl, 4-carboethoxyaminopiperidyl; pyrimidinyl; pyrrolidinyl, in particular: 2-amino-ethylpyrrolidinyl, 3-(1-benzyl)pyrrolidinyl; piperazinyl, in particular: 3-(amino-propylaminomethyl)piperazinyl; pyrazolyl, in particular: 3-(1-Me-4MeOPh)-pyrazolyl; quinolyl, optionally substituted saturated heterocycle, especially piperidino—in particular: benzylpiperidino, 6-fluoroquinolylmethylpiperidino;

or alternatively a radical of the formula —CH(R5)(R6) in which R5 is Me, OMe, COOH, COOMe, COOEt, CH$_2$OH, EtOCO Ph and in which R6 is —(CH$_2$)$_3$—CH(Me)$_2$, Ph, CH$_2$-Ph, (4')FPh, —CH(OH)-Ph, —CH$_2$-(4')OHPh, —CH$_2$COCH$_2$Ph, —CH$_2$—O-(2',6')MePh, —(CH$_2$)$_3$—CH(diMe)

or alternatively the radical —C(Me)(diCH$_2$OH)

or alternatively a radical of the formula —CH$_2$—R7 in which

R7 may be optionally substituted aryl, or optionally substituted heteroaryl and especially pyridyl.

If R7 is Ph, it may be optionally ortho-, meta- or para-substituted by alkyl, especially with Me, or CF$_3$, especially in the ortho or meta position, with OH, a halogen atom, butyl, —OMe, MeO, —CH$_2$OH, —COOH, —COOMe, —COOallyl, —CO—S-Et, —NO$_2$, —OEt, —N(alkyl)$_2$, —CONH—SO$_2$OH, —SO$_2$OH, —C(=NH)NH$_2$, —SO$_2$Me, —SO$_2$NH$_2$, especially in the para position, or alternatively phenyl para-substituted by a compound of the formula —COO—CH$_2$—R8 in which R8 is —O-Me, —O—(CH$_2$)$_2$—Si(Me)$_3$, —Si(Me)$_3$, —CCl$_3$, —CH$_2$-pyridyl, CONH$_2$, R7 also being: —CH(OH)Ph, —C(CH$_2$OH)Ph$_2$, —C(OMe)Ph$_2$, —CO—NHPh, —CONH-(2')COO-EtPh, cyclopentylidenyl-CH$_2$-Ph, cyclopentylidenyl-CH$_2$-(4'-EtOH)Ph; if R7 is heteroaryl, it may especially be pyridyl, pyrimidine, pyridine N-oxide;

or alternatively R7 is:

(2')OH naphthyl, furfuryl optionally substituted by Me, 2-(1-Et)imidazolidinyl, 2-(1-Et)pyrrolidinyl, chromanyl, triazolyl optionally substituted by —CH$_2$— (p-OMe)Ph, or alternatively R1 and R2 are also independently of each other a radical of the formula: —(CH$_2$)$_2$—R8 in which R8 is OH, —O-(4')COOMePh, —O—CO-(E)-(CH=CH)Ph, —(CH)Ph$_2$ phenyl optionally ortho-substituted by a bromine atom, or meta-substituted by OMe, or para-substituted by OH, OMe or COOMe, or meta- and para-substituted by MeO or OMe, thienyl, pyridyl, piperidino, or alternatively R1 and R2 are also independently of each other a radical of the formula: —(CH$_2$)$_3$—R9 in which R9 is —N(Et)$_2$, imidazolyl, morpholino, pyrrolidinyl, piperidino optionally: substituted by (2')Me, or alternatively R1 and R2, together with the nitrogen to which they are attached, form an optionally substituted 5- to 10-membered saturated or unsaturated heterocycle optionally comprising one or more hetero atoms chosen from N, S and O;

R3 and R4 are, independently of each other, H or alkyl, especially (C1-C6)alkyl, in particular methyl, isopropyl, 2-butyl or tert-butyl;

alkenyl, especially (C1-C6) alkenyl, in particular allyl;

(C5-C8)cycloalkyl; (C5-C8)cycloalkenyl, especially 2',3'-cyclopentenyl;

indanyl;

aryl, for example phenyl;

5- to 10-membered saturated or unsaturated heterocyclyl comprising one or more hetero atoms chosen from O, N and S;

R3 possibly being an amino, oxygen or sulfur group optionally substituted by an alkyl radical, especially (C1-C6) alkyl, especially Et, or alkenyl, especially (C1-C6)alkenyl, in particular allyl, or with a heterocycle possibly comprising one or more hetero atoms, such as O, N and S, the said heterocycle itself being optionally fused;

or alternatively R3 and R4, together with the carbon to which they are attached, form a cyclohexane optionally substituted by one or more alkyl radicals (Me) or alternatively a monospirane compound (spiro[3,4]octane) or alternatively a monospirane compound in which at least one of the constituents is a fused polycyclic system (spiro[cyclobutane-1:1'-indane]).

or alternatively R3 and R4, together with the carbon to which they are attached, form an optionally fused cyclopentylidene;

and also the salts, N-oxides, stereoisomers and mixtures of stereoisomers thereof.

Compounds that are particularly preferred are those for which:

Z1 represents a hydrogen atom;

Z2 represents a hydrogen atom;

X is phenyl or substituted phenyl, especially substituted by OH, Py(2-, 3- or 4), Br;

Y=H;

n=3 or 4;

R2 is H;

R1 is CH$_2$Ar (aryl preferably being substituted or unsubstituted phenyl), CH$_2$-heteroaryl (heteroaryl preferably being pyridyl, pyrimidine or pyridine-N-oxide);

R3 is cyclopentyl, cyclohexyl or cycloheptyl;

R4 is H.

Among the compounds that are particularly preferred are those for which the symbols X, Y, n, R2, R1, R3 and R4 have the meanings described above, and also the salts, N-oxides, stereoisomers and mixtures of stereoisomers thereof.

According to the present invention, the alkyl groups represent saturated hydrocarbon-based groups, in a straight or branched chain, of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl groups.

If they are branched or substituted by one or more alkyl groups, mention may be made especially of isopropyl, tert-butyl, 2-ethylhexyl, 2-methylbutyl, 2-methylpentyl, 1-methylpentyl and 3-methylheptyl groups.

The alkoxy groups according to the present invention are groups of the formula

—O-alkyl, the alkyl being as defined above.

Among the halogen atoms, mention is made more particularly of fluorine, chlorine, bromine and iodine atoms, preferably fluorine.

The alkenyl groups represent hydrocarbon-based groups, in a straight or linear chain, and comprise one or more ethylenic unsaturations. Among the alkenyl groups that may especially be mentioned are allyl or vinyl groups.

The alkynyl groups represent hydrocarbon-based groups, in a straight or linear chain, and comprise one or more acetylenic unsaturations. Among the alkynyl groups, mention may be made especially of acetylene.

The cycloalkyl group is a saturated or partially unsaturated, non-aromatic mono-, bi- or tricyclic hydrocarbon-based group of 3 to 10 carbon atoms, especially, such as cyclopropyl, cyclopentyl, cyclohexyl or adamantyl, and also the corresponding rings containing one or more unsaturations.

Aryl denotes a mono- or bicyclic hydrocarbon-based aromatic system of 6 to 10 carbon atoms. Among the aryl groups, mention may be made especially of the phenyl or naphthyl group.

Among the -alkylaryl groups, mention may be made especially of the benzyl or phenethyl group.

The heteroaryl groups denote mono- or bicyclic aromatic systems of 5 to 10 carbon atoms, comprising one or more hetero atoms chosen from nitrogen, oxygen and sulfur. Among the heteroaryl groups that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazoyl pyridyl, pyrimidinyl, purinyl, quinazolinyl, quinolinyl, isoquinolyl, 1,3,4-thiadiazoyl, thiazolyl, triazinyl, isothiazolyl and carbazolyl groups, and also the corresponding groups derived from their fusion or from fusion with the phenyl nucleus. The preferred heteroaryl groups comprise thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl and thiadiazolyl groups, and the groups derived from fusion with a phenyl nucleus, and more particularly quinolyl, carbazolyl and thiadiazolyl.

The heterocyclic groups denote saturated or partially unsaturated, non-aromatic mono- or bicyclic systems of 5 to 10 carbon atoms, comprising one or more hetero atoms chosen from N, O and S. Among the heterocycles, mention may be made especially of epoxyethyl, oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl tetrahydrothiopyranyl, dithianyl, thiomorpholinyl, dihydrofuranyl, 2-imidazolinyl, 2,3-pyrrolinyl, pyrazolinyl, dihydrothiophenyl, dihydropyranyl, pyranyl, tetrahydropyridyl, dihydropyridyl, tetrahydropyrimidinyl and dihydrothiopyranyl, and the corresponding groups derived from fusion with a phenyl nucleus, and more particularly morpholinyl, dioxalanyl, benzothiazolidinyl, pyrrolidinyl and benzopyrrolidinyl rings.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid, and by isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexyl sulfamates and quinateslauryl-sulfonate, and analogues. (See, for example, S. M. Berge et al. <<Pharmaceutical Salts>>, *J. Pharm. Sci,* 66: p. 1-19 (1977) which is incorporated herein by reference) The acid-addition salts can also be prepared by separately reacting the purified compound in its purified form with an organic or mineral base, and by isolating the salt thus formed. The acid-addition salts include the amine and metal salts. The suitable metal salts include the sodium, potassium, calcium, barium, zinc, magnesium and aluminium salts. The ammonium, sodium and potassium salts are preferred. The suitable mineral base-addition salts are prepared from metallic bases, which include sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include the amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

Preferred salts include the salts with acids or bases.

The acids that can be used for the formation of the salts of compounds of the formula I are mineral or organic acids. The resulting salts are, for example, the hydrochlorides, hydrobromides, sulfates, hydrogensulfates, dihydrogenphosphates, citrates, maleates, fumarates, 2-naphthalenesulfonate and para-toluenesulfonates.

The bases that can be used for the formation of salts of compounds of the formula I are organic or mineral bases. The resulting salts are, for example, the salts formed with metals and especially alkali metals, alkaline-earth metals and transition metals (such as sodium, potassium, calcium, magnesium or aluminum) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially relates to the pharmaceutically acceptable salts, but also to salts allowing a suitable separation or crystallisation of the compounds of the formula I, such as the salts obtained with chiral amines.

The invention is also directed towards the stereoisomers of the compounds of the formula I, and also to mixtures of stereoisomers in all proportions.

It will be appreciated that the compounds that are useful according to the present invention may contain asymmetric centres. These asymmetric centres may be, independently, of R or S configuration. It will be apparent to a person skilled in the art that certain compounds that are useful according to the invention may also have geometrical isomerism. It should be understood that the present invention includes individual geometrical isomers and stereoisomers and mixtures thereof, including racemic mixtures, of compounds of the formula (I) above. Isomers of this type can be separated from their mixtures by application or adaptation of known processes, for example chromatography techniques or recrystallisation techniques, or they are prepared separately from suitable isomers of their intermediates.

The synthetic routes for certain compounds of the general formula (I) of the invention will be specified in the "Examples" section hereinbelow and also in the appendices to the present description.

Certain abbreviations that are commonly accepted by those skilled in the art (Me=methyl; Et=ethyl, Ph=phenyl; pyr=pyridyl, etc.) are used in the present specification.

The preferred compounds of the formula (I) containing a C5 chain, cyclopentyl (i.e. in which n=2, i.e. V=—$CH_2$—$CH_2$—, R3=cyclopentyl and R4=H, Z1=Z2=H) are especially the following:

TABLE 1

| X | Y | R1 | R2 | R3 | Acid/amide synthetic route | Analytical data (NMR and/or LC-MS) |
|---|---|----|----|----|---------------------------|------------------------------------|
| Ph | H | H | CH2Ph | (rac)-cyclopentyl | B/EDCI | (DMSO-d6): 1.07-2.36 (14H, m); 4.20-4.69 (4H, m); 7.10-8.81 (14H, m). |
| Ph | H | H | CH2-(2)-pyr | (rac)-cyclopentyl | B/EDCI | (DMSO-d6): 0.88-2.15 (14H, m); 4.14-4.43 (4H, m); 6.87-8.10 (12H, m); 8.19-8.48 (3H, m). |
| Ph | H | H | CH2-(4)-pyr | (rac)-cyclopentyl | B/EDCI | (DMSO-d6): 0.86-2.13 (14H, m); 4.17-4.36 (4H, m); 7.10-7.84 (8H, m); 7.94 (1H, s); 8.23-8.55 (5H, m). |
| Ph | H | H | CH2-(4)-SO2MePh | (rac)-cyclopentyl | B/EDCI | (DMSO-d6): 0.80-1.92 (14H, m); 3.12 (3H, s); 4.23-4.39 (4H, m); 7.12-7.30 (2H, m); 7.39-7.52 (4H, m); 7.66-7.75 (2H, m); 7.76-7.86 (2H, m); 7.95 (1H, s); 8.27-8.55 (3H, m). |

The preferred compounds of the formula (I) containing a C6 chain (in which n=3, Z1=Z2H), are especially the following:

TABLE 2

| X | Y | R1 | R2 | R3 | R4 | Analytical data (NMR and/or LC-MS) | Acid synthetic route | Amide synthetic route |
|---|---|----|----|----|----|-----------------------------------|---------------------|----------------------|
| Ph | H | H | CH2Ph | (rac)-cyclopentyl | H | (DMSO-d6): 0.83-2.24 (16H, m); 4.01-4.49 (4H, m); 7.11-7.32 (7H, m); 7.36-7.50 (2H, m); 7.62-7.78 (2H, m); 7.92 (1H, s); 8.17-8.39 (3H, m). | B | EDCl |
| Ph | H | H | CH2Ph | H | H | (DMSO-d6): 1.17-1.35 (2H, m); 1.48-1.67 (2H, m); 2.06-2.19 (2H, m); 4.16-4.35 (4H, m); 7.11-7.33 (7H, m); 7.35-7.51 (2H, m); 7.63-7.75 (2H, m); 7.97 (1H, s); 8.19-8.36 (3H, m). | A or B | EDCl |
| Ph | H | H | CH2-(4')-SO2MePh | (rac)-cyclopentyl | H | (DMSO-d6): 0.78-2.02 (16H, m); 3.15 (3H, s); 4.17-4.37 (4H, m); 7.07-7.30 (3H, m); 7.36-7.51 (4H, m); 7.64-7.77 (2H, m); 7.79-7.90 (2H, m); 7.93 (1H, s); 8.22-8.49 (3H, m). | B | EDCl |
| Ph | H | H | CH2-(4')-CO2MePh | (rac)-cyclopentyl | H | (DMSO-d6): 0.96-2.03 (16H, m); 3.82 (3H, s); 4.18-4.35 (4H, m); 7.12-7.49 (6H, m); 7.63-7.74 (2H, m); 7.83-7.96 (3H, m); 8.26-8.44 (3H, m). | B | EDCl |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | CH2-(benzo[1,3]dioxol-5-yl) | (rac)-cyclopentyl | H | (DMSO-d6): 0.86-2.13 (14H, m) 3.31 (2H, s); 3.87-4.45 (4H, m); 5.94 (2H, s); 6.64-6.91 (3H, m); 7.03-7.80 (6H, m); 7.91 (1H, s); 8.09-8.42 (3H, m). | B | EDCl |
| Ph | H | H | CH2-(4')-OMePh | (rac)-cyclopentyl | H | (DMSO-d6): 0.69-2.19 (16H, m); 3.68 (3H, s); 3.90-4.49 (4H, m); 6.65-7.83 (10H, m); 7.92 (1H, s); 8.08-8.45 (3H, m). | B | EDCl |
| Ph | H | H | CH2-(4')-CO2HPh | (rac)-cyclopentyl | H | (DMSO-d6): 0.84-2.10 (16H, m) 4.04-4.64 (4H, m); 7.03-8.07 (11H, m); 8.12-8.53 (3H, m); 12.83 (1H, broad s). | B | EDCl |
| Ph | H | H | CH2-(indan-1-yl) (one enantiomer) | (rac)-cyclopentyl | H | (CDCl3): 0.88-2.03 (16H, m); 2.26-2.93 (3H, m); 4.19-4.39 (2H, m); 5.33-5.47 (1H, m); 5.56-5.71 (1H, m); 6.98-7.27 (7H, m); 7.30-7.41 (3H, m); 7.50-7.60 (2H, m); 8.10-8.30 (2H, m). | B | EDCl |
| Ph | H | H | CH2-(indan-1-yl) (other enantiomer) | (rac)-cyclopentyl | H | (CDCl3): 0.73-2.06 (16H, m) 2.28-2.95 (3H, m); 4.20-4.42 (2H, m); 5.32-5.45 (1H, m); 5.58-5.72 (1H, m); 7.00-7.29 (7H, m) 7.31-7.43 (3H, m); 7.50-7.60 (2H, m); 8.13-8.31 (2H, m). | B | EDCl |
| Ph | H | H | CH2-(2')-pyr | (rac)-cyclopentyl | H | (CDCl3): 0.78-2.04 (16H, m) 3.96-4.19 (2H, m); 4.26-4.40 (2H, m); 6.60-7.15 (5H, mp); 7.16-7.28 (3H, m); 7.36-7.52 (3H, m); 7.94-8.33 (3H, m). | B | EDCl |
| Ph | H | H | CH2-(4-(6-fluoroquinolin-2-ylmethyl)piperidin-1-yl) | (rac)-cyclopentyl | H | (CDCl3): 0.90-2.42 (22H, m); 2.68-2.98 (2H, m); 3.73-3.91 (2H, m); 4.19-4.42 (2H, m); 5.29-5.44 (1H, m); 7.01-7.31 (2H, m); 7.34-7.52 (5H, m); 7.56-7.71 (3H, m); 7.99-8.12 (2H, m); 8.14-8.38 (2H, m). | B | EDCl |
| Ph | H | H | CH2CH2OPh | (rac)-cyclopentyl | H | (CDCl3): 0.88-2.00 (15H, m); 3.46-3.63 (2H, m); 3.83-3.95 (2H, m); 4.15-4.31 (2H, m); 5.89-6.02 (1H, m); 6.73-6.91 (3H, m); 7.04-7.45 (8H, m); 7.51-7.61 (2H, m); 8.13-8.23 (1H, m); 8.24-8.33 (1H, m). | B | EDCl |
| Ph | H | H | (rac)-CHMe-(4')-F-Ph (one diast.) | (rac)-cyclopentyl | H | (CDCl3): 0.80-2.00 (19H, m); 4.14-4.26 (2H, m); 4.98-5.09 (1H, m); 6.80-6.93 (2H, m); 7.05-7.44 (8H, m); 7.51-7.60 (2H, m); 8.14-8.23 (1H, m); 8.25-8.32 (1H, m). | B | EDCl |
| Ph | H | H | (rac)-CHMe-(4')-F-Ph (other diast) | (rac)-cyclopentyl | H | (CDCl3): 0.73-2.05 (19H, m); 4.22-4.39 (2H, m); 4.93-5.07 (1H, m); 6.83-6.98 (2H, m); 7.05-7.29 (5H, m); 7.34-7.46 (3H, m); 7.53-7.61 (2H, m); 8.16-8.30 (2H, m). | B | EDCl |
| Ph | H | H | CH2-(4')-CF3Ph | (rac)-cyclopentyl | H | (CDCl3): 0.90-2.03 (16H, m); 4.17-4.36 (3H, m); 4.37-4.49 (1H, m); 7.03-7.61 (12H, m); 8.13-8.31 (2H, m). | B | EDCl |
| Ph | H | H | CH2-(3')-pyr | (rac)-cyclopentyl | H | (CDCl3): 0.72-1.87 (16H, m); 3.99-4.41 (4H, m); 6.75-7.61 (10H, m); 7.97-8.06 (1H, m); 8.07-8.16 (1H, m); 8.21-8.38 (2H, m). | B | EDCl |
| Ph | H | H | CH2-(4')-pyr | (rac)-cyclopentyl | H | (CDCl3): 0.87-2.03 (16H, m); 4.09-4.46 (4H, m); 6.96-7.66 (10H, m); 8.09-8.30 (2H, m); 8.36-8.52 (2H, m). | B | EDCl |
| Ph | H | H | CH2-(4')-OCF3Ph | (rac)-cyclopentyl | H | (CDCl3): 0.72-1.90 (16H, m); 4.00-4.31 (4H, m); 6.82-7.48 (12H, m); 7.99-8.17 (2H, m). | B | EDCl |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | *chroman-2-ylmethyl* | (rac)-cyclopentyl | H | (CDCl3): 0.91-2.03 (18H, m); 2.57-2.84 (2H, m); 3.04-3.31 (1H, m); 3.53-3.74 (1H, m); 3.84-4.06 (1H, m); 4.17-4.37 (2H, m); 6.56-6.87 (2H, m); 6.87-7.65 (10H, m); 8.03-8.37 (2H, m). | B | EDCl |
| Ph | H | H | *2-methyl-3-(2,6-dimethylphenoxy)propyl* | (rac)-cyclopentyl | H | (DMSO-d6): 0.85-2.35 (25H, m); 3.14-3.79 (2H, m); 4.02-4.37 (3H, m); 6.81-7.52 (7H, m); 7.58-8.05 (4H, m); 8.13-8.42 (2H, m). | B | EDCl |
| Ph | H | H | CH2-(4')-SO2NH2Ph | (rac)-cyclopentyl | H | (DMSO-d6): 0.91-2.01 (18H, m); 4.11-4.38 (4H, m); 7.11-7.52 (6H, m); 7.64-7.84 (7H, m); 7.71-8.51 (3H, m). | B | EDCl |
| Ph | H | H | (R)-CH(Me)Ph | (rac)-cyclopentyl | H | (CDCl3): 0.79-2.20 (18H, m); 4.03-4.46 (2H, m); 5.02-5.22 (1H, m); 5.66-5.82 (1H, m); 7.06-7.54 (11H, m); 7.57-7.70 (2H, m); 8.14-8.40 (2H, m). | B | EDCl |
| Ph | H | H | (S)-CH(Me)Ph | (rac)-cyclopentyl | H | (CDCl3): 0.69-2.01 (18H, m); 3.93-4.37 (2H, m); 4.93-5.14 (1H, m); 5.59-5.76 (1H, m); 6.98-7.47 (11H, m); 7.50-7.66 (2H, m); 8.09-8.34 (2H, m). | B | EDCl |
| Ph | H | H | (2)-Pyrimidine | (rac)-cyclopentyl | H | ES+ = 454.4 | B | acid chloride |
| Ph | H | H | Cyclohexyl | (rac)-cyclopentyl | H | ES+ = 458.4 | B | acid chloride |
| Ph | H | H | (2)-CO2Me-Ph | (rac)-cyclopentyl | H | ES+ = 510.4 | B | acid chloride |
| Ph | H | H | CH2-(3)-Me-Ph | (rac)-cyclopentyl | H | ES+ = 480.4 | B | acid chloride |
| Ph | H | H | CH2CH2-(4')-OH-Ph | (rac)-cyclopentyl | H | ES+ = 496.4 | B | acid chloride |
| Ph | H | Ph | CH2CH2OH | (rac)-cyclopentyl | H | ES+ = 496.4 | B | acid chloride |
| Ph | H | H | (rac)-CHMe(CH2)3iPr | (rac)-cyclopentyl | H | ES+ = 488.5 | B | acid chloride |
| Ph | H | CH2Ph | CH2CH2OH | (rac)-cyclopentyl | H | ES+ = 510.1 | B | acid chloride |
| Ph | H | H | 2-thiazole | (rac)-cyclopentyl | H | ES+ = 459.4 | B | acid chloride |
| Ph | H | H | (CH2)3-morpholine | (rac)-cyclopentyl | H | ES+ = 503.4 | B | acid chloride |
| Ph | H | Me | CH2-(3')-pyr | (rac)-cyclopentyl | H | ES+ = 481.4 | B | acid chloride |
| Ph | H | Me | (CH2)2-(2')-pyr | (rac)-cyclopentyl | H | ES+ = 495.4 | B | acid chloride |
| Ph | H | H | (CH2)3-Net2 | (rac)-cyclopentyl | H | ES+ = 489.5 | B | acid chloride |
| Ph | H | H | *2-(2,3-dihydro-1,4-benzodioxin-6-yl)ethyl* | (rac)-cyclopentyl | H | ES+ = 524.4 | B | acid chloride |
| Ph | H | Me | Cyclohexyl | (rac)-cyclopentyl | H | ES+ = 472.5 | B | acid chloride |
| Ph | H | H | (4)-iPr-Ph | (rac)-cyclopentyl | H | ES+ = 494.4 | B | acid chloride |
| Ph | H | H | CMe(CH2OH)2 | (rac)-cyclopentyl | H | ES+ = 464.4 | B | acid chloride |
| Ph | H | H | (rac)-CHPh(CH2OH) | (rac)-cyclopentyl | H | ES+ = 496.4 | B | acid chloride |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | CH2-(3')-CF3-Ph | (rac)-cyclopentyl | H | ES+ = 534.4 | B | acid chloride |
| Ph | H | H | 4-Carboethoxyaminopiperidine | (rac)-cyclopentyl | H | ES+ = 531.5 | B | acid chloride |
| Ph | H | H | 2-Aminoethylpiperidine | (rac)-cyclopentyl | H | ES+ = 487.5 | B | acid chloride |
| Ph | H | H | (tetrahydroquinolinyl-methyl) | (rac)-cyclopentyl | H | ES+ = 506.5 | B | acid chloride |
| Ph | H | H | (CH2)3-N-(2)-pyrrolidinone | (rac)-cyclopentyl | H | ES+ = 501.5 | B | acid chloride |
| Ph | H | H | (CH2)3-N-(2)-imidazole | (rac)-cyclopentyl | H | ES+ = 484.5 | B | acid chloride |
| Ph | H | H | (CH2)3-N-(2')-methylpiperidine | (rac)-cyclopentyl | H | ES+ = 515.5 | B | acid chloride |
| Ph | H | H | (N-methylpyrrolidin-2-yl-propyl) | (rac)-cyclopentyl | H | ES+ = 487.5 | B | acid chloride |
| Ph | H | H | (CH2)2-(2')-thiophene | (rac)-cyclopentyl | H | ES+ = 486.4 | B | acid chloride |
| Ph | H | H | (4')-CH2PO(OEt)2-Ph | (rac)-cyclopentyl | H | ES+ = 602.5 | B | acid chloride |
| Ph | H | Me | (4')-OMe-Ph | (rac)-cyclopentyl | H | ES+ = 496.4 | B | acid chloride |
| Ph | H | H | CH(Ph)(CO2Et) | (rac)-cyclopentyl | H | ES+ = 538.4 | B | acid chloride |
| Ph | H | H | (1-(4-(2-hydroxyethyl)benzyl)cyclopentyl-methyl) | (rac)-cyclopentyl | H | ES+ = 592.6 | B | acid chloride |
| Ph | H | H | CH2C(Ph)2(CH2OH) | (rac)-cyclopentyl | H | ES+ = 586.5 | B | acid chloride |
| Ph | H | H | CH2CH2-(3')-(OMe)-Ph | (rac)-cyclopentyl | H | ES+ = 510.5 | B | acid chloride |
| Ph | H | CH2 Ph | (rac)-CH(Ph)(CH2OH) | (rac)-cyclopentyl | H | ES+ = 586.5 | B | acid chloride |
| Ph | H | CH2 Ph | CH2-(rac)-CH(Ph)(OH) | (rac)-cyclopentyl | H | ES+ = 586.5 | B | acid chloride |
| Ph | H | H | (rac)-CH(Ph)(CH2Ph) | (rac)-cyclopentyl | H | ES+ = 556.5 | B | acid chloride |
| Ph | H | H | CH2CH2O-(4')-(CO2Me)Ph | (rac)-cyclopentyl | H | ES+ = 554.4 | B | acid chloride |
| Ph | H | H | CH2CH2CHPh2 | (rac)-cyclopentyl | H | ES+ = 570 | B | acid chloride |
| Ph | H | CH2 Ph | (2')-pyr | (rac)-cyclopentyl | H | ES+ = 543.5 | B | acid chloride |
| Ph | H | H | ((4-(4-methoxyphenyl)-1-methyl-1H-pyrazol-3-yl)methyl) | (rac)-cyclopentyl | H | ES+ = 562.5 | B | acid chloride |
| Ph | H | H | (2)-Aminoethylpyrrolidine | (rac)-cyclopentyl | H | ES+ = 473.5 | B | acid chloride |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | (2-ethyl-pyrrolidin-1-yl)methyl | (rac)-cyclopentyl | H | ES+ = 487.5 | B | acid chloride |
| Ph | H | H | (1-benzyl-3-ethyl-pyrrolidin-3-yl)methyl | (rac)-cyclopentyl | H | ES+ = 535.5 | B | acid chloride |
| Ph | H | H | (3)-Aminopropyl-(N)-Me-piperazine | (rac)-cyclopentyl | H | ES+ = 516.5 | B | acid chloride |
| Ph | H | H | CH2(C=O)NHPh | (rac)-cyclopentyl | H | ES+ = 509.4 | B | acid chloride |
| Ph | H | H | (CH2)2O(C=O)(E)-(CH=CH)Ph | (rac)-cyclopentyl | H | ES+ = 550.5 | B | acid chloride |
| Ph | H | H | quinolin-6-ylmethyl | (rac)-cyclopentyl | H | ES+ = 503.4 | B | acid chloride |
| Ph | H | H | methyl 2-(4-hydroxybenzyl)butanoate | (rac)-cyclopentyl | H | ES+ = 554.4 | B | acid chloride |
| Ph | H | H | (2,2-difluoro-benzo[1,3]dioxol-5-yl)methyl | (rac)-cyclopentyl | H | ES+ = 532.4 | B | acid chloride |
| Ph | H | Me | (4')-(OH)-Ph | (rac)-cyclopentyl | H | ES+ = 482.4 | B | acid chloride |
| Ph | H | H | CH2-(2')-(OH)-(5')-(tBu)-Ph | (rac)-cyclopentyl | H | ES+ = 538.5 | B | acid chloride |
| Ph | H | H | (1-benzyl-cyclopentyl)methyl | (rac)-cyclopentyl | H | ES+ = 545.8 | B | acid chloride |
| Ph | H | H | (3-hydroxy-naphthalen-1-yl)methyl | (rac)-cyclopentyl | H | ES+ = 532.4 | B | acid chloride |
| Ph | H | H | CH2(C=O)NH-(2')-(CO2Et)-Ph | (rac)-cyclopentyl | H | ES+ = 581.5 | B | acid chloride |
| Ph | H | H | (S)-CH(CO2H)(CH2CO2CH2Ph) | (rac)-cyclopentyl | H | ES+ = 582.5 | B | acid chloride |

TABLE 2-continued

| X | Y | R1 | R2 | R3 | R4 | Analytical data (NMR and/or LC-MS) | Acid synthetic route | Amide synthetic route |
|---|---|----|----|----|----|----|----|----|
| Ph | H | H | *structure: (S)-2-(cyclohexa-1,4-dien-1-yl)butanoic acid* | (rac)-cyclopentyl | H | ES+ = 512.4 | B | acid chloride |
| Ph | H | H | CH2-(2')-(Br)-Ph | (rac)-cyclopentyl | H | ES+ = 544.3/546.3 | B | acid chloride |
| Ph | H | H | CH2-(2')-(Cl)-Ph | (rac)-cyclopentyl | H | ES+ = 500.4/502.4 | B | acid chloride |
| Ph | H | H | CH2-(3')-(Cl)-Ph | (rac)-cyclopentyl | H | ES+ = 500.4/502.4 | B | acid chloride |
| Ph | H | H | CH2-(4')-(Cl)-Ph | (rac)-cyclopentyl | H | ES+ = 500.4/502.4 | B | acid chloride |
| Ph | H | H | CH2-(2')-(F)-Ph | (rac)-cyclopentyl | H | ES+ = 484.4 | B | acid chloride |
| Ph | H | H | CH2-(3')-(F)-Ph | (rac)-cyclopentyl | H | ES+ = 484.4 | B | acid chloride |
| Ph | H | H | CH2-(4')-(F)-Ph | (rac)-cyclopentyl | H | ES+ = 484.4 | B | acid chloride |
| Ph | H | H | CH2-(2')-(Me)-Ph | (rac)-cyclopentyl | H | ES+ = 480.4 | B | acid chloride |
| Ph | H | H | CH2-(4')-(Me)-Ph | (rac)-cyclopentyl | H | ES+ = 480.4 | B | acid chloride |
| Ph | H | H | CH2-(6')-Me-(2')-pyr | (rac)-cyclopentyl | H | (DMSO-d6): 0.88-2.18 (16H, m); 2.40 (3H, s); 4.07-4.52 (4H, m); 6.86-7.36 (4H, m); 7.36-7.85 (5H, m); 7.93 (1H, s); 8.12-8.55 (3H, m). | B | EDCl |
| Ph | H | H | Ph | (rac)-cyclopentyl | H | ES+ = 452.4 | B | acid chloride |
| Ph | H | Me | CH2CH2-(3',4')-(OMe)Ph | (rac)-cyclopentyl | H | ES+ = 554.5 | B | acid chloride |
| Ph | H | Me | (S)-CH(Me)-(rac)-CH(OH)Ph | (rac)-cyclopentyl | H | ES+ = 524.5 | B | acid chloride |
| Ph | H | Me | CH2CH2Ph | (rac)-cyclopentyl | H | ES+ = 480.4 | B | acid chloride |
| Ph | H | Me | (rac)-CH(Me)-(CH2Ph) | (rac)-cyclopentyl | H | ES+ = 494.5 | B | acid chloride |
| H | H | H | CH2Ph | (rac)-cyclopentyl | H | (DMSO-d6): 0.56-1.96 (6H, m); 3.86-4.36 (4H, m); 6.33 (1H, s); 6.76-7.84 (7H, m); 7.71-8.51 (3H, m). | B | EDCl |
| H | H | H | CH2-(4')-(SO2Me)-Ph | (rac)-cyclopentyl | H | (DMSO-d6): 0.78-2.07 (16H, m); 3.18 (3H, s); 4.04-4.45 (4H, m); 6.44 (1H, s); 6.95-7.17 (1H, m); 7.31-7.67 (3H, m); 7.71-7.85 (5H, m). | B | EDCl |
| H | Ph | H | CH2Ph | (rac)-cyclopentyl | H | (DMSO-d6): 0.66-2.03 (16H, m); 4.05-4.41 (4H, m); 6.54 (1H, s); 7.06-7.35 (6H, m); 7.42-7.67 (5H, m); 7.92-8.01 (1H, m); 8.16-8.33 (2H, m). | B | EDCl |
| H | Ph | H | CH2-(4')-(SO2Me)-Ph | (rac)-cyclopentyl | H | (DMSO-d6): 0.76-1.91 (16H, m); 3.17 (3H, s); 4.19-4.39 (4H, m); 6.54 (1H, s); 7.07-7.17 (1H, m); 7.40-7.64 (7H, m); 7.81-8.02 (3H, m); 8.23-8.43 (2H, m). | B | EDCl |
| Ph | H | H | CH2Ph | *tert-butyl (Me-C(Me)-Me)* | | (DMSO-d6): 0.75-1.35 (8H, m); 1.40-1.60 (2H, m); 1.67-1.93 (2H, m); 4.09-4.38 (4H, m); 7.00-7.57 (9H, m); 7.61-7.82 (2H, m); 7.88-8.09 (2H, m); 8.21-8.41 (2H, m). | A | EDCl |
| Ph | H | H | CH2-(4')-(SO2Me)-Ph | *tert-butyl (Me-C(Me)-Me)* | | (DMSO-d6): 0.68-1.31 (8H, m); 1.44-1.90 (4H, m); 3.16 (3H, s); 4.15-4.46 (4H, m); 7.04-8.47 (14H, m). | A | EDCl |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | CH2-(2')-pyr | *tert-butyl (Me-C(Me)-)* | | (DMSO-d6): 0.89-1.36 (8H, m); 1.41-1.64 (2H, m); 1.67-1.93 (2H, m); 4.15-4.48 (4H, m); 6.97-8.60 (14H, m). | A | EDCl |
| Ph | H | H | CH2-(4')-pyr | *tert-butyl* | | (DMSO-d6): 0.74-1.33 (8H, m); 1.42-1.64 (2H, m); 1.68-1.92 (2H, m); 4.08-4.44 (4H, m); 7.02-8.62 (14H, m). | A | EDCl |
| Ph | H | H | CH2Ph | *1-methyl-2,3-dihydro-1H-indene* | | (DMSO-d6): 1.07-1.40 (2H, m); 1.52-2.00 (4H, m); 2.01-2.33 (1H, m); 2.52-2.66 (1H, m); 2.66-3.02 (2H, m); 4.01-4.53 (4H, m); 6.93-7.60 (13H, m); 7.60-7.82 (2H, m); 7.83-8.17 (2H, m); 8.17-8.48 (2H, m). | A | acid chloride |
| Ph | H | H | CH2Ph | *1-methylcyclopentyl* | | (DMSO-d6): 0.85-2.12 (14H, m); 4.05-4.68 (4H, m); 6.92-8.43 (15H, m). | A | EDCl |
| Ph | H | H | CH2-(4')-(SO2Me)-Ph | *1-methylcyclopentyl* | | (DMSO-d6): 0.89-2.11 (14H, m); 3.16 (3H, s); 4.06-4.45 (4H, m); 7.01-8.53 (14H, m). | A | EDCl |
| Ph | H | H | CH2-(2')-pyr | *1-methylcyclopentyl* | | (DMSO-d6): 0.67-2.29 (14H, m); 4.01-4.52 (4H, m); 6.89-8.63 (14H, m). | A | EDCl |
| Ph | H | H | CH2-(4')-pyr | *1-methylcyclopentyl* | | (DMSO-d6): 1.07-2.36 (14H, m); 4.20-4.69 (4H, m); 6.89-8.63 (14H, m). | A | EDCl |
| Ph | H | | *pyridinyl-CH2-* | (rac)-cyclopentyl | H | ES+ = 427.2 | B | acid chloride |
| Ph | H | | *ethyl 4-(methyl)piperidine-1-carboxylate* | (rac)-cyclopentyl | H | ES+ = 517.15 | B | acid chloride |
| Ph | H | | *ethyl cyclohexanecarboxylate with CH2* | (rac)-cyclopentyl | H | ES+ = 516.5 | B | acid chloride |
| Ph | H | | *benzyl (o-tolyl-CH2)* | (rac)-cyclopentyl | H | ES+ = 476.3 | B | acid chloride |

TABLE 2-continued

| X | Y | R1 R2 | R3 | R4 | Analytical data (NMR and/or LC-MS) | Acid synthetic route | Amide synthetic route |
|---|---|---|---|---|---|---|---|
| Ph | H | (2-phenylpropyl)piperidinyl | (rac)-cyclopentyl | H | ES+ = 563.4 | B | acid chloride |
| Ph | H | 1-(3,4-dimethoxyphenyl)butyl | (rac)-cyclopentyl | H | ES+ = 566.5 | B | acid chloride |
| Ph | H | 1-phenylpentyl | (rac)-cyclopentyl | H | ES+ = 506.5 | B | acid chloride |
| Ph | H | 1-(pyridin-3-ylthio)ethyl | (rac)-cyclopentyl | H | ES+ = 525.4 | B | acid chloride |
| Ph | H | (Boc-aminomethyl)cyclohexyl | (rac)-cyclopentyl | H | ES+ = 573.5 | B | acid chloride |
| Ph | H | 2-(piperidinyl)phenol | (rac)-cyclopentyl | H | ES+ = 537.5 | B | acid chloride |
| Ph | H | 4-(pyrrolidin-1-yl)piperidinyl | (rac)-cyclopentyl | H | ES+ = 513.5 | B | acid chloride |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | | 4-carbamoylcyclohexyl | (rac)-cyclopentyl | H | ES+ = 487.5 | B | acid chloride |
| Ph | H | | 4-(methoxycarbonyl)cyclohexyl | (rac)-cyclopentyl | H | ES+ = 502.5 | B | acid chloride |
| Ph | H | | decahydronaphthalen-2-yl | (rac)-cyclopentyl | H | ES+ = 498.5 | B | acid chloride |
| Ph | H | | 4-(hydroxymethyl)cyclohexyl | (rac)-cyclopentyl | H | ES+ = 474.5 | B | acid chloride |
| Ph | H | | 4-(2-hydroxyethyl)cyclohexyl | (rac)-cyclopentyl | H | ES+ = 488.5 | B | acid chloride |
| Ph | H | | 2-cyclohexylpropanoic acid moiety | (rac)-cyclopentyl | H | ES+ = 474.4 | B | acid chloride |
| Ph | H | | 1,2,3,4-tetrahydronaphthalen-2-yl | (rac)-cyclopentyl | H | ES+ = 492.5 | B | acid chloride |
| Ph | H | | 4-benzylcyclohexyl | (rac)-cyclopentyl | H | ES+ = 534.5 | B | acid chloride |
| Ph | H | H | CH2Ph | (rac)-cyclohexyl | H | (DMSO-d6): 0.71-1.98 (18H, m); 4.10-4.36 (4H, m); 7.12-7.31 (7H, m); 7.38-7.49 (2H, m); 7.65-7.75 (2H, m); 7.91 (1H, s); 8.19-8.36 (3H, m). | A | EDCl |
| Ph | H | H | CH2-(4')-(SO2Me)-Ph | (rac)-cyclohexyl | H | (DMSO-d6): 0.67-2.02 (18H, m); 3.15 (3H, s); 4.20-4.37 (2H, m); 7.12-7.28 (2H, m); 7.36-7.50 (4H, m); 7.64-7.75 (2H, m); 7.81-7.90 (2H, m); 7.963 (1H, s); 8.24-8.45 (3H, m). | A | EDCl |
| Ph | H | H | CH2-(2')-pyr | (rac)-cyclohexyl | H | (DMSO-d6): 0.70-2.06 (18H, m); 4.16-4.40 (4H, m); 7.10-7.29 (4H, m); 7.36-7.49 (2H, m); 7.62-7.76 (3H, m); 7.93 (1H, s); 8.22-8.50 (4H, m). | A | EDCl |
| Ph | H | H | CH2-(4')-pyr | (rac)-cyclohexyl | H | (DMSO-d6): 0.7-2.00 (18H, m); 4.13-4.36 (4H, m); 7.09-7.28 (4H, m); 7.37-7.47 (2H, m); 7.65-7.74 (2H, m); 7.94 (1H, s); 8.24-8.49 (5H, m). | A | EDCl |
| Ph | H | H | CH2-(6')-Me-(2')-pyr | (rac)-cyclohexyl | H | (DMSO-d6): 0.62-2.19 (18H, m); 2.39 (1H, m); 4.05-4.53 (4H, m); 6.85-7.85 (9H, m); 7.92 (1H, s); 8.12-8.56 (3H, m). | A | EDCl |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | CH2Ph | (rac)-2-butyl | H | (DMSO-d6): 0.72-0.85 (6H, m); 0.89-2.10 (10H, m); 4.15-4.38 (4H, m); 7.11-7.32 (7H, m); 7.38-7.49 (2H, m); 7.64-7.76 (2H, m); 7.952 (1H, s); 8.22-8.35 (3H, m). | A | EDCl |
| Ph | H | H | CH2-(2')-pyr | (rac)-2-butyl | H | (DMSO-d6): 0.69-0.85 (6H, m); 0.92-2.16 (10H, m); 4.18-4.37 (4H, m); 7.10-7.28 (4H, m); 7.35-7.48 (2H, m); 7.61-7.75 (3H, m); 7.94 (1H, s); 8.23-8.49 (4H, m). | A | EDCl |
| Ph | H | H | CH2-(4')-pyr | (rac)-2-butyl | H | (DMSO-d6): 0.67-0.86 (6H, m); 0.92-2.15 (10H, m); 4.10-4.38 (4H, m); 7.07-7.29 (4H, m); 7.34-7.48 (2H, m); 7.61-7.75 (2H, m); 7.94 (1H, s); 8.21-8.50 (5H, m). | A | EDCl |
| Ph | H | H | CH2-(4')-(SO2Me)-Ph | (rac)-2-butyl | H | (DMSO-d6): 0.65-0.87 (6H, m); 0.91-2.09 (10H, m); 4.17-4.37 (4H, m); 7.10-7.29 (2H, m); 7.34-7.49 (4H, m); 7.62-7.74 (2H, m); 7.79-7.92 (2H, m); 7.94 (1H, s) 8.23-8.47 (3H, m). | A | EDCl |
| Ph | H | H | CH2Ph | (rac)-(2',3')-cyclopentenyl | H | (DMSO-d6): 1.01-2.77 (12H, m); 4.12-4.34 (4H, m); 5.43-5.82 (2H, m); 7.14-7.31 (7H, m); 7.39-7.47 (2H, m); 7.67-7.73 (2H, m); 7.92 (1H, s); 8.26-8.34 (3H, m). | A | EDCl |
| Ph | H | H | CH2-(4')-(SO2Me)-Ph | (rac)-(2',3')-cyclopentenyl | H | (DMSO-d6): 0.96-2.77 (12H, m); 3.16 (3H, s); 4.22-4.37 (4H, m); 5.44-5.78 (2H, m); 7.15-7.27 (2H, m); 7.39-7.47 (4H, m); 7.68-7.73 (2H, m); 7.83-7.88 (2H, m); 7.94 (1H, s); 8.27-8.48 (3H, m). | A | EDCl |
| Ph | H | H | CH2-(2')-pyr | (rac)-(2',3')-cyclopentenyl | H | (DMSO-d6): 1.02-2.78 (12H, m); 4.19-4.48 (4H, m); 5.48-5.79 (2H, m); 7.14-7.28 (4H, m); 7.38-7.47 (2H, m); 7.65-7.74 (3H, m); 7.94 (1H, s); 8.26-8.49 (4H, m). | A | EDCl |
| Ph | H | H | CH2-(4')-pyr | (rac)-(2',3')-cyclopentenyl | H | (DMSO-d6): 0.99-2.83 (12H, m); 4.13-4.36 (4H, m); 5.44-5.79 (4H, m); 7.39-7.47 (2H, m); 7.67-7.74 (2H, m); 7.94 (1H, s); 8.27-8.50 (5H, m). | A | EDCl |
| Ph | H | H | CH2Ph | (rac)-phenyl | H | (DMSO-d6): 0.98-2.20 (6H, m); 3.37-4.56 (1H, m); 3.87-4.49 (4H, m); 6.69-7.76 (16H, m); 7.92 (2H, s); 8.05-8.67 (3H, M). | A | EDCl |
| Ph | H | H | CH2-(4')-(SO2Me)-Ph | (rac)-phenyl | H | (DMSO-d6): 0.97-2.30 (6H, m); 3.15 (3H, s); 3.39-6.62 (1H, m); 4.13-4.56 (4H, m); 6.94-6.86 (15H, m); 7.93 (1H, s; 8.09-8.73 (3H, m). | A | EDCl |
| Ph | H | H | CH2-(2')-pyr | (rac)-phenyl | H | (DMSO-d6): 0.56-2.18 (6H, m); 3.39-3.63 (1H, M); 4.01-4.53 (4H, m); 6.79-6.81 (14H, m); 7.93 (1H, s); 8.07-8.75 (4H, m). | A | EDCl |
| Ph | H | H | CH2-(4')-pyr | (rac)-phenyl | H | (DMSO-d6): 0.94-2.23 (6H, m); 3.39-3.61 (1H, m); 4.07-4.46 (4H, m); 6.76-7.81 (13H, m); 7.93 (1H, s); 8.09-8.85 (5H, m). | A | EDCl |
| Ph | H | H | CH2-(6')-Me-(2')-pyr | (rac)-phenyl | H | (DMSO-d6): 0.98-2.17 (6H, m); 2.38 (3H, s); 3-46-3.62 (1H, m); 4.12-4.44 (4H, m); 6.65-8.13 (15H, m); 8.13-8.79 (3H, m). | A | EDCl |
| Ph | H | H | CH2Ph | (rac)-isopropyl | H | (DMSO-d6): 0.60-2.05 (14H, m); 3.97-4.49 (4H, m); 6.96-7.57 (9H, m); 7.57-7.82 (2H, m); 7.92 (1H, s); 8.08-8.49 (3H, m). | A | EDCl |
| Ph | H | H | CH2-(4')-(SO2Me)-Ph | (rac)-isopropyl | H | (DMSO-d6): 0.47-2.1 (14H, m) 3.16 (3H, s); 4.05-4.48 (4H, m); 6.97-7.57 (6H, m); 7.58-8.11 (5H, m); 8.11-8.57 (3H, m). | A | EDCl |
| Ph | H | H | CH2-(2')-pyr | (rac)-isopropyl | H | (DMSO-d6): 0.38-2.20 (14H, m); 3.87-4.66 (4H, m); 6.91-8.11 (11H, m); 8.11-8.71 (3H, m). | A | EDCl |

TABLE 2-continued

| X | Y | R1 | R2 | R3 | R4 | Analytical data (NMR and/or LC-MS) | Acid synthetic route | Amide synthetic route |
|---|---|----|----|----|----|-----|---|---|
| Ph | H | H | CH2-(4')-pyr | (rac)-isopropyl | H | (DMSO-d6): 0.58-2.09 (14H, m); 4.01-4.46 (4H, m); 6.95-7.30 (4H, m); 7.30-7.54 (2H, m); 7.54-7.81 (2H, m); 7.94 (1H, s); 8.09-8.60 (5H, m). | A | EDCl |
| Ph | H | H | CH2-(6')-Me-(2')-pyr | (rac)-isopropyl | H | (DMSO-d6): 0.39-2.21 (14H, m); 2.68 (3H, m); 4.02-4.71 (4H, m); 7.08-7.85 (8H, m); 7.96 (1H, s); 8.10-8.57 (3H, m); 15.78 (1H, broad s). | A | EDCl |
| Ph | H | H | CH2Ph | (rac)-cycloheptyl | H | (DMSO-d6): 0.77-2.19 (20H, m); 3.98-4.53 (4H, m); 6-97-7.84 (11H, m); 7.92 (1H, s); 8.09-8.54 (3H, m). | A | EDCl |
| Ph | H | H | CH2-(4')-(SO2Me)-Ph | (rac)-cycloheptyl | H | (DMSO-d6): 0.62-2.19 (20H, m); 3.16 (3H, s); 4.05-4.51 (4H, m) 7.03-7.33 (2H, m); 7.33-7.60 (4H, m); 7.60-7.79 (2H, m); 7.79-8.13 (3H, m); 8.14-8.59 (3H, m). | A | EDCl |
| Ph | H | H | CH2-(2')-pyr | (rac)-cycloheptyl | H | (DMSO-d6): 0.56-2.37 (20H, m); 4.02-4.67 (4H, m); 6.99-8.14 (10H, m); 8.14-8.74 (4H, m). | A | EDCl |
| Ph | H | H | CH2-(4')-pyr | (rac)-cycloheptyl | H | (DMSO-d6): 0.59-2.21 (20H, m); 4.01-4.55 (4H, m); 6.98-7.59 (6H, m); 7.59-7.84 (2H, m); 7.94 (1H, s); 8.11-8.66 (5H, m). | A | EDCl |
| Ph | H | H | CH2-(6')-Me-(2')-pyr | (rac)-cycloheptyl | H | (DMSO-d6): 0.93-2.16 (20H, m); 2.40 (3H, s); 4.12-4.43 (4H, m); 6.83-7.84 (10H, m); 7.93 (1H, s); 8.13-8.53 (3H, m). | A | EDCl |
| Ph | H | H | CH2Ph | (rac)-tert-butyl | H | (DMSO-d6): 0.85 (9H, s); 1.00-2.10 (7H, m); 4.01-4.52 (4H, m); 7.00-7.61 (9H, m); 7.61-7.85 (2H, m); 7.91 (1H, s) 8.09-8.51 (3H, m). | A | EDCl |
| Ph | H | H | CH2-(2')-pyr | (rac)-tert-butyl | H | (DMSO-d6): 0.86 (9H, s); 0.98-2.12 (7H, m); 4.06-4.61 (4H, m); 7.00-8.15 (10H, m); 8.15-8.71 (4H, m). | A | EDCl |
| Ph | H | H | CH2-(4')-pyr | (rac)-tert-butyl | H | (DMSO-d6): 0.86 (9H, s); 0.96-2.11 (7H, m); 4.02-4.52 (4H, m); 7.01-7.60 (6H, m); 7.60-7.87 (2H, m); 7.94 (1H, s); 8.14-8.66 (5H, m). | A | EDCl |
| Ph | H | H | CH2Ph | (R)-allyl | H | (DMSO-d6): 1.13-2.34 (9H, m); 4.10-4.35 (4H, m); 4.88-5.05 (2H, m); 5.57-5.77 (1H, m); 7.12-7.33 (7H, m); 7.39-7.50 (2H, m); 7.65-7.78 (2H, m); 7.93 (1H, s); 8.26-8.39 (3H, m). | C | EDCl |
| Ph | H | H | CH2Ph | (rac)-allyl | H | (DMSO-d6): 1.08-2.38 (9H, m); 4.02-4.49 (4H, m); 4.79-5.16 (2H, m); 5.50-5.96 (1H, m); 7.03-7.60 (9H, m); 7.60-7.84 (2H, m); 7.93 (1H, s); 8.13-8.51 (3H, m). | B | EDCl |
| Ph | H | H | CH2-(4')-(SO2Me)-Ph | (rac)-allyl | H | (DMSO-d6): 1.02-2.40 (9H, m); 3.16 (3H, s); 4.14-4.51 (4H, m); 4.81-5.16 (2H, m); 5.51-5.92 (1H, m); 7.05-8.05 (11H, m); 8.21-8.58 (3H, m). | B | EDCl |
| Ph | H | H | CH2-(4')-pyr | (rac)-allyl | H | (DMSO-d6): 1.07-2.40 (9H, m); 4.01-4.51 (4H, m); 4.81-5.20 (2H, m); 5.51-5.93 (1H, m); 7.00-8.12 (9H, m); 8.16-8.69 (5H, m). | B | EDCl |
| Ph | H | H | CH2Ph | (R)-methyl | H | (DMSO-d6): 0.79-2.39 (10H, m); 4.04-4.53 (4H, m); 7.03-8.11 (12H, m); 8.11-8.60 (3H, m). | C | EDCl |
| Ph | H | H | CH2-(4')-(SO2Me)-Ph | (R)-methyl | H | (DMSO-d6): 0.84-2.42 (13H, m); 4.12-4.65 (4H, m); 7.03-8.21 (11H, m); 8.21-8.68 (3H, m). | C | EDCl |
| Ph | H | H | CH2-(2')-pyr | (R)-methyl | H | (DMSO-d6): 0.83-2.43 (10H, m); 4.12-4.62 (4H, m); 7.03-8.15 (10H, m) 8.16-8.73 (4H, m). | C | EDCl |
| Ph | H | H | CH2-(4')-pyr | (R)-methyl | H | (DMSO-d6): 0.90-2.42 (10H, m); 4.06-4.62 (4H, m); 7.01-8.21 (9H, m) 8.21-8.84 (5H, m). | C | EDCl |
| Ph | H | H | CH2Ph | (S)-methyl | H | (CDCl3): 0.90-2.46 (10H, m); 4.23-4.44 (4H, m); 7.19-7.42 (7H, m); 7.45-7.57 (2H, m); 7.73-7.85 (2H, m); 8.00 (1H, s); 8.27-8.45 (3H, m). | C | EDCl |

TABLE 2-continued

| X | Y | R1 | R2 | R3 | R4 | Analytical data (NMR and/or LC-MS) | Acid synthetic route | Amide synthetic route |
|---|---|---|---|---|---|---|---|---|
| Ph | H | H | CH2-(4')-(SO2Me)-Ph | (S)-methyl | H | (DMSO-d6): 0.88-2.41 (10H, m); 3.16 (3H, s); 4.21-4.41 (4H, m); 7.12-7.33 (2H, m); 7.37-7.55 (4H, m); 7.65-7.79 (2H, m); 7.81-7.93 (2H, m); 7.96 (1H, s); 8.25-8.48 (3H, m). | C | EDCl |
| Ph | H | H | CH2-(2')-pyr | (S)-methyl | H | (DMSO-d6): 0.88-2.44 (10H, m); 4.20-4.39 (4H, m); 7.13-.730 (4H, m); 7.38-7.50 (2H, m); 7.65-7.78 (3H, m); 7.96 (1H, s); 8.25-8.52 (4H, m). | C | EDCl |
| Ph | H | H | CH2-(4')-pyr | (S)-methyl | H | (DMSO-d6): 0.90-2.41 (10H, m); 4.07-4.49 (4H, m); 7.12-7.30 (4H, m); 7.39-50 (2H, m); 7.66-7.76 (2H, m); 7.96 (1H, s); 8.26-8.52 (5H, m). | C | EDCl |
| Ph | H | H | CH2-[(2')-Cl-(5')-CF3]-Ph | (rac)-Cycloheptyl | H | (DMSO-d6): 0.57-2.33 (20H, m); 4.00-4.57 (4H, m); 7.01-7.83 (9H, m); 7.92 (1H, s) 8.14-8.63 (3H, m). | A | EDCl |
| Ph | H | H | CH2-(4')-nBut-Ph | (rac)-Cycloheptyl | H | (DMSO-d6): 0.62-2.15 (29H, m); 3.98-4.46 (4H, m); 6.90-7.81 (10H, m) 7.92 (1H, s); 8.07-8.45 (3H, m). | A | EDCl |
| Ph | H | H | CH2-(3')-F-(4')-CF3-Ph | (rac)-Cycloheptyl | H | (CDCl$_3$): 0.45-2.32 (20H, m); 3.99-4.51 (4H, m); 6.99-7.49 (6H, m) 7.59-7.86 (3H, m); 7.93 (1H, s) 8.14-8.70 (3H, m). | A | EDCl |
| Ph | H | H | CH2-(2')-F-(6')-Cl | (rac)-Cycloheptyl | H | (DMSO-d6): 0.50-2.07 (20H, m); 4.00-4.49 (4H, m); 7.00-7.58 (7H, m); 7.58-7.81 (2H, m); 7.81-8.16 (2H, m); 8.16-8.46 (2H, m). | A | EDCl |
| Ph | H | H | CH2-(2')-F-Ph | (rac)-Cycloheptyl | H | (DMSO-d6): 0.53-2.10 (20H, m); 4.00-4.47 (4H, m); 6.86-7.57 (8H, m) 7.57-7.83 (2H, m); 7.92 (1H, s) 8.09-8.49 (3H, m). | A | EDCl |
| Ph | H | H | CH2-(3')-Br-(4')-F-Ph | (rac)-Cycloheptyl | H | (DMSO-d6): 0.95-2.05 (20H, m); 3.96-4.45 (4H, m); 7.02-7.58 (7H, m) 7.58-7.82 (2H, m); 7.92 (1H, s) 8.14-8.48 (3H, m). | A | EDCl |
| Ph | H | H | CH2-isoxazol-2H-3-on-5-yl | (rac)-Cycloheptyl | H | (DMSO-d6): 0.43-2.22 (20H, m); 3.87-4.53 (4H, m); 6.99-8.14 (8H, m); 8.14-8.59 (3H, m) 11.42 (1H, broad s). | A | EDCl |
| Ph | H | H | CH2—CH=C(CH3)—(CH2)2—CH=C(CH3)2 | (rac)-Cycloheptyl | H | (DMSO-d6): 0.54-2.34 (31H, m); 3.44-3.74 (2H, m); 4.00-4.48 (2H, m) 4.86-5.21 (2H, m); 6.94-8.10 (11H, m); 8.10-8.49 (2H, m). | A | EDCl |
| Ph | H | H | CH2-(4')-COOMe-Ph | (rac)-Cycloheptyl | H | (DMSO-d6): 0.55-2.18 (20H, m); 3.82 (3H, s); 4.00-4.51 (4H, m) 6.98-7.53 (6H, m); 7.53-8.12 (5H, m) 8.12-8.58 (3H, m). | A | EDCl |
| Ph | H | H | CH2-(2')-F-(4')-Cl | (rac)-Cycloheptyl | H | (DMSO-d6): 0.93-2.16 (20H, m); 4.00-4.47 (4H, m); 7.01-7.57 (7H, m) 7.57-7.82 (20H, m); 7.92 (1H, s) 8.11-8.48 (3H, m). | A | EDCl |

As other compounds containing a C6 chain in which n=3, i.e. V=CH$_2$—CH$_2$—CH$_2$ (in which Z1=Z2=H), mention may be made of those given in the table below.

Where appropriate, the enantiomers were separated by HPLC on Chiralpak AD (EtOH solvent) and the $\alpha_D$ values measured.

| Compounds | X | Y | R1 | R2 | R3 | R4 | NMR | LCMS/$\alpha_D$ | Synthetic route |
|---|---|---|---|---|---|---|---|---|---|
| | (3')-pyr | H | H | (2')-pyr | (rac)-cyclohexyl | H | (DMSO-D6) 1.3 (m, 18H) 4.3 (m, 4H) 7.2 (m, 3H) 7.4 (dd, J = 7.9, 4.9 Hz, 1H) 7.7 (m, 1H) 8.1 (s, 2H) 8.4 (m.5H) 9.0 (d, J = 2.3 Hz, 1H) | | D |
| | Ph | H | H | CH2-(4')-(SO3H—NH—CO)-Ph | (rac)-cycloheptyl | H | | | D |
| | Ph | H | H | CH2-(4')-(SO3H)-Ph | (rac)-cycloheptyl | H | | | D |

-continued

| Compounds | X | Y | R1 | R2 | R3 | R4 | NMR | LCMS/α_D | Synthetic route |
|---|---|---|---|---|---|---|---|---|---|
| | Ph | H | H | CH2-(4')-(amidino)-Ph | (rac)-cycloheptyl | H | | | D |
| enantiomers | Ph | H | H | CH2-(2')-pyr | (rac)-cyclohexyl | H | | $\alpha_D$ = +7.1° and −7.9° | D |
| diastereoisomers | Ph | H | H | CH(Me)-Ph | (rac)-cycloheptyl | H | (DMSO-D6) 1.5 (m, 19H) 1.3 (d, J = 7.1 Hz, 3H) 2.0 (m, 1H) 4.2 (m, 2H) 4.9 (m, 1H) 7.2 (m, 7H) 7.4 (t, J = 7.5 Hz, 2H) 7.7 (d, J = 7.2 Hz, 2H) 7.9 (s, 1H) 8.2 (d, J = 8.2 Hz, 1H) 8.3 (m, 2H) (DMSO-D6) 1.3 (m, 17H) 1.2 (d, J = 7.1 Hz, 3H) 1.8 (m, 2H) 2.0 (m, 1H) 4.3 (m, 2H) 4.9 (m, 1H) 7.2 (m, 7H) 7.4 (t, J = 7.7 Hz, 2H) 7.7 (d, J = 7.2 Hz, 2H) 8.0 (s, 1H) 8.1 (d, J = 8.0 Hz, 1H) 8.3 (m, 2H) | ES+ 508.4 | A + EDCl |
| diastereoisomers | Ph | H | H | CH(CH2OH)-Ph | (rac)-cycloheptyl | H | Diastereoisomer 1: (DMSO-D6) 1.6 (m, 19H) 2.1 (m, 1H) 3.5 (t, J = 5.9 Hz, 2H) 4.2 (t, J = 6.9 Hz, 2H) 4.8 (t, J = 5.5 Hz, 1H) 4.8 (m, 1H) 7.2 (m, 7H) 7.4 (t, J = 8.0 Hz, 2H) 7.7 (d, J = 8.0 Hz, 2H) 7.9 (s, 1H) 8.1 (d, J = 8.2 Hz, 1H) 8.3 (m, 2H) | Diastereoisomer 1: ES+ 524.5 ES− 522.6 Diastereoisomer 2: ES+ 524.4 | A + EDCl |
| | Ph | H | H | CH2-(2')-pyridine oxide | (rac)-cyclohexyl | H | (DMSO-D6) 1.5 (m, 18H) 4.3 (m, 4H) 7.2 (m, 5H) 7.4 (t, J = 7.6 Hz, 2H) 7.7 (m, 2H) 8.0 (s, 1H) 8.3 (m, 4H°) | ES+ 497.5 | N-Oxide |
| | Ph | H | H | CH2-(4')-(MeOCH2OCO)-Ph | (rac)-cycloheptyl | H | (DMSO-D6) 1.4 (m, 18H) 3.4 (s, 3H) 4.2 (m, 4H) 5.4 (s, 2H) 5.8 (s, 2H) 7.2 (dd, J = 7.7, 4.9 Hz, 1H) 7.2 (t, J = 7.3 Hz, 1H) 7.3 (d, J = 8.2 Hz, 2H) 7.4 (t, J = 7.7 Hz, 2H) 7.7 (d, J = 8.0 Hz, 2H) 7.9 (m, 3H) 8.3 (m, 2H) 8.4 (t, J = 5.8 Hz, 1H) | ES+ 582.6 | A + EDCl + modification of R2 |
| | Ph | H | H | CH2-(4')-[Si(CH3)3-(CH2)2-O—CH2-O—CO]-Ph | (rac)-cycloheptyl | H | (DMSO-D6) −0.0 (s, 9H) 1.2 (m, 20H) 3.7 (t, J = 8.1 Hz, 2H) 4.3 (m, 4H) 5.5 (s, 2H) 5.8 (s, 2H) 7.2 (dd, J = 7.6, 5.0 Hz, 1H) 7.2 (t, J = 7.3 Hz, 1H) 7.3 (d, J = 8.2 Hz, 2H) 7.4 (t, J = 7.6 Hz, 2H) 7.7 (d, J = 8.0 Hz, 2H) 7.9 (m, J = 6.7 Hz, 3H) 8.3 (m, 2H) 8.4 (t, J = 5.8 Hz, 1H) | ES+ 668.7 | A + EDCl + modification of R2 |
| | Ph | H | H | —CH2Ph(4')(—SO2—NH2) | (rac)-cycloheptyl | H | | ES+ 573.6 | A + EDCl |
| | Ph | H | H | CH2-(4')-[(Me)2NHCO]-Ph | (rac)-cycloheptyl | H | | | D |
| | Ph | H | H | CH2-(4')-[C(Cl)3-CH2-O—CO]-Ph | (rac)-cycloheptyl | H | (DMSO-D6) 1.3 (m, 20H) 4.2 (m, 4H) 5.1 (s, 2H) 7.2 (m, 2H) 7.4 (m, 4H) 7.7 (m, 2H) 8.0 (m, 3H) 8.3 (m, 2H) 8.4 (t, J = 5.8 Hz, 1H) | ES+ 668.5/670.5/672.5/674.5 | A + EDCl + modification of R2 |
| | Ph | H | H | CH2-(4')-[(2')-pyr-(CH2)2-O—CO]-Ph | (rac)-cycloheptyl | H | (DMSO-D6) 1.3 (m, 20H) 3.2 (t, J = 6.5 Hz, 2H) 4.2 (m, 4H) 4.6 (t, J = 6.6 Hz, 2H) 7.2 (m, 6H) 7.4 (t, J = 7.6 Hz, 2H) 7.7 (m, 3H) 7.8 (d, J = 8.0 Hz, 2H) 7.9 (s, 1H) 8.3 (m, 3H) 8.5 (m, 1H) | ES+ 643.8 | A + EDCl + modification of R2 |
| | Ph | H | H | CH2-(4')-(CH2=CHCH2OC=O)Ph | (rac)-cycloheptyl | H | (DMSO-D6) 1.2 (m, 19H) 2.0 (s, 1H) 4.2 (m, 4H) 4.8 (d, J = 5.3 Hz, 2H) 5.33 (m, 2H) 6.0 (m, 1H) 7.2 (m, 2H) 7.3 (d, J = 8.2 Hz, 2H) 7.4 (t, J = 7.6 Hz, 2H) 7.7 (m, 3H) 7.9 (d, J = 9.9 Hz, 2H) 8.3 (m, 3H) | ES+ 578.7 | A + EDCl + modification of R2 |
| | Ph | H | H | CH2-(4')-(Et-S—CO)-Ph | (rac)-cycloheptyl | H | | | D |
| | Ph | H | H | CH2-(4')-(allyl-O—CO)-Ph | (rac)-cycloheptyl | H | | | D |
| | Ph | H | H | CH2-(4')-[Si(CH3)3-(CH2)2-O—CO]-Ph | (rac)-cycloheptyl | H | | | D |

-continued

| Compounds | X | Y | R1 | R2 | R3 | R4 | NMR | LCMS/α_D | Synthetic route |
|---|---|---|---|---|---|---|---|---|---|
| | (4')-F-Ph | H | H | CH2-(2')-pyr | (rac)-cyclohexyl | H | | | D |
| | (4')-Br-Ph | H | H | CH2-(2')-pyr | (rac)-cyclohexyl | H | | | D |
| | 2-thienyl | H | H | CH2-(2')-pyr | (rac)-cyclohexyl | H | | | D |
| | CH3 | H | H | CH2-(2')-pyr | (rac)-cyclohexyl | H | | | D |
| | (4')-MeO-Ph | H | H | CH2-(2')-pyr | (rac)-cyclohexyl | H | | | D |
| | 2-furanyl | H | H | CH2-(2')-pyr | (rac)-cyclohexyl | H | | | D |
| | 2-benzo[b]-furanyl | H | H | CH2-(2')-pyr | (rac)-cyclohexyl | H | | | D |
| | (4')-CF3-Ph | H | H | CH2-(2')-pyr | (rac)-cyclohexyl | H | | | D |
| | (4')-COOH-Ph | H | H | CH2-(2')-pyr | (rac)-cyclohexyl | H | | | D |
| | (4')-Cl-Ph | H | H | CH2-(2')-pyr | (rac)-cyclohexyl | H | | | D |
| | (4')-tert-but-Ph | H | H | CH2-(2')-pyr | (rac)-cyclohexyl | H | | | D |
| | (3')-Cl-Ph | H | H | CH2-(2')-pyr | (rac)-cyclohexyl | H | | | D |
| | (3')-NO2-Ph | H | H | CH2-(2')-pyr | (rac)-cyclohexyl | H | | | D |
| | 2-naphthyl | H | H | CH2-(2')-pyr | (rac)-cyclohexyl | H | | | D |
| | (2',4')-Cl-Ph | H | H | CH2-(2')-pyr | (rac)-cyclohexyl | H | | | D |
| | (3',4')-Me-Ph | H | H | CH2-(2')-pyr | (rac)-cyclohexyl | H | | | D |
| | o-tolyl | H | H | CH2-(2')-pyr | (rac)-cyclohexyl | H | | | D |
| | (3')-MeO-Ph | H | H | CH2-(2')-pyr | (rac)-cyclohexyl | H | | | D |
| | (3')-CF3-Ph | H | H | CH2-(2')-pyr | (rac)-cyclohexyl | H | | | D |
| | (4')-Me-Ph | H | H | CH2-(2')-pyr | (rac)-cyclohexyl | H | | | D |
| | (2')-F-Ph | H | H | CH2-(2')-pyr | (rac)-cyclohexyl | H | | | D |
| | (3')-F-Ph | H | H | CH2-(2')-pyr | (rac)-cyclohexyl | H | | | D |
| | (3')-Me-Ph | H | H | CH2-(2')-pyr | (rac)-cyclohexyl | H | | | D |
| | (2')-MeO-Ph | H | H | CH2-(2')-pyr | (rac)-cyclohexyl | H | | | D |
| | (4')-acetyl-Ph | H | H | CH2-(2')-pyr | (rac)-cyclohexyl | H | | | D |
| | (2')-CF3-Ph | H | H | CH2-(2')-pyr | (rac)-cyclohexyl | H | | | D |
| | 3-thienyl | H | H | CH2-(2')-pyr | (rac)-cyclohexyl | H | | | D |
| | (2')-acetyl-Ph | H | H | CH2-(2')-pyr | (rac)-cyclohexyl | H | | | |
| | (2')-Cl-Ph | H | H | CH2-(2')-pyr | (rac)-cyclohexyl | H | | | D |
| | 2-benzo[b]-thienyl | H | H | CH2-(2')-pyr | (rac)-cyclohexyl | H | | | D |
| | (2')-[(5)-Cl]-thienyl | H | H | CH2-(2')-pyr | (rac)-cyclohexyl | H | | | D |
| | (2')-Br-Ph | H | H | CH2-(2')-pyr | (rac)-cyclohexyl | H | | | D |
| | (3')-(CF3-O)-Ph | H | H | CH2-(2')-pyr | (rac)-cyclohexyl | H | | | D |
| | (4')-vinyl-Ph | H | H | CH2-(2')-pyr | (rac)-cyclohexyl | H | | | D |
| | (2')-[(5)-acetyl]-thienyl | H | H | CH2-(2')-pyr | (rac)-cyclohexyl | H | | | D |
| | (4')-(CF3-O)-Ph | H | H | CH2-(2')-pyr | (rac)-cyclohexyl | H | | | D |
| | (3',5')-diF-Ph | H | H | CH2-(2')-pyr | (rac)-cyclohexyl | H | | | D |

-continued

| Compounds | X | Y | R1 | R2 | R3 | R4 | NMR | LCMS/α_D | Synthetic route |
|---|---|---|---|---|---|---|---|---|---|
| | (4')-ethoxy-Ph | H | H | CH2-(2')-pyr | (rac)-cyclohexyl | H | | | D |
| | (4')-Me—S-Ph | H | H | CH2-(2')-pyr | (rac)-cyclohexyl | H | | | D |
| | (2',5')-diMeO-Ph | H | H | CH2-(2')-pyr | (rac)-cyclohexyl | H | | | D |
| | n-hexyl | H | H | CH2-(2')-pyr | (rac)-cyclohexyl | H | | | D |
| | (3')-thia-naphthyl | H | H | CH2-(2')-pyr | (rac)-cyclohexyl | H | | | D |
| | (3')-O—Me-Ph | H | H | CH2-(2')-pyr | (rac)-cyclohexyl | H | | | D |
| | (4')-biphenyl | H | H | CH2-(2')-pyr | (rac)-cyclohexyl | H | | | D |
| | (4')-phenoxy-Ph | H | H | CH2-(2')-pyr | (rac)-cyclohexyl | H | | | D |
| | (2')-[(5)-Me]-Ph | H | H | CH2-(2')-pyr | (rac)-cyclohexyl | H | | | D |
| | 1-naphthyl | H | H | CH2-(2')-pyr | (rac)-cyclohexyl | H | | | D |
| | Trans-1-hexen-1-yl | H | H | CH2-(2')-pyr | (rac)-cyclohexyl | H | | | D |
| | (3')-OH-Ph | H | H | CH2-(2')-pyr | (rac)-cyclohexyl | H | | | D |
| | (4')-OH-Ph | H | H | CH2-(2')-pyr | (rac)-cyclohexyl | H | (DMSO-D6) 1.4 (m, 18H) 4.3 (m, 4H) 6.8 (m, 2H) 7.1 (dd, J = 7.9, 4.7 Hz, 1H) 7.2 (m, 2H) 7.5 (m, 2H) 7.7 (m, 1H) 7.7 (s, 1H) 8.2 (dd, J = 7.8, 1.5 Hz, 1H) 8.3 (dd, J = 4.6, 1.3 Hz, 1H) 8.4 (t, J = 5.8 Hz, 1H) 8.5 (m, 1H) 9.4 (s, 1H) | ES+ 497.4 | D |
| | (2',5')-diMe-Ph | H | H | CH2-(2')-pyr | (rac)-cyclohexyl | H | | | D |
| | (3,4)-methylene-dioxy-Ph | H | H | CH2-(2')-pyr | (rac)-cyclohexyl | H | | | D |
| | (3',4')-diF-Ph | H | H | CH2-(2')-pyr | (rac)-cyclohexyl | H | | | D |
| | (3')-acetyl-Ph | H | H | CH2-(2')-pyr | (rac)-cyclohexyl | H | | | D |
| | (4')-ethylthio-Ph | H | H | CH2-(2')-pyr | (rac)-cyclohexyl | H | | | D |
| | (3')-cyano-Ph | H | H | CH2-(2')-pyr | (rac)-cyclohexyl | H | | | D |
| | Trans-2-(4-fluoro-phenyl)Vinyl | H | H | CH2-(2')-pyr | (rac)-cyclohexyl | H | | | D |
| | (2')-iPr-O-Ph | H | H | CH2-(2')-pyr | (rac)-cyclohexyl | H | | | D |
| | (2',6')-diMe-Ph | H | H | CH2-(2')-pyr | (rac)-cyclohexyl | H | | | D |
| | (3',4')-diF-Ph | H | H | CH2-(2')-pyr | (rac)-cyclohexyl | H | | | D |
| | (2',5')-diF-Ph | H | H | CH2-(2')-pyr | (rac)-cyclohexyl | H | | | D |
| | [(4')-F-(3')-Me]-Ph | H | H | CH2-(2')-pyr | (rac)-cyclohexyl | H | | | D |
| | (3')-benzyl-oxy-Ph | H | H | CH2-(2')-pyr | (rac)-cyclohexyl | H | | | D |
| | (2',6')-diMeO-Ph | H | H | CH2-(2')-pyr | (rac)-cyclohexyl | H | | | D |
| | (2',3')-diMe-Ph | H | H | CH2-(2')-pyr | (rac)-cyclohexyl | H | | | D |
| | (2',4')-diF-Ph | H | H | CH2-(2')-pyr | (rac)-cyclohexyl | H | | | D |
| | (2')-Et-Ph | H | H | CH2-(2')-pyr | (rac)-cyclohexyl | H | | | D |
| | [(5')-F-(3')-MeOH]-Ph | H | H | CH2-(2')-pyr | (rac)-cyclohexyl | H | | | D |
| | [(5')-Cl-(2')-MeO]-Ph | H | H | CH2-(2')-pyr | (rac)-cyclohexyl | H | | | D |

-continued

| Compounds X | Y | R1 | R2 | R3 | R4 | NMR | LCMS/$\alpha_D$ | Synthetic route |
|---|---|---|---|---|---|---|---|---|
| [(5')-Cl-(2')-EtO]-Ph | H | H | CH2-(2')-pyr | (rac)-cyclohexyl | H | | | D |
| (2')-butoxy-Ph | H | H | CH2-(2')-pyr | (rac)-cyclohexyl | H | | | D |
| (3',5')-diMe-Ph | H | H | CH2-(2')-pyr | (rac)-cyclohexyl | H | | | D |
| (3')-propoxy-Ph | H | H | CH2-(2')-pyr | (rac)-cyclohexyl | H | | | D |
| (3')-butoxy-Ph | H | H | CH2-(2')-pyr | (rac)-cyclohexyl | H | | | D |
| (2',4')-diMeO-Ph | H | H | CH2-(2')-pyr | (rac)-cyclohexyl | H | | | D |
| (3')-ethoxy-Ph | H | H | CH2-(2')-pyr | (rac)-cyclohexyl | H | | | D |
| (2')-ethoxy-Ph | H | H | CH2-(2')-pyr | (rac)-cyclohexyl | H | | | D |
| (3',5')-bisCF3-Ph | H | H | CH2-(2')-pyr | (rac)-cyclohexyl | H | | | D |
| (2',3')-diF-Ph | H | H | CH2-(2')-pyr | (rac)-cyclohexyl | H | | | D |
| (4')-MeSO2-Ph | H | H | CH2-(2')-pyr | (rac)-cyclohexyl | H | | | D |
| (4')-[(N,N-diMeNH)]-Ph | H | H | CH2-(2')-pyr | (rac)-cyclohexyl | H | | | D |
| (2')-nitro-Ph | H | H | CH2-(2')-pyr | (rac)-cyclohexyl | H | | | D |
| 1H-pyrazolyl | H | H | CH2-(2')-pyr | (rac)-cyclohexyl | H | | | D |
| Trans-beta-styrenyl | H | H | CH2-(2')-pyr | (rac)-cyclohexyl | H | | | D |
| (3')-CH3COO-Ph | H | H | CH2-(2')-pyr | (rac)-cyclohexyl | H | | | D |
| (4')-[tert-but-O—CO—O]-Ph | H | H | CH2-(2')-pyr | (rac)-cyclohexyl | H | | | D |
| (4')-[tert-butyldimethylsilyl-O]-Ph | H | H | CH2-(2')-pyr | (rac)-cyclohexyl | H | | | D |
| Ph | H | H | 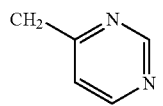 | Ph | H | (DMSO-D6) 1.4 (m, 18H) 4.3 (m, 2H) 4.4 (d, J = 5.7 Hz, 2H) 7.2 (dd, J = 7.8, 4.8 Hz, 1H) 7.2 (t, J = 7.3 Hz, 1H) 7.4 (t, J = 7.6 Hz, 2H) 7.7 (d, J = 7.1 Hz, 2H) 7.9 (s, 1H) 8.3 (m, 2H) 8.5 (m, 4H) | ES+ 482.4 | A + EDCl |
| Ph | H | H | 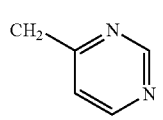 | (rac)-cyclohexyl | H | (DMSO-D6) 1.2 (m, 18H) 4.2 (m, 4H) 7.2 (m, 3H) 7.4 (t, J = 7.6 Hz, 2H) 7.7 (d, J = 7.1 Hz, 2H) 8.0 (s, 1H) 8.3 (m, 2H) 8.5 (t, J = 5.8 Hz, 1H) 8.7 (d, J = 5.1 Hz, 1H) 9.1 (d, J = 1.1 Hz, 1H) | ES+ 482.5 | A + EDCl |

As other compounds according to the invention for which n=3, mention may be made of:

| X | Y | R1 | R2 | R3 | R4 | Z1 | Z2 | NMR | MS | Synthetic route |
|---|---|---|---|---|---|---|---|---|---|---|
| Ph | H | H | CH2-(2')-pyr | (rac)cyclohexyl | H | H | —OMe | (CHLOROFORM-D) 1.4 (m, 18H) 4.0 (s, 3H) 4.2 (m, 2H) 4.5 (d, J = 4.8 Hz, 2H) 6.6 (m, 1H) 6.7 (m, 1H) 7.2 (m, 4H) 7.4 (m, 2H) 7.6 (m, 3H) 8.1 (m, 1H) 8.5 (d, J = 5.0 Hz, 1H) | ES+ 511.5 | A |
| Ph | H | H | CH2-(4')-pyr | (rac)cyclohexyl | H | H | —OMe | (CHLOROFORM-D) 1.5 (m, 18H) 4.0 (s, 3H) 4.3 (m, 4H) 5.7 (t, J = 5.7 Hz, 1H) 6.6 (dd, J = 8.6, 1.9 Hz, 1H) 7.1 (d, J = 5.2 Hz, 2H) 7.2 (m, 2H) 7.4 (m, 2H) 7.6 (m, 2H) 8.1 (dd, J = 8.6, 1.9 Hz, 1H) 8.5 (d, J = 4.4 Hz, 2H) | ES+ 511.5 | A |
| H | H | H | CH2-(2')-pyr | (rac)cyclohexyl | H | —NMe2 | H | (CHLOROFORM-D) 1.2 (m, 18H) 3.3 (s, 6H) 4.2 (m, 2H) 4.5 (m, 2H) 6.2 (d, J = 5.9 Hz, 1H) 6.6 (d, J = 3.4 Hz, 1H) 6.9 (m, 1H) 7.2 (m, 3H) 7.6 (m, 1H) 8.0 (d, J = 5.9 Hz, 1H) 8.5 (d, J = 3.4 Hz, 1H) | ES+ 448.5 | A |
| H | H | H | CH2-(4')-pyr | (rac)cyclohexyl | H | —NMe2 | H | (CHLOROFORM-D) 1.4 (m, 18H) 3.3 (s, 6H) 4.3 (m, 4H) 6.2 (d, J = 6.3 Hz, 1H) 6.6 (d, J = 3.6 Hz, 1H) 6.9 (d, J = 3.6 Hz, 1H) 7.2 (m, 2H) 7.9 (d, J = 6.3 Hz, 1H) 8.5 (m, 3H) | ES+ 448.5 | A |
| H | H | H | CH2-(2')-pyr | (rac)cyclohexyl | H | —NMePh | H | (CHLOROFORM-D) 1.4 (m, 18H) 3.5 (s, 3H) 4.1 (m, 2H) 4.5 (d, J = 5.0 Hz, 2H) 5.2 (d, J = 3.6 Hz, 1H) 6.5 (d, J = 5.5 Hz, 1H) 6.7 (d, J = 3.6 Hz, 2H) 7.2 (m, 5H) 7.4 (m, 2H) 7.6 (m, 1H) 8.1 (d, J = 5.5 Hz, 1H) 8.5 (dd, J = 5.0, 0.8 Hz, J = 5.0, 0.8 Hz, | ES+ 510.4 | A |
| H | H | H | CH2-(4')-pyr | (rac)cyclohexyl | H | —NMePh | H | (CHLOROFORM-D) 1.2 (m, 18H) 3.5 (s, 3H) 4.1 (m, 2H) 4.4 (m, 2H) 5.2 (d, J = 3.6 Hz, 1H) 6.5 (d, J = 5.7 Hz, 1H) 6.7 (d, J = 3.6 Hz, 1H) 7.2 (m, 6H) 7.4 (d, J = 7.8 Hz, 2H) 8.0 (d, J = 5.7 Hz, 1H) 8.5 (m, 2H) | ES+ 510.4 | A |

Other compounds in accordance with the invention containing a C6 chain, cycloheptyl (i.e. with n=3 and R3=cycloheptyl and Z1=Z2=H):

| X | Y | R1 | R2 | R3 | R4 | Analytical data (ES+) | Synthetic routes |
|---|---|---|---|---|---|---|---|
| Ph | H | H | CH(Me)Ph | (rac)-cycloheptyl | H | ES+ = 508.4 | A/acid chloride |
| Ph | H | H | CH(Ph)Ph | (rac)-cycloheptyl | H | ES+ = 570.4 | A/acid chloride |
| Ph | H | H | (4')-piperidinobenzyl | (rac)-cycloheptyl | H | ES+ = 577.5 | A/acid chloride |
| Ph | H | H | CH2-(4')-S(O2)NH2-Ph | (rac)-cycloheptyl | H | ES+ = 573.4 | A/acid chloride |
| Ph | H | H | CH2-(3')-pyr | (rac)-cycloheptyl | H | ES+ = 495.4 | A/acid chloride |
| Ph | H | H | CH2-(3')-Me-Ph | (rac)-cycloheptyl | H | ES+ = 508.4 | A/acid chloride |
| Ph | H | H | CH2-(4')-Cl-Ph | (rac)-cycloheptyl | H | ES+ = 528.4/530.4 | A/acid chloride |
| Ph | H | H | CH2-(2')-Cl-Ph | (rac)-cycloheptyl | H | ES+ = 528.4/530.4 | A/acid chloride |
| Ph | H | H | CH2-(2')-NO2 | (rac)-cycloheptyl | H | ES+ = 539.4 | A/acid chloride |
| Ph | H | H | (4')-piperidinoEtOCO | (rac)-cycloheptyl | H | ES+ = 559.5 | A/acid chloride |
| Ph | H | H | CH2-(2',4')-Cl-Ph | (rac)-cycloheptyl | H | ES+ = 562.3/564.3/566.3 | A/acid chloride |
| Ph | H | H | CH2-benzo[b]cyclohexyl | (rac)-cycloheptyl | H | ES+ = 534.4 | A/acid chloride |
| Ph | H | H | CH2-(4')-NO2 | (rac)-cycloheptyl | H | ES+ = 539.4 | A/acid chloride |
| Ph | H | H | CH2-(2')-CF3-Ph | (rac)-cycloheptyl | H | ES+ = 562.4 | A/acid chloride |
| Ph | H | H | CH2-(3')-CF3-Ph | (rac)-cycloheptyl | H | ES+ = 562.4 | A/acid chloride |
| Ph | H | H | CH2-(4')-CF3-O-Ph | (rac)-cycloheptyl | H | ES+ = 578.4 | A/acid chloride |
| Ph | H | H | CH(CH2OH)Ph | (rac)-cycloheptyl | H | ES+ = 524.4 | A/acid chloride |
| Ph | H | H | CH2-(4')-MeO-Ph | (rac)-cycloheptyl | H | ES+ = 524.4 | A/acid chloride |

-continued

| X | Y | R1 | R2 | R3 | R4 | Analytical data (ES+) | Synthetic routes |
|---|---|---|---|---|---|---|---|
| Ph | H | H | CH2-(3,4-methylenedioxybenzene) | (rac)-cycloheptyl | H | ES+ = 538.4 | A/acid chloride |
| Ph | H | H | CH2-(4')-COOH-Ph | (rac)-cycloheptyl | H | ES+ = 538.4 | A/acid chloride |
| Ph | H | H | benzo[b]cyclopentyl | (rac)-cycloheptyl | H | ES+ = 520.4 | A/acid chloride |
| Ph | H | H | CH2-(2')-Br-Ph | (rac)-cycloheptyl | H | ES+ = 572.3/574.3 | A/acid chloride |
| Ph | H | H | CH2-(3')-Cl-Ph | (rac)-cycloheptyl | H | ES+ = 528.4/530.4 | A/acid chloride |
| Ph | H | H | CH2-(3')-F-Ph | (rac)-cycloheptyl | H | ES+ = 512.4 | A/acid chloride |
| Ph | H | H | CH2-(4')-F-Ph | (rac)-cycloheptyl | H | ES+ = 512.4 | A/acid chloride |
| Ph | H | H | CH2-(2')-Me-Ph | (rac)-cycloheptyl | H | ES+ = 508.4 | A/acid chloride |
| Ph | H | H | CH2-(4')-Me-Ph | (rac)-cycloheptyl | H | ES+ = 508.4 | A/acid chloride |
| Ph | H | H | (CH2)2-(2')-pyr | (rac)-cycloheptyl | H | ES+ = 509.4 | A/acid chloride |
| Ph | H | H | CH2-[(3')-MeO-(4')-OH]-Ph | (rac)-cycloheptyl | H | ES+ = 540.4 | A/acid chloride |
| Ph | H | H | CH2-(4')-CF3-Ph | (rac)-cycloheptyl | H | ES+ = 562.4 | A/acid chloride |
| Ph | H | H | CH2-(3')-I-Ph | (rac)-cycloheptyl | H | ES+ = 620.3 | A/acid chloride |
| Ph | H | H | CH2-[(2')-Me]-furan-5-yl | (rac)-cycloheptyl | H | ES+ = 498.4 | A/acid chloride |
| Ph | H | H | CH2-(3',5')-F-Ph | (rac)-cycloheptyl | H | ES+ = 530.4 | A/acid chloride |
| Ph | H | H | CH2-(2',4')-MeO-Ph | (rac)-cycloheptyl | H | ES+ = 554.4 | A/acid chloride |
| Ph | H | H | CH2-(3',5')-MeO-Ph | (rac)-cycloheptyl | H | ES+ = 554.4 | A/acid chloride |
| Ph | H | H | CH2-allyl | (rac)-cycloheptyl | H | ES+ = 444.4 | A/acid chloride |
| Ph | H | H | CH2-(2')-furanyl | (rac)-cycloheptyl | H | ES+ = 484.4 | A/acid chloride |
| Ph | H | H | CH2-(2')-benzochromanyl | (rac)-cycloheptyl | H | ES+ = 550.4 | A/acid chloride |
| Ph | H | H | CH2-(2')-thienyl | (rac)-cycloheptyl | H | ES+ = 500.4 | A/acid chloride |
| Ph | H | H | CH2-(2',3')-F-Ph | (rac)-cycloheptyl | H | ES+ = 530.3 | A/acid chloride |
| Ph | H | H | CH2-(2')-NO2-Ph | (rac)-cycloheptyl | H | ES+ = 539.3 | A/acid chloride |
| Ph | H | H | CH2-(2')-CF3-O-Ph | (rac)-cycloheptyl | H | ES+ = 578.4 | A/acid chloride |
| Ph | H | H | CH2-(3')-CF3-O-Ph | (rac)-cycloheptyl | H | ES+ = 578.4 | A/acid chloride |
| Ph | H | H | CH2-[(2')-F-(5')-CF3]-Ph | (rac)-cycloheptyl | H | ES+ = 580.4 | A/acid chloride |
| Ph | H | H | CH2-[(2')-CF3-(4')-F]-Ph | (rac)-cycloheptyl | H | ES+ = 580.4 | A/acid chloride |
| Ph | H | H | CH2-[(3')-CF3-(4')-F]-Ph | (rac)-cycloheptyl | H | ES+ = 580.4 | A/acid chloride |
| Ph | H | H | CH2-[(3')-Cl-(4')-CF3]-Ph | (rac)-cycloheptyl | H | ES+ = 596.4/598.4 with 1 Cl | A/acid chloride |
| Ph | H | H | CH2-(2',4')-CF3-Ph | (rac)-cycloheptyl | H | ES+ = 630.1 | A/acid chloride |
| Ph | H | H | CH2-(2')-MeO-Ph | (rac)-cycloheptyl | H | ES+ = 524.4 | A/acid chloride |
| Ph | H | H | CH2-(3')-MeO-Ph | (rac)-cycloheptyl | H | ES+ = 524.4 | A/acid chloride |
| Ph | H | H | CH2-[(2')-F-(4')-F]-Ph | (rac)-cycloheptyl | H | ES+ = 530.4 | A/acid chloride |
| Ph | H | H | CH2-[(2')-F-(5')-F]-Ph | (rac)-cycloheptyl | H | ES+ = 530.4 | A/acid chloride |
| Ph | H | H | CH2-[(2')-F-(6')-F]-Ph | (rac)-cycloheptyl | H | ES+ = 530.4 | A/acid chloride |
| Ph | H | H | CH2-(3',4')-F-Ph | (rac)-cycloheptyl | H | ES+ = 530.4 | A/acid chloride |
| Ph | H | H | CH2-naphthyl | (rac)-cycloheptyl | H | ES+ = 544.4 | A/acid chloride |
| Ph | H | H | CH2-[(2',3')-MeO]-Ph | (rac)-cycloheptyl | H | ES+ = 554.5 | A/acid chloride |
| Ph | H | H | CH2-(3',4')-Cl-Ph | (rac)-cycloheptyl | H | ES+ = 562.3/564.3/566.3 | A/acid chloride |
| Ph | H | H | CH2-[(3',4',5')-MeO]-Ph | (rac)-cycloheptyl | H | ES+ = 584.5 | A/acid chloride |
| Ph | H | H | CH2-(3')-Br-Ph | (rac)-cycloheptyl | H | ES+ = 572.3/574.3 | A/acid chloride |
| Ph | H | H | CH2-(4')-Br-Ph | (rac)-cycloheptyl | H | ES+ = 572.3/574.3 | A/acid chloride |
| Ph | H | H | CH2-vinyl | (rac)-cycloheptyl | H | ES+ = 458.4 | A/acid chloride |
| Ph | H | H | CH2-[(2')-F-(5')-Br]-Ph | (rac)-cycloheptyl | H | ES+ = 590.3/592.3 | A/acid chloride |
| Ph | H | H | CH2-(2')-EtO-Ph | (rac)-cycloheptyl | H | ES+ = 538.4 | A/acid chloride |
| Ph | H | H | CH2-[(3',4')-MeO]-Ph | (rac)-cycloheptyl | H | ES+ = 554.4 | A/acid chloride |
| Ph | H | H | CH2-[(3')-F-(5')-CF3]-Ph | (rac)-cycloheptyl | H | ES+ = 580.4 | A/acid chloride |
| Ph | H | H | CH2-(4')-(CH3)2N-Ph | (rac)-cycloheptyl | H | ES+ = 537.4 | A/acid chloride |
| Ph | H | H | CH2-(3')-Me-thien-2-yl | (rac)-cycloheptyl | H | ES+ = 514.4 | A/acid chloride |
| Ph | H | H | CH2-[(2')-Cl-(6')-Me]-Ph | (rac)-cycloheptyl | H | ES+ = 542.4/544.4 | A/acid chloride |
| Ph | H | H | CH2-[(2')-Cl-(4')-F]-Ph | (rac)-cycloheptyl | H | ES+ = 546.4/548.4 | A/acid chloride |
| Ph | H | H | CH2-[(3')-Cl-(4')-F]-Ph | (rac)-cycloheptyl | H | ES+ = 546.4/548.4 | A/acid chloride |
| Ph | H | H | CH2-[(2',6')-MeO]-Ph | (rac)-cycloheptyl | H | ES+ = 554.5 | A/acid chloride |
| Ph | H | H | CH2-[(2')-Cl-(3')-Cl]-Ph | (rac)-cycloheptyl | H | ES+ = 562.3/564.3/566.3 | A/acid chloride |
| Ph | H | H | CH2-[(2')-Cl-(4')-Cl]-Ph | (rac)-cycloheptyl | H | ES+ = 562.3/564.3/566.3 | A/acid chloride |
| Ph | H | H | CH2-[(3')-Cl-(5')-Cl]-Ph | (rac)-cycloheptyl | H | ES+ = 562.3/564.3/566.3 | A/acid chloride |
| Ph | H | H | CH2-[(6')-Me-(2',5')-Cl]-Ph | (rac)-cycloheptyl | H | ES+ = 576.4/578.4/580.4 | A/acid chloride |
| Ph | H | H | CH2-(4')-I-Ph | (rac)-cycloheptyl | H | ES+ = 620.3 | A/acid chloride |

The preferred compounds of the formula (I) containing a C7 chain (in which n=4 and R4=H) are indicated in the following table, in which Z denotes one of the four methylenes of —(V)n- or an oxygen atom (if the hydrocarbon chain of the general formula (I), represented by —(V)n-, in other words —(CH$_2$)n-, is interrupted by oxygen), and in which Z1=Z2=H:

TABLE 3

| X | Y | Z | R1 | R2 | R3 | NMR | ES+ | Acid/amide synthetic route |
|---|---|---|---|---|---|---|---|---|
| Ph | H | CH2 | H | CH2Ph | (rac)-cyclopentyl | (DMSO-d6): 0.62-2.17 (18H, m); 4.06-4.52 (4H, m); 7.01-7.61 (9H, m); 7.61-7.89 (2H, m); 7.95 (1H, m); 8.15-8.58 (3H, m). | | A/EDCl |
| Ph | H | CH2 | H | CH2-(2')-pyr | (rac)-cyclopentyl | (DMSO-d6): 0.88-2.10 (18H, m); 4.22-4.38 (4H, m); 7.13-7.29 (4H, m); 7.39-7.48 (2H, m); 7.67-7.76 (3H, m); 7.96 (1H, s), 8.26-8.49 (4H, m). | | A/EDCl |
| Ph | H | CH2 | H | CH2-(4')-pyr | (rac)-cyclopentyl | (DMSO-d6): 0.89-2.08 (18H, m); 4.20-4.34 (4H, m); 7.14-7.30 (4H, m); 7.38-7.49 (2H, m); 7.66-7.76 (2H, m); 7.96 (1H, s); 8.25-8.35 (2H, m); 8.39-8.52 (3H, m). | | A/EDCl |
| Ph | H | CH2 | H | CH2-(4')-SO2MePh | (rac)-cyclopentyl | (DMSO-d6): 0.90-2.10 (18H, m); 3.14 (3H, s); 4.22-4.39 (4H, m); 7.12-7.31 (2H, m); 7.39-7.53 (4H, m); 7.67-7.77 (2H, m); 7.82-7.92 (2H, m); 7.96 (1H, s); 8.26-8.49 (3H, m). | | A/EDCl |
| Ph | H | CH2 | H | CH2(6')-Me-(2')-pyr | (rac)-cyclopentyl | (DMSO-d6): 0.91-2.16 (18H, m); 2.39 (3H, s); 4.16-4.49 (4H, m); 6.86-7.35 (4H, m); 7.35-7.84 (5H, m); 7.95 (1H, s); 8.15-8.54 (3H, m). | | A/EDCl |
| Ph | H | O | H | CH2Ph | (rac)-cyclopentyl | (DMSO-d6): 0.78-2.14 (12H, m); 3.17-3.37 (2H, m); 3.61-3.77 (2H, m); 4.13-4.24 (2H, m); 4.35-4.46 (2H, m); 7.10-7.31 (7H, m); 7.35-7.47 (2H, m); 7.62-7.73 (2H, m); 7.93 (1H, s); 8.05-8.33 (3H, m). | | A/EDCl |
| Ph | H | O | H | CH2-(4')-SO2MePh | (rac)-cyclopentyl | (DMSO-d6): 0.86-2.11 (10H, m); 3.09-3.39 (2H, m); 3.66-3.81 (2H, m); 4.23-4.48 (4H, m); 7.14-7.28 (2H, m); 7.37-7.48 (4H, m); 7.64-7.72 (2H, m); 7.79-7.87 (2H, m); 7.95 (1H, s); 8.19-8.32 (3H, m). | | A/EDCl |
| Ph | H | O | H | CH2-(2')-pyr | (rac)-cyclopentyl | (DMSO-d6): 0.71-2.21 (12H, m); 3.22-3.41 (2H, m); 3.65-3.81 (2H, m); 4.22-4.50 (4H, m); 7.12-7.30 (4H, m); 7.35-7.48 (2H, m); 7.62-7.75 (3H, m); 7.95 (1H, s); 8.16-8.47 (4H, m). | | A/EDCl |
| Ph | H | O | H | CH2-(4')-pyr | (rac)-cyclopentyl | (DMSO-d6): 0.80-2.158 (12H, m); 3.22-3.40 (2H, m); 3.67-3.82 (2H, m); 4.14-4.30 (2H, m); 4.37-4.55 (2H, m); 7.14-7.30 (4H, m); 7.39-7.48 (2H, m); 7.65-7.74 (2H, m); 7.95 (1H, s); 8.18-8.50 (5H, m). | | A/EDCl |
| Ph | H | CH2 | H | CH2-(2')-pyr | (rac)-cyclohexyl | (DMSO-d6): 0.63-2.25 (20H, m); 4.08-4.66 (4H, m); 7.02-8.18 (10H, m); 8.18-8.71 (4H, m). | | A/EDCl |
| Ph | H | CH2 | H | CH2-(4')-pyr | (rac)-cyclohexyl | (DMSO-d6): 0.60-2.21 (20H, m); 4.06-4.60 (4H, m); 7.03-7.63 (6H, m); 7.63-7.89 (2H, m); 7.95 (1H, s); 8.18-8.75 (5H, m). | | A/EDCl |
| iPr | H | CH2 | H | CH2-(3')-pyr | (rac)-cyclopentyl | (CDCl$_3$): 0.54-2.17 (24H, m); 3.04-3.27 (1H, m); 3.88-4.66 (4H, m); 6.50-7.42 (4H, m); 7.43-8.32 (3H, m); 8.32-8.71 (2H, m). | | A/EDCl |
| iPr | H | CH2 | H | CH2-(2')-pyr | (rac)-cyclopentyl | (CDCl$_3$): 0.59-2.20 (24H, m); 2.97-3.34 (1H, m); 3.96-4.72 (4H, m); 6.64-7.44 (5H, m); 7.47-8.67 (4H, m). | | A/EDCl |
| iPr | H | CH2 | H | CH2-(4')-pyr | (rac)-cyclopentyl | (CDCl$_3$): 0.68-2.16 (24H, m); 2.97-3.33 (1H, m); 3.90-4.65 (4H, m); 6.62-7.38 (5H, m); 7.65-8.34 (2H, m); 8.34-8.67 (2H, m). | | A/EDCl |

TABLE 3-continued

| X | Y | Z | R1 | R2 | R3 | NMR | ES+ | Acid/amide synthetic route |
|---|---|---|---|---|---|---|---|---|
| Ph | H | CH2 | H | CH2-(4')-pyr | (rac)-cycloheptyl | (DMSO-d6): 0.60-2.13 (22H, m); 4.15-4.40 (4H, m); 7.10-7.80 (8H, m); 7.97 (1H, s); 8.20-8.55 (5H, m). | | A/EDCl |
| Ph | H | CH2 | H | CH2-(2')-pyr | (rac)-cycloheptyl | (DMSO-d6): 0.60-2.13 (22H, m); 4.11-4.50 (4H, m); 7.08-7.82 (9H, m); 7.96 (1H, s); 8.20-8.60 (4H, m). | | A/EDCl |
| Ph | H | CH2 | H | CH2-pyrimidinyl | (rac)-cyclopentyl | (DMSO-D6) 1.3 (m, 15H) 1.8 (m, 4H) 2.0 (m, 1H) 4.3 (m, 4H) 7.2 (dd, J = 7.5, 5.1 Hz, 1H) 7.3 (t, J = 7.3 Hz, 1H) 7.3 (dd, J = 5.2, 1.2 Hz, 1H) 7.4 (t, J = 7.7 Hz, 2H) 7.7 (m, 2H) 8.0 (s, 1H) 8.3 (m, 2H) 8.5 (t, J = 5.9 Hz, 1H) 8.7 (d, J = 5.2 Hz, 1H) 9.1 (d, J = 1.1 Hz, 1H) | ES+ 482.5 | A/EDCl |
| Ph | H | CH2 | H | CH2-(2')-pyrazinyl | (rac)-cyclopentyl | | | A/EDCl |
| Ph | H | Ph | H | CH2-(2H)-pyrazin-5-yl | (rac)-cyclopentyl | | | A/EDCl |
| (3')-Pyr | H | CH2 | H | CH2-(2')-pyr | (rac)-cyclopentyl | (DMSO-D6) 1.3 (m, 17H) 2.0 (m, 1H) 4.2 (m, 4H) 7.3 (m, 4H) 7.7 (m, 1H) 8.1 (m, 2H) 8.5 (m, 5H) 9.0 (s, 1H) | | A/EDCl then D |
| (4')-Pyr | H | CH2 | H | CH2-(2')-pyr | (rac)-cyclopentyl | (DMSO-D6) 1.3 (m, 13H) 1.8 (m, 4H) 2.0 (m, 1H) 4.3 (m, 4H) 7.2 (m, 3H) 7.6 (m, 4H) 8.4 (m, 4H) 8.6 (d, J = 6.0 Hz, 2H) | | A/EDCl then D |
| (4')-Pyr | H | CH2 | H | CH2-(2')-pyr | (rac)-cyclohexyl | | | |
| (2')-Pyr | H | CH2 | H | CH2-(2')-pyr | (rac)-cyclohexyl | | | |
| (3')-Pyr | H | CH2 | HS | CH2-(2')-pyr | (rac)-cyclohexyl | | | |
| Br | H | CH2 | H | CH2-(2')-pyr | (rac)-cyclopentyl | (DMSO-D6) 1.3 (m, 13H) 1.8 (s, 4H) 2.0 (m, 1H) 4.2 (t, J = 7.0 Hz, 2H) 4.3 (d, J = 5.9 Hz, 2H) 7.2 (m, 3H) 7.7 (m, 1H) 7.8 (m, 2H) 8.4 (m, 3H) | ES+ 483.2/ 485.2 | A/EDCl |
| (4')-OH-Ph | H | CH2 | H | CH2-(2')-pyr | (rac)-cyclopentyl | (DMSO-D6) 1.4 (m, 13H) 1.8 (m, 4H) 2.0 (m, 1H) 4.2 (t, J = 6.9 Hz, 2H) 4.3 (d, J = 5.9 Hz, 2H) 6.8 (d, J = 8.6 Hz, 2H) 7.2 (m, 3H) 7.5 (d, J = 8.6 Hz, 2H) 7.7 (m, 2H) 8.2 (m, 2H) 8.4 (m, 2H) 9.4 (s, 1H) | | A/EDCl then D |
| (3')-[MeO(CH2)2O]Ph | H | CH2 | H | CH2-(2')-pyr | (rac)-cyclopentyl | | ES+ 555.5 (M + H+) 278.6 (M + 2H+) ES− 599.6 (M + HCOO−) | route D + modification R2 |
| Ph | H | CH2 | H | CH2-(5')-triazinyl | (rac)-cyclopentyl | | | |
| Ph | H | CH2 | H | CH2-(5')-[(4')-MeO-Ph-CH2]-triazolyl | (rac)-cyclopentyl | (chloroform-d) 1.5 (m, 19H) 2.0 (m, 1H) 3.7 (s, 3H) 4.3 (m, J = 41.2 Hz, 4H) 5.3 (s, 2H) 6.9 (m, 2H) 7.2 (m, 4H) 7.4 (m, 2H) 7.7 (m, 2H) 7.8 (m, J = 4.8 Hz, 1H) 7.9 (m, J = 4.4 Hz, 1H) 8.3 (m, J = 5.2, 3.9 Hz, 2H) 8.5 (m, 1H) | ES+ 605.4 | EDCl |
| (2')-pyr | H | CH2 | H | CH2-(2')-pyr | (rac)-cyclopentyl | (DMSO-D6) 1.4 (m, 13H) 1.9 (m, 5H) 4.3 (m, 4H) 7.2 (m, 4H) 7.8 (m, 3H) 8.4 (m, 4H) 8.6 (d, J = 4.0 Hz, 1H) 8.8 (d, J = 7.8 Hz, 1H) | ES+ 482.5 | EDCl then D |
| (4')-OH-Ph | H | CH2 | H | CH2-(2')-pyr | (rac)-cyclopentyl | | | |
| (4')-[MeO—(CH2)2-O]-Ph | H | CH2 | H | CH2-(2')-pyr | (rac)-cyclopentyl | (DMSO-D6) 1.5 (m, 18H) 3.3 (s, 3H) 3.7 (dd, J = 5.1, 3.5 Hz, 2H) 4.1 (m, 2H) 4.3 (d, J = 6.3 Hz, 4H) 7.0 (d, J = 8.4 Hz, 2H) 7.2 (m, 3H) 7.7 (m, 2H) 7.8 (s, 1H) 8.3 (m, 3H) 8.5 (m, 1H) | ES+ 555.5 (M + H+) 278.6 (M + 2H+) | |
| (3')-OH-Ph | H | CH2 | H | CH2-(2')-pyr | (rac)-cyclopentyl | (DMSO-D6) 1.3 (m, 20H) 4.2 (m, 4H) 5.1 (s, 2H) 7.2 (m, 2H) 7.4 (m, 4H) 7.7 (m, 2H) 8.0 (m, 3H) 8.3 (m, 2H) 8.4 (t, J = 5.8 Hz, 1H) | ES+ 497.6 | A/EDCl then D |
| (4')OSiMe2tBu-Ph | H | CH2 | H | CH2-(2')-pyr | (rac)-cyclopentyl | (DMSO-D6) 0.2 (s, 6H) 1.2 (m, 18H) 1.0 (s, 9H) 4.3 (t, J = 7.0 Hz, 2H) 4.3 (d, J = 5.7 Hz, 2H) 6.9 (m, 2H) 7.2 (m, 3H) 7.6 (m, 2H) 7.7 (m, 1H) 7.9 (s, 1H) 8.3 (m, 2H) 8.4 (m, 2H) | ES+ 611.6 | A/EDCl then D |

The preferred compounds of the formula (I) containing a C8 chain (in which n=5 and R4=H, and in which Z1=Z2=H) are the following.

TABLE 4

| Examples | X | Y | R1 | R2 | R3 | Analytical data (NMR) | Acid/amide synthetic route |
|---|---|---|---|---|---|---|---|
| 487993 | Ph | H | H | CH2-(2')-pyr | (rac)-cyclopentyl | (DMSO-d6): 0.82-2.22 (20H, m); 4.10-4.58 (4H, m); 6.97-7.89 (9H, m); 7.97 (1H, s); 8.19-8.67 (4H, m). | A/EDCl |
| 487997 | Ph | H | H | CH2-(4')-pyr | (rac)-cyclopentyl | (DMSO-d6): 0.66-2.26 (20H, m); 4.09-4.57 (4H, m); 7.02-7.93 (8H, m); 7.97 (1H, s); 8.18-8.86 (5H, m). | A/EDCl |

The compounds that are even more preferred are the following compounds:
N-(4-methylsulfonyl)phenylmethyl-2-cyclohexyl-6-(3-phenyl-7-azaindol-1-yl)hexanamide
N-benzyl-2-cyclopentyl-7-(3-phenyl-7-azaindol-1-yl)hexanamide
N-(4-pyridylmethyl)-2-cycloheptyl-6-(3-phenyl-7-azaindol-1-yl)heptanamide
N-(4-pyridylmethyl)-2-cyclohexyl-6-(3-phenyl-7-azaindol-1-yl)heptanamide
N-(4-pyridylmethyl)-2-cyclohexyl-6-(3-phenyl-7-azaindol-1-yl)hexanamide
N-(4-methoxycarbonyl)phenyl-2-cycloheptyl-6-(3-phenyl-7-azaindol-1-yl)hexanamide
N-(4-methylsulfonyl)phenylmethyl-2-cycloheptyl-6-(3-phenyl-7-azaindol-1-yl)heptanamide
N-(4-n-butyl)phenylmethyl-2-cycloheptyl-6-(3-phenyl-7-azaindol-1-yl)heptanamide
N-(4-methylsulfonyl)phenylmethyl-2-cyclopentyl-6-(3-phenyl-7-azaindol-1-yl)heptanamide
N-(2-pyridylmethyl)-2-cyclohexyl-6-(3-phenyl-7-azaindol-1-yl)heptanamide
N-(2-pyridylmethyl)-2-cycloheptyl-6-(3-phenyl-7-azaindol-1-yl)heptanamide
N-(2-pyridylmethyl)-2-cyclohexyl-6-(3-phenyl-7-azaindol-1-yl)hexanamide
N-benzyl-2-cyclohexyl-6-(3-phenyl-7-azaindol-1-yl)hexanamide
N-benzyl-2-cycloheptyl-6-(3-phenyl-7-azaindol-1-yl)hexanamide
N-(4-pyridylmethyl)-2-cycloheptyl-6-(3-phenyl-7-azaindol-1-yl)hexanamide
N-(4-methylsulfonyl)phenylmethyl-2-cyclopentyl-6-(3-phenyl-7 azaindol-1-yl)hexanamide
N-(4-aminosulfonyl)phenylmethyl-2-cyclopentyl-6-(3-phenyl-7-azaindol-1-yl)hexanamide
N-(4-pyridylmethyl)-2-cyclopentyl-6-(3-phenyl-7-azaindol-1-yl)heptanamide
N-(2-pyridylmethyl)-2-cyclopentyl-6-(3-phenyl-7-azaindol-1-yl)heptanamide
N-(4-methoxycarbonyl)phenyl-2-cyclopentyl-6-(3-phenyl-7-azaindol-1-yl)hexanamide
N-(2-pyridylmethyl)-2-cyclohexyl-6-(3-pyridyl-7-azaindol-1-yl)hexanamide
N-(2-fluoro)phenylmethyl-2-cycloheptyl-6-(3-phenyl-7-azaindol-1-yl)hexanamide
N-(1-phenylethyl)-2-cycloheptyl-6-(3-phenyl-7-azaindol-1-yl)hexanamide
N-(6-fluoroquinol-2-ylmethylpiperidino)-2-cyclopentyl-6-(3-phenyl-7-azaindol-1-yl)hexanamide
N-(2-pyridyl)-2-cycloheptyl-6-(3-phenyl-7-azaindol-1-yl) hexanamide
N-(4-pyridyl)-2-cyclopentyl-6-(3-phenyl-7-azaindol-1-yl) octanamide
N-benzyl-2-cyclopentyl-6-(3-phenyl-7-azaindol-1-yl)hexanamide
N-(2-pyridyl)-2-cyclopentyl-6-(3-phenyl-7-azaindol-1-yl) octanamide
N-(4-pyridyl)-2-cyclopentyl-6-(3-phenyl-7-azaindol-1-yl) hexanamide
N-(4-methylsulfonyl)phenylmethyl-2-(2,3-cyclopentenyl)-6-(3-phenyl-7-azaindol-1-yl)hexanamide
N-(2-pyridylmethyl)-2-cyclohexyl-6-(3-phenyl-7-azaindol-1-yl)hexanamide (one enantiomer)
N-(2-pyridylmethyl)-2-cyclohexyl-6-(3-phenyl-7-azaindol-1-yl)hexanamide (the enantiomer of the above compound)
N-(2-pyridyl)-2-cyclopentyl-6-[3-(pyrid-3-yl)-7-azaindol-1-yl)heptanamide
N-(2-pyridyl)-2-cyclopentyl-6-[3-(pyrid-4-yl)-7-azaindol-1-yl)heptanamide
N-(2-hydroxy-1-phenyl)ethyl-2-cycloheptyl-6-(3-phenyl-7-azaindol-1-yl)hexanamide
N-(4-fluorophenyl)methyl-2-cycloheptyl-6-(3-phenyl-7-azaindol-1-yl)hexanamide
N-(2'-pyridino)methyl-2-cyclohexyl-6-(3-phenyl-6-methoxy-7-azaindol-1-yl)hexanamide
N-(4'-pyridino)methyl-2-cyclohexyl-6-(3-phenyl-6-methoxy-7-azaindol-1-yl)hexanamide
and also the salts, N-oxides, stereoisomers and mixtures of stereoisomers thereof.

The compounds according to the invention of the formula (I) can be prepared by amidation via EDCl or acid chloride of their precursor acid of the formula (Ia), the latter being obtained according to one of the synthetic routes A, B or C, as described in the attached Figures.

The present invention also relates to a process (referred to as synthetic route A) for the preparation of compounds of the formula (I), characterised in that it includes the steps consisting in:

(i) performing an alpha-alkylation on an ester of the formula IV:

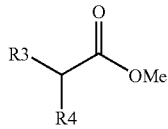
(IV)

especially in the presence of LDA/DMPU, in a suitable solvent, for instance THF, preferably with a dibromoalkyl Br—CH$_2$—[V]$_{n-1}$—CH$_2$—Br.

(ii) performing an alkylation on the azaindole of the formula (A):

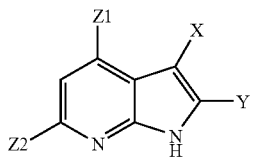
(A)

in which X, Y, Z1 and Z2 are defined as above, with the bromo ester of the formula III obtained,

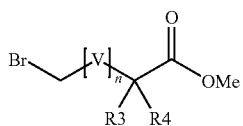
III especially in the presence of NaH in a solvent, such as DMF.

(iii) performing a hydrolysis on the ester of the formula II obtained, especially in the presence of a base, such as KOH, in a solvent, for instance and ethanol/water mixture, and

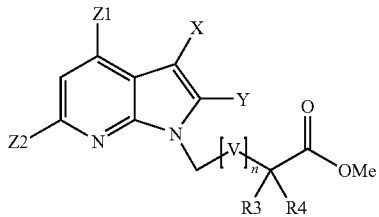
II (iv) performing an amidation on the acid of the formula Ia obtained by reaction with the corresponding amine, via EDCl or acid chloride, especially in the presence of DMAP, in a solvent, such as dichloromethane (DCM).

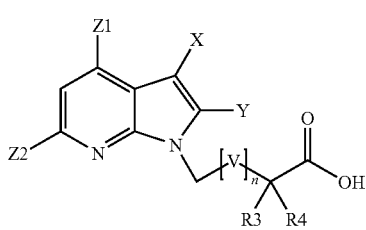
(Ia)

The present invention also relates to a process (referred to as synthetic route B) for the preparation of compounds of the formula (I), characterised in that it includes the steps consisting in:

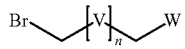

(i) performing an azaindole N-alkylation on a compound of the formula (A) described above, with a compound of the formula in which W preferably denotes a COOMe or CN radical, in the presence of a base, such as NaH (ii) performing a hydrolysis on the ester or of the nitrile of the formula VI obtained, for example with KOH in aqueous ethanol,

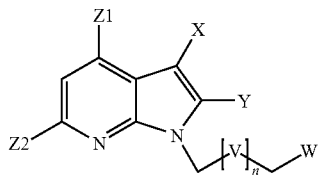
VI (iii) performing an alpha-alkylation on the acid of the formula V obtained, especially with a compound of the formula R3Br or R4Br, respectively, preferably in the presence of a base, such as LDA

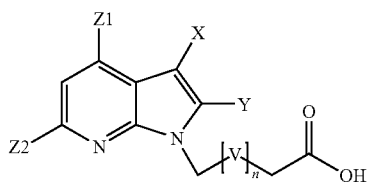
V to give the compound of the formula (Ia), which can be converted into an amide as described in synthetic route A.

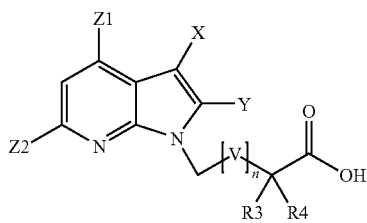
(Ia)

The present invention also relates to a process (referred to as synthetic route C) for the preparation of compounds of the formula (I), characterised in that it includes the steps consisting in:

(i) reacting a bromoalkanoyl chloride of the formula X

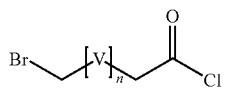
(X)

with a 2-oxazolidinone having the following formula:

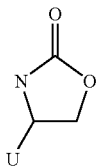

in which U is CH2Ph (R or S), or optionally i-Pr, especially in the presence of a base, such as BuLi, in a solvent, such as THF, (i) performing an azaindole alkylation on a compound of the formula (A) described above with the bromide of the formula IX obtained

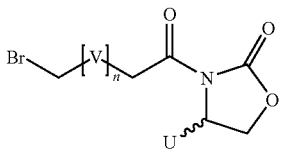

(IX)

(iii) performing a stereospecific alpha-oxazolidinone alkylation preferably of R configuration on the compound of the formula VIII obtained, especially with methyl iodide, in the presence of a base, such as LDA, in a solvent, such as THF

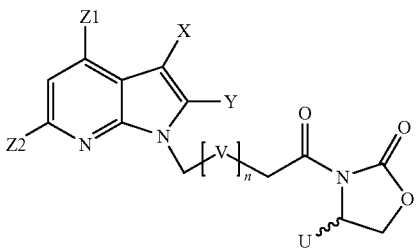

(VIII)

(iv) performing an oxazolidinone hydrolysis on the compound VII obtained, for example with 30% LiOH/H$_2$O$_2$

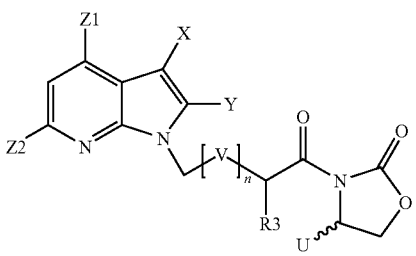

(VII)

and (v) performing an amidation on the acid of the formula Ia obtained

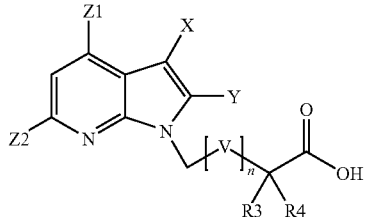

(Ia)

in which R4=H, with EDCl or acid chloride.

This process allows the stereospecific preparation of compounds of the formula (I) in very satisfactory yields.

The present invention also relates to a process for the preparation of compounds according to formula (I), comprising the steps consisting in performing a coupling between a compound of the formula (XI), which can be prepared according to one of the routes A, B or C, with a compound of the formula (XII), in the presence of a mild base and a palladium (0) derivative, such as tetrakis(triphenylphosphine)palladium (route D)

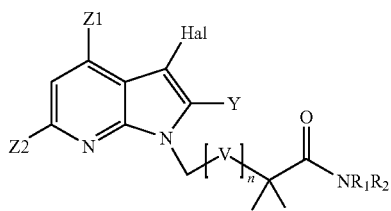

(XI)

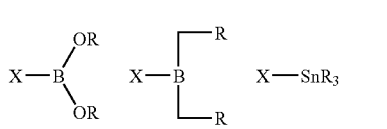

(XII)

in which, in the formula (XI), Hal represents a halogen atom, especially bromine, and in which, in the formula (XII), R can be H or alkyl in compounds of the type XB(OR)$_2$, or R can be an alkyl, such as Methyl for compounds of the type XB(CH$_2$R)$_2$, or R can be an alkyl, such as Butyl for compounds of the type XSnR$_3$.

The compounds obtained from process D can be modified in order to obtain the desired products (I), by application or adaptation of methods that are known per se or described in Example 8.

The amines that can be used for the amidation reactions described above in the various routes of the process according to the invention may be chosen from any amine corresponding to the desired final product. The suitable amines may especially be commercially available or can be synthesised by application or adaptation of a method known per se.

More specifically, amines that are suitable for the preparation of representative examples of compounds according to the invention can be prepared according to the following methods:

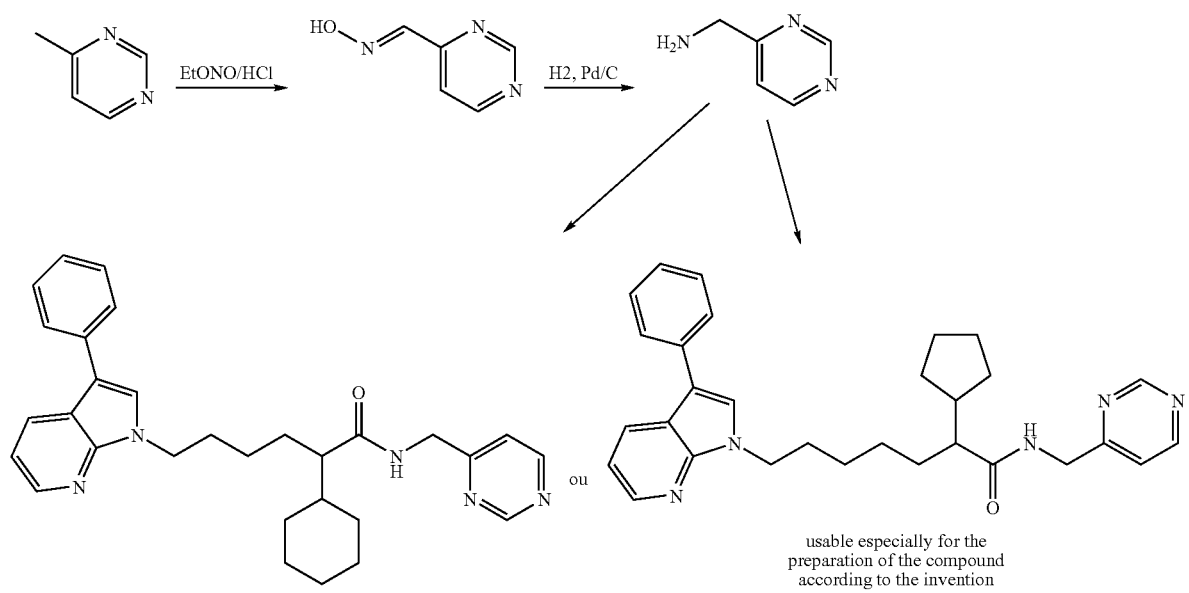

1) According the the methods described in Justus Liebig Ann. Chem. 1970, 737, 39-44 and Bull. Soc. Chim. Belg. 1982, 91 (2), 153:

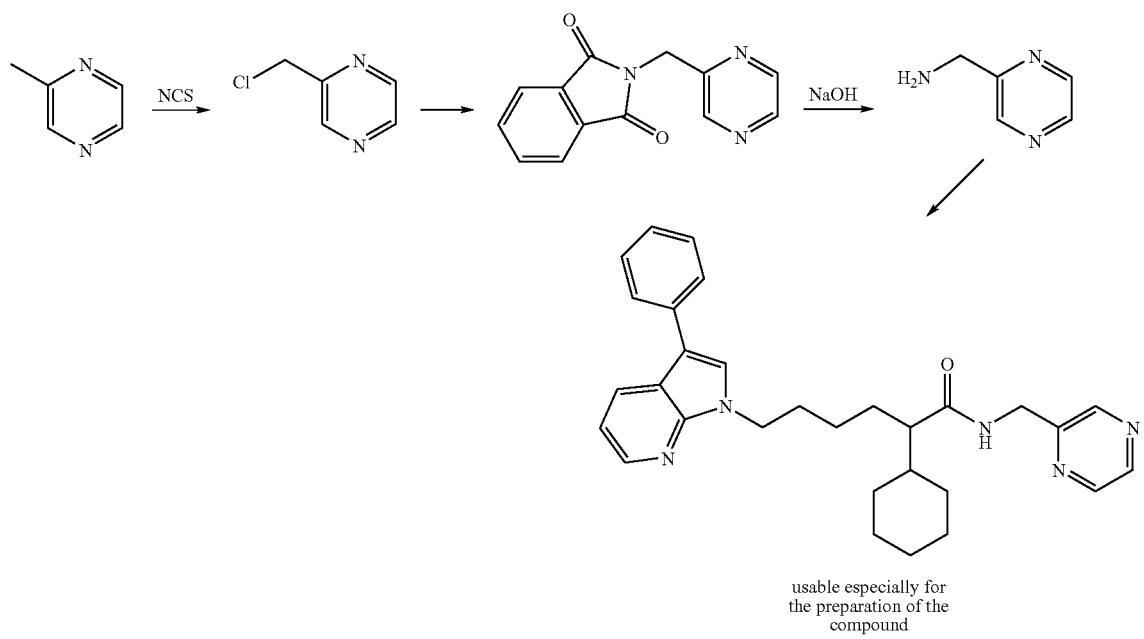

2) and according to the methods described in JOC 1973, 38, 2049 and J. Med. Chem. 1968, 11, 911

The compounds of the formula (A):

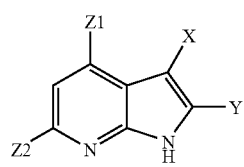

(A)

in which Z1, Z2 and X are defined as above and Y is different from H, can be prepared by application or adaptation of the method described in Tetrahedron 1992, 48(5), 939-952.

The compounds of the formula (A):

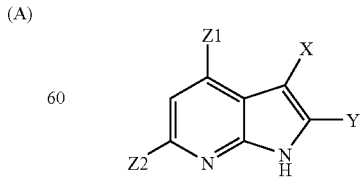

(A)

in which Z1, Z2 and X are defined as above and Y represents H can be obtained by application or adaptation of the method described in Canadian Journal of Chemistry 1966, 44, 2455-2457. They can especially be obtained from the compounds of the formula (B)

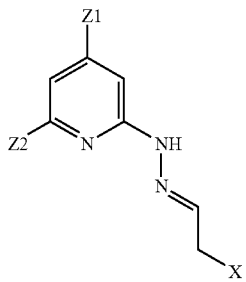

(B)

in the presence of diethylene glycol.

The compounds of the formula (B) can themselves be obtained from the compounds of the formula (C) by coupling with the compounds of the formula (D):

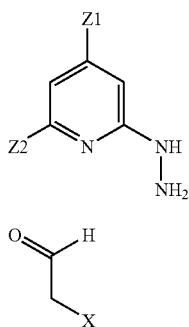

(C)

(D)

The compounds C can be obtained via the action of hydrazine on the corresponding compounds (E):

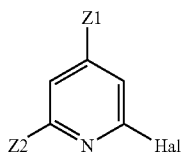

(E)

The starting products and reagents are commercially available or can be prepared by application or adaptation of means that are known per se.

The N-oxide compounds can be obtained from the compounds of the formula (I) especially by reaction with an oxidising agent, for example chloroperbenzoic acid.

The present invention also relates to pharmaceutical compositions comprising one or more compounds of the formula I according to the invention, in combination with one or more excipients.

These compositions can be administered orally in the form of tablets, gel capsules or granules with immediate release or with controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrant, a lubricant, a dye or a flavour corrector, and by forming the mixture into a tablet, a coated tablet, a granule, a powder or a capsule.

Examples of possible fillers include lactose, corn starch sucrose, glucose, sorbitol, crystalline cellulose and silicon dioxide, and examples of binders include poly(vinyl alcohol), poly(vinyl ether), ethylcellulose methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye may be any dye permitted for use in medicaments. Examples of flavour correctors include cocoa powder, mint in herb form, aromatic powder, mint in oil form, borneol and cinnamon powder. Needless to say, the tablet or granule can be suitably coated with sugar, gelatine or the like.

An injectable form comprising the compound of the present invention as active principle is prepared, where appropriate, by mixing the said compound with a pH regulator, a buffer, a suspension agent, a solubiliser, a stabiliser, a tonicity agent and/or a preserving agent, and by converting the mixture into a form for intravenous, subcutaneous or intramuscular injection, according to a standard process. Where appropriate, the injectable form obtained can be freeze-dried via a standard process.

Examples of possible suspension agents include methylcellulose, polysorbate 80, hydroxyethylcellulose, acacia, powdered gum tragacanth, sodium carboxymethylcellulose and polyethoxylated sorbitan monolaurate.

Examples of possible solubilisers include castor oil solidified with polyoxyethylene, polysorbate 80, nicotinamide, polyethoxylated sorbitan monolaurate and the ethyl ester of castor oil fatty acid.

In addition, the possible stabilisers include sodium sulfite, sodium metasulfite and ether, while the possible preserving agents include methyl p-hydroxybenzoate, ethyl p-hydroxybenzoate, sorbic acid, phenol, cresol and chlorocresol.

The dosage may vary within wide limits (0.5 mg to 1000 mg) depending on the therapeutic indication and the route of administration, and also on the age and weight of individual.

The compounds of the formula I and the pharmaceutical compositions of the invention are useful as microsomal triglyceride transfer protein (MTP) inhibitors. As such, they can be used in the treatment of hypercholesterolaemia, hypertriglyceridaemia, hyperlipidaemia, pancreatitis, hyperglycaemia, obesity, atherosclerosis and diabetes-related dyslipidaemia.

Thus, according to another of its aspects, the invention relates to the use of a compound or of a pharmaceutical composition according to the invention for the preparation of a medicament that inhibits microsomal triglyceride transfer protein.

The compounds of the invention also allow inhibition of apoprotein B (ApoB) secretion.

The compounds of the invention also show their activity by inhibition of the secretion of very low density lipoproteins (VLDL). The demonstration of an inhibition of VLDL secretion makes it possible to demonstrate the in vivo activity of the compounds of the invention.

The in vivo activity can be simply demonstrated in Wistar rats by performing the following operating protocol. Measurement of the hepatic VLDL secretion was performed by blocking the degradation of the VLDLs via i.v. injection of Triton (Tyloxapol) at 400 mg/kg after fasting for 2 hours. The evaluation of the VLDL secretion is performed by determining the accumulation of triglycerides and cholesterol in the bloodstream over a period of 5 hours. The compounds of the invention reduce this hepatic secretion of VLDLs.

The examples moreover propose two operating protocols for demonstrating MTP inhibition and inhibition of ApoB secretion.

The examples that follow illustrate the present invention in greater detail.

The nuclear magnetic resonance spectra are the proton spectra, acquired at 300 MHz and at room temperature. The chemical shifts are expressed in ppm and their reference is taken in each case on the signal of the deuterated solvent (chloroform at 7.25 ppm or dimethyl sulfoxide at 2.5 ppm).

The signals are described with the following abbreviations: s=singlet, d=doublet, t=triplet, dd=doublet of doublets, dt=doublet of triplets, td=triplet of doublets, m=multiplet.

The mass spectra are acquired on a Waters/Micromass Platform-LC LC/MS machine in positive electrospray mode with a cone voltage of 20 volts.

Mp denotes the melting point.
MS denotes the mass spectrometry data.
NMR denotes the nuclear magnetic resonance data.

EXAMPLES

Representative Examples of Methods for the Preparation of the Compounds of the Invention Some of the compounds exemplified below as illustrations present Z1=Z2H. Needless to say, the procedures described below can be performed in the same manner with compounds for which Z1 and Z2 are defined as above.

Example 1

Preparation according to route a of compounds of the invention "containing a C8 chain, cyclopentyl" of the formula (I) in which Z1=Z2=H, n=5, i.e. V=—(CH2)5-, X=Ph, Y=H, R1=H, R2=—CH2—Ar, with Ar=(2')pyr, or (4')pyr; R3=R=cyclopentyl and R4=H The compounds of the invention having the following formula:

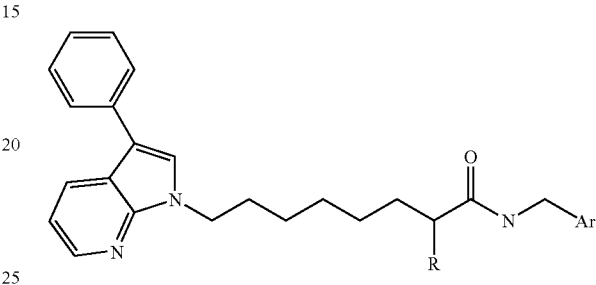

can be obtained according to the following reaction scheme detailed below:

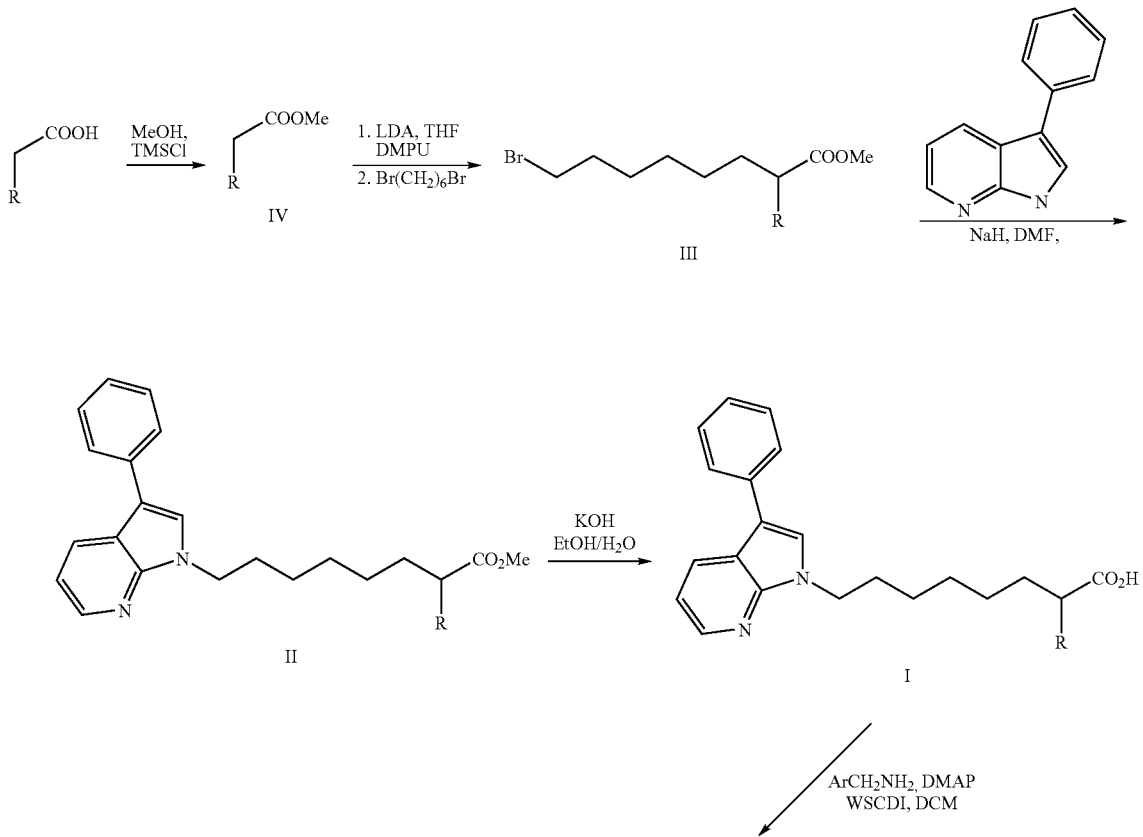

-continued

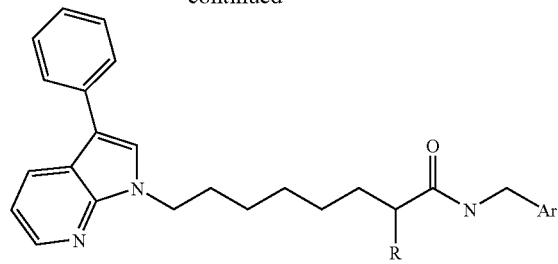

1.1 Synthesis of the ester IV: 5.15 g (39 mmol) of cyclopentylacetic acid, 2.45 ml (59 mmol) of methanol and 2.52 ml (20 mmol) of trimethylsilyl chloride are introduced into a 50 ml pear-shaped flask. The reaction mixture is stirred at room temperature overnight. Two phases are formed. $NaHCO_3$ is added to alkaline pH, the mixture is extracted with $CH_2Cl_2$, washed with $H_2O$, dried and evaporated (50° C./80 mm Hg): 5.5 g (99%) of ester 300DN41 IV are obtained in the form of an oil.

$^1H$ NMR: ($CDCl_3$): 1.02-1.29 (2H, m); 1.43-1.99 (6H, m); 2.09-2.46 (3H, m); 3.64 (3H, s).

As other starting acids, mention may be made of cyclohexylacetic acid, 3-methylvaleric acid, 2-cyclopentene-1-acetic acid, phenylacetic acid, isovaleric acid, 3,3-dimethylbutyric acid, cyclopentylacetic acid and cycloheptylacetic acid.

1.2 Synthesis of the bromo ester III: 19.3 ml (39 mmol) of LDA are dissolved in 45 ml of anhydrous THF in a 250 ml reactor, under N2, and cooled to −70° C. 5.48 g (39 mmol) of ester IV are added and stirring is continued at −70° C. for 1 hour. 12 ml (77 mmol) of dibromohexane are then added dropwise and the reaction mixture is stirred for 3 hours at −70° C. 20 ml of water are added slowly and the temperature is raised to room temperature. 195 ml of saturated $NH_4Cl$ solution are added, the mixture is extracted with EtOAc and the extracts are dried over $Na_2SO_4$, filtered and evaporated. The product is distilled at 0.1 mmHg, and 2.8 g of bromo ester III 300DN47 are obtained at 115-118° C.

1H NMR: ($CDCl_3$): 0.85-2.34 (2H, m); 2.34-2.64 (1H, m); 3.22-3.46 (1H, m); 3.65 (3H, s).

Other alkylating agents that may be mentioned include: 1,4-dibromobutane; 1,5-dibromopentane; 1,6-dibromohexane; 2-bromoethyl ether.

Another starting ester (R4 other than H) that may be mentioned is methyl cyclopentanecarboxylate.

1.3 Synthesis of the ester II: 0.36 g (9 mmol) of 60% NaH is dissolved in 20 ml of DMF in a 100 ml three-necked flask under N2. 1.57 g (8 mmol) of 3-phenylpyrrolo[2,3-b]pyridine dissolved in 20 ml of DMF are added dropwise. The mixture is heated at 50° C. for 1 hour. The bromo ester III is then added as a solution in 5 ml of DMF at room temperature, and stirring is continued overnight.

Water is added dropwise and the mixture is then poured onto an excess of water, extracted with EtOAc, washed with $H_2O$, dried over $Na_2SO_4$, filtered and evaporated. After flash chromatography on silica gel with 1/3 EtOAc/heptane, 1.64 g of the product II 300DN48 are obtained.

1H NMR: (DMSO-d6): 0.88-2.20 (2H, m); 3.54 (3H, s); 4.17-4.41 (2H, m); 7.09-7.32 (2H, m); 7.35-7.51 (1H, m); 7.63-7.78 (2H, m); 7.96 (1H, s); 8.21-8.37 (2H, m).

Other starting azaindoles that may be mentioned include: 2-phenylpyrrolo[2,3-b]pyridine and pyrrolo[2,3-b]pyridine.

1.4. Synthesis of the acid I: 1.2 g (20.5 mmol) of KOH dissolved in 40 ml of EtOH and 13 ml of water are added to 1.56 g (3.73 mmol) of ester II. The reaction mixture is refluxed overnight. It is cooled to room temperature and acidified with 16% HCl and then with N HCl: pH=about 4.5 (pH-meter). The resulting mixture is extracted with $CH_2Cl_2$, dried over $Na_2SO_4$ and evaporated. 1.29 g of acid I are obtained.

300DN050: 1H NMR: (DMSO-d6): 0.90-2.08 (2H, m); 4.15-4.41 (2H, m); 7.06-7.33 (2H, m); 7.61-7.80 (2H, m); 7.97 (1H, s); 8.16-8.40 (2H, m); 11.97 (1H, broad s).

This example illustrates the steps in the preparation of a compound containing a C8 chain.

The last step is an amidation of the acid precursor I to obtain a compound of the invention.

As other examples of compounds that can be obtained according to route A, mention may be made of compounds containing a C6 chain with R3 possibly being cyclohexyl, 2-butyl, (2',3')-cyclopentenyl, phenyl, isopropyl, cycloheptyl, tert-butyl; compounds containing a C7 chain, R3=cyclopentyl cyclohexyl and cycloheptyl; compounds containing an ether chain, R3 cyclopentyl; refer to the corresponding figures attached to the present description illustrating their synthetic schemes.

Example 2

Preparation according to route B of the acid precursor of the compound of the invention of the formula (I) containing a C6 chain, cyclopentyl (i.e. in which Z1=Z2=H, n=3 i.e. V=—(CH2)3-, and R3=cyclopentyl) with X=Phe, Y=H, R1=H, R4=H, and W=CO2Et The reaction scheme corresponding to the synthesis via route B of this compound containing a C6 chain, cyclopentyl is illustrated below, the numbers given to the following compounds referring thereto and the yields being indicated for the case where z1=Z2=H:

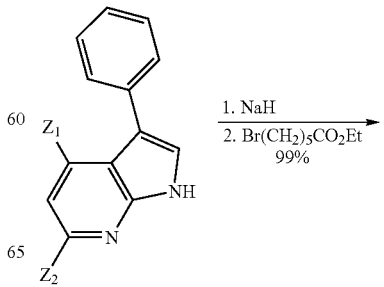

-continued

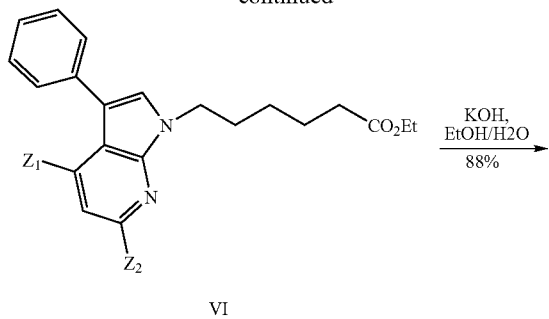

VI

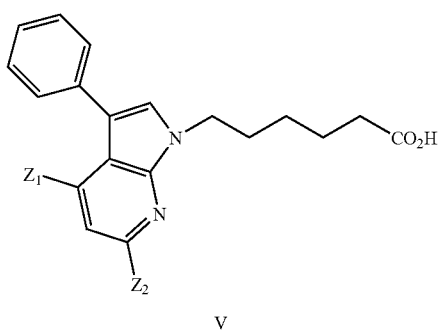

V

1. LDA, THF
21% | 2. cyclopentyl-Br

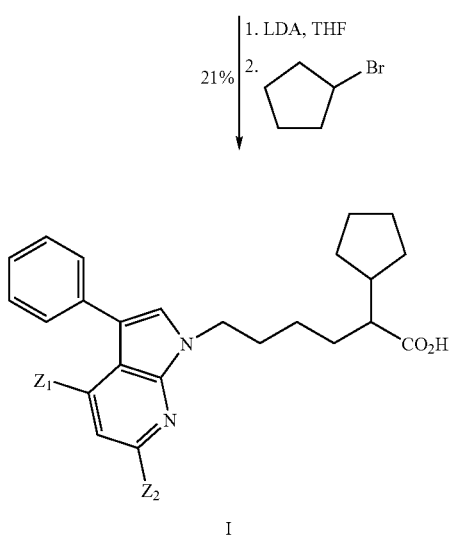

I 2.1 Synthesis of the ester VI: 50.5 g (0.26 mol) of 3-phenylpyrrolo[2,3-b]pyridine in 350 ml of DMF are added dropwise to a suspension of 11.4 g (0.28 mol) of sodium hydride (60% suspension in oil) in 130 ml of DMF. The mixture is heated at 40° C. for 1 hour, and a solution of 60.7 g (0.27 mol) of ethyl 6-bromohexanoate is then added at 10° C. The resulting mixture is stirred at room temperature for 5 days and then treated by dropwise addition of water (500 ml) with cooling. After extraction with dichloromethane, washing with saturated NaCl solution, drying over sulfate and evaporation, 87.2 g (99%) of an oil VI are obtained;

NMR (DMSO-d6): 1.03-1.17 (3H, t, J=7.16 Hz); 1.19-1.40 (2H, m); 1.44-1.63 (2H, m); 1.75-1.94 (2H, m); 2.18-2.33 (2H, m); 3.90-4.11 (2H, q, J=7.16 Hz); 4.18-4.38 (2H, m); 7.10-7.34 (2H, m); 7.35-7.50 (2H, m); 7.63-7.77 (2H, m); 7.97 (1H, s); 8.23-8.37 (2H, m).

Other starting azaindoles that may be mentioned include 2 phenylpyrrolo[2,3-b]pyridine and pyrrolo[2,3-b]pyridine.

2.2 Synthesis of the acid V: A mixture of 42.0 g (185 mmol) of methyl 6-(3-phenylpyrrolo[2,3-b]pyrid-1-yl)hexanoate VI, 1.4 L of 0.5N KOH in ethanol and 700 ml water is refluxed for 3.5 hours. The mixture is treated by acidifying with 16% HCl and then with 1N HCl to pH 4-5 (pH-meter). After stirring and filtering off the precipitate by suction, washing with water and drying, 34 g (88%) of a white solid V 203GR64 are obtained: m.p.=118° C.; NMR (DMSO-d6): 1.12-1.40 (2H, m); 1.43-1.64 (2H, m); 1.72-1.96 (2H, m); 2.08-2.28 (2H, m); 4.14-4.44 (2H, m); 7.06-7.34 (2H, m); 7.34-7.52 (2H, m); 7.59-7.77 (2H, m); 7.98 (1H, s); 8.16-8.37 (2H, m); 11.98 (1H, broad s).

2.3 Synthesis of the acid I (R3=cyclopentyl, R4=H, W=CO2Et): A solution of 7.7 g (0.025 mol) of 6-(3-phenylpyrrolo[2,3-b]pyrid-1-yl)hexanoic acid V in 80 ml of THF is added to a solution of 31.2 ml (0.05 mol) of LDA in 60 ml of THF, under nitrogen and between −15° C. and −20° C. The mixture is stirred at 0° C. for 1 hour and then cooled to −30° C. 11 ml (0.1 mol) of cyclopentyl bromide are then added. The mixture is allowed to warm to room temperature and stirring is continued overnight. The resulting mixture is treated with water and is then acidified with 0.5N HCl and then, with 1N HCl to pH 4-5 (pH-meter). After extraction ($CH_2Cl_2$), drying over sulfate and evaporation, 8 g of a solid are obtained, which are purified by chromatography (400 g of $SiO_2$, 1/1 ethyl acetate/heptane) to give 2 g of an oil/203GR74; 21% yield; 1H NMR (DMSO-d6): 0.93-2.09 (15H, m); 3.92-4.11 (2H, m); 7.61-7.82 (2H, m); 7.96 (1H, s); 8.20-8.37 (2H, m); 11.99 (1H, broad s).

Other alkylating agents that may be mentioned include 6-bromohexanenitrile, allyl bromide and iodocyclopentyl bromide.

The corresponding compound of the invention of the formula (I) is obtained by amidation of the acid precursor thus obtained.

As examples of other compounds of the invention obtained via the same route B, mention may be made of compounds containing a C5 chain with R3=cyclopentyl, and compounds containing a C6 chain, with R3=rac-allyl: refer to the corresponding figures attached to the present description.

Example 3

Preparation according to route C of the compounds of the invention of the formula (I) containing a C6 chain, R=methyl (i.e. in which Z1=Z2=H, n=3, i.e. V=—(CH2)3— and R3=R-Me) with X=Phe, Y=H, R4=H; and U=CH2-Ph The reaction scheme corresponding to route C is illustrated especially in the following scheme, the numbers given to the following compounds referring to this scheme, and the yields indicated corresponding to the case where Z1=Z2=H:

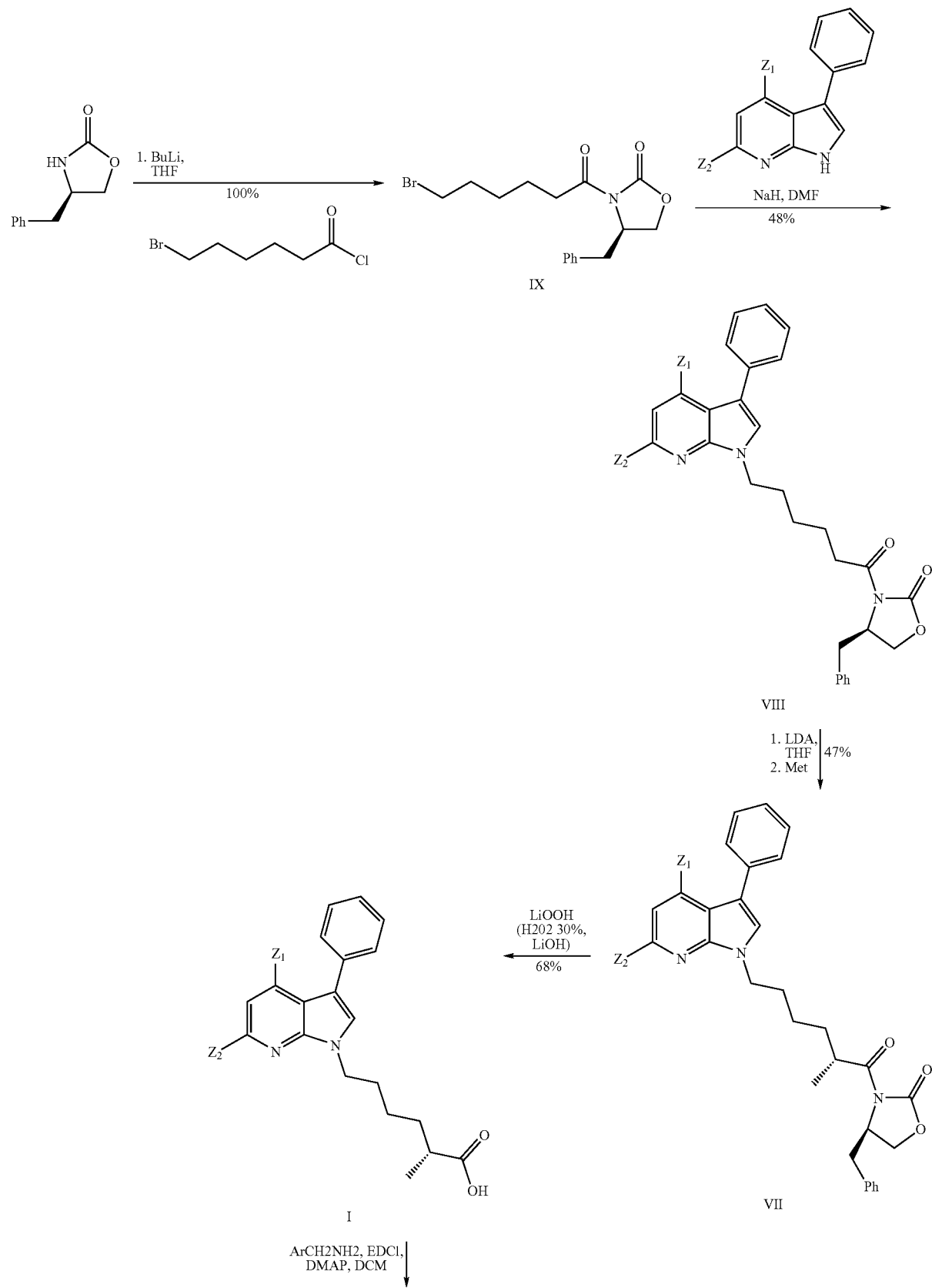

-continued

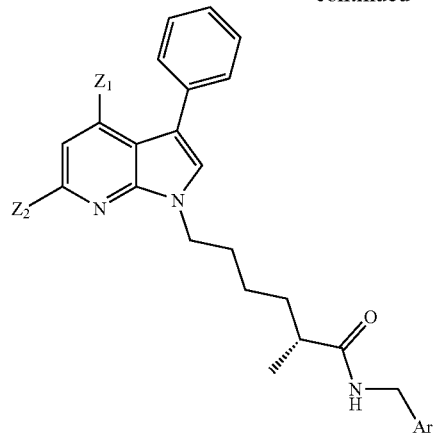

3.1 Synthesis of the bromide IX (U=CH2Ph): 34.6 ml (55 mmol) of a 1.6N solution of butyllithium are added at −70° C. to 10 g (550 mmol) of (R)-4-benzyl-2-oxazolidinone in 400 ml of THF. The reaction, mixture is stirred for 15 minutes at −70° C. and 10.48 ml (66 mmol) of 6-bromo-hexanoyl chloride are then added dropwise. The reaction mixture is stirred for 15 minutes at −70° C. and then for 30 minutes at 0° C. The mixture is hydrolysed by addition of 300 ml water, extracted, with Et$_2$O, dried over Na$_2$SO$_4$, filtered and evaporated to dryness.

The product is chromatographed on silica gel with 1/2 EtOAc/heptane. 20.9 g of product IX are obtained in the form of an oil.

300DN005 1H NMR: (DMSO-d6): 1.23-1.97 (6H, m); 2.65-3.13 (4H, m); 3.44-3.70 (2H, m); 4.06-4.47 (2H, m); 4.52-4.79 (1H, m); 7.02-7.51 (5H, m).

Another oxazolidinone that can be used is (S)-4-benzyl-2-oxazolidinone.

Another alkylating agent that can be used is allyl bromide.

3.2 Synthesis of the oxazolidinone VIII: 2.2 g (57 mmol) of 60% NaH are dissolved in 100 ml of DMF in a 100 ml three-necked flask, under N2. 9.6 g (49 mmol) of 3-phenylpyrrolo[2,3-b]pyridine dissolved in 100 ml of DMF are added dropwise. The mixture is heated at 50° C. for 1 hour. 20.9 g (59 mmol) of bromide IX are then added as a solution in 10 ml of DMF at room temperature, and stirring is continued overnight.

Water is added dropwise and the mixture is then poured onto an excess of water, extracted with EtOAc, washed with H$_2$O, dried over Na$_2$SO$_4$, filtered and evaporated. After flash chromatography on silica gel with 1/1 EtOAc/heptane, 13.3 g of product VIII are obtained in the form of an oil.

300DN014, 1H NMR: (DMSO-d6): 1.21-2.05 (6H, m); 2.65-3.17 (4H, m); 4.06-4.50 (4H, m); 4.50-4.74 (1H, m); 7.06-7.60 (9H, m); 7.62-7.87 (2H, m); 7.98 (1H, s); 8.20-8.47 (2H, m).

3.3 Synthesis of the oxazolidinone VII: 5.5 ml of a 1M solution of NaHMDS in THF are added under N2, at −70° C., to 2.5 g (5.35 mmol) of oxazolidinone VIII, dissolved in 120 ml of THF. The reaction mixture is stirred for 1 hour at −70° C., 1.66 ml (26.74 mmol) of methyl iodide are then added and stirring is continued overnight at between −20° C. and −30° C.

The mixture is hydrolysed by addition of saturated NH$_4$Cl solution. The temperature is returned to room temperature and the THF is evaporated off. The residue is washed with 100 ml of 1M NaHCO$_3$ solution and then with H$_2$O, extracted with Et$_2$O, dried over Na$_2$SO$_4$, filtered and evaporated. After flash chromatography on silica gel, eluting with 2/1 heptane/ethyl acetate, 1.2 g of product VII are obtained in the form of an oil.

300DN014, 1H NMR: (DMSO-d6): 1.21-2.05 (6H, m); 2.65-3.17 (4H, m); 4.06-4.50 (4H, m); 4.50-4.74 (1H, m); 7.06-7.60 (9H, m); 7.62-7.87 (2H, m); 7.98 (1H, s); 8.20-8.47 (2H, m).

Another alkylating agent that can be used is allyl bromide.

3.3 Synthesis of the acid I: 0.872 ml (9.967 mmol) of 35% H$_2$O$_2$ and then 97.43 mg of LiOH dissolved in 5.4 ml of water are added, between 0 and +5° C., to 1.2 g (2.49 mmol) of VII in a mixture of 13 ml of THF and 3.5 ml of water. The reaction mixture is stirred for 1 hour 30 minutes at this temperature, and 1.26 g (9.967 mmol) of Na$_2$SO$_3$ dissolved in 8 ml of water are then added. After checking to confirm the absence of peroxides, the THF is evaporated off. The aqueous phase is extracted with EtOAc and acidified with 16% HCl and then with 1N HCl to pH 4.5. After extraction with CH$_2$Cl$_2$ and drying over Na$_2$SO$_4$, 550 mg of acid I are obtained in the form of white crystals.

300DN028, 1H NMR: (DMSO-d6): 0.92-1.09 (3H, d, J=6.87 Hz); 1.15-1.70 (4H, m); 1.73-1.95 (2H, m); 2.18-2.40 (1H, m); 4.16-4.45 (2H, m); 7.07-7.81 (6H, m); 7.97 (1HY, s); 7.89-8.07 (2H, m); 11.03 (1H, broad s).

The compounds of the invention are obtained by amidation of the acid precursor.

As other compounds of the invention that can also be obtained via the said route C, mention may be made of compounds containing a C6 chain, R3=S-methyl, and R-allyl and reference may be made to the corresponding figures attached to the present description.

Example 4

Preparation of a compound of the invention of the formula (I) containing a C8 chain, cyclopentyl (i.e. with n=5, and R3=cyclopentyl) with Z1=Z2=H, X=Phe, Y=H, R1=H, R2=—CH2-(2)pyr, and R4=H by amidation of the corresponding acid precursor via EDCl.

The following compound was thus prepared as outlined below:

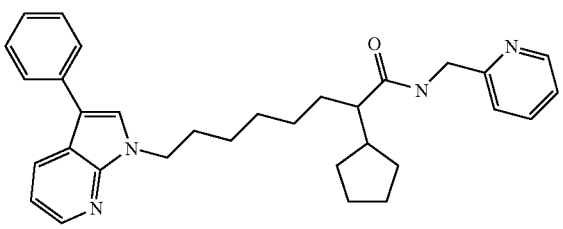

100 mg (0.25 mmol) of the corresponding acid precursor in 12 ml of $CH_2Cl_2$ are added to a solution of 27 mg (0.25 mmol) of 2-(aminomethyl)pyridine, 30.5 mg (0.25 mmol) of DMAP and 48.36 mg (0.25 mmol) of (3-dimethylaminopropyl)-2-ethylcarbodiimide hydrochloride in 9 ml of $CH_2Cl_2$. The mixture is stirred at room temperature overnight.

The solvent is evaporated off and the product is purified by flash chromatography on silica gel. Eluent: 1/1 $CH_2Cl_2$/ethyl acetate and then 90/10 EtOAc/MeOH. 104 mg (85%) of amide according to the invention are obtained in the form of crystals.

1H NMR: (DMSO-d6): 0.78-2.14 (20H, m); 4.10-4.62 (4H, m); 7.03-7.84 (9H, m); 7.97 (1H, s); 8.21-8.58 (4H, m).

Another amine that can be used is one of the following:

Benzylamine, 4-methylsulfonylbenzylamine hydrochloride, 4-(aminomethyl)pyridine, (6-methylpyrid-2-yl)methylamine, 4-carbomethoxybenzylamine, 4-methoxybenzylamine, 4-(aminomethyl)benzenesulfonamide or C-benzo[1,3]dioxol-5-ylmethylamine.

Example 5

Amidation of the acid precursor of the compounds of the invention via the acid chloride.

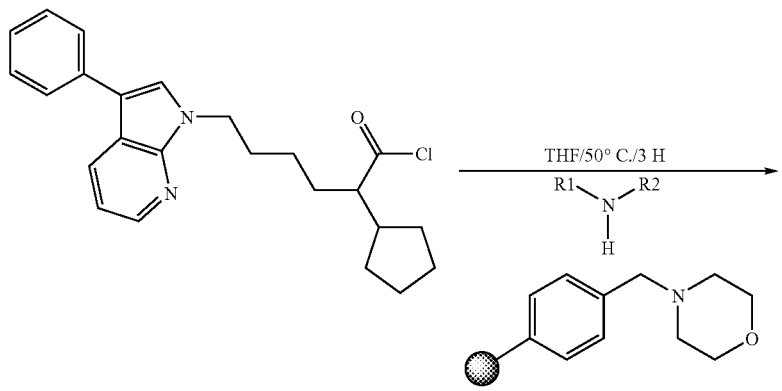

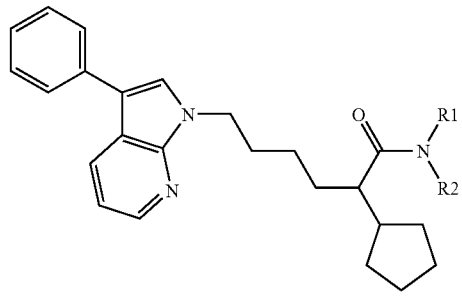

The synthesis preferably involves the following two steps:
Step 1:
The details of the reaction protocol used will now be given: (order of addition of the reagents, stirring, heating, temperature, duration, etc):

Evaporate off the THF (Genevac);
Filter automatically into a labelled, unstoppered Wheaton tube according to the protocol below;
Accurately weigh out about 210 µmol of amine according to the weighing table, into a 16 ml reactor+magnetic stirrer;
Add 3 equivalents (118 mg±10%) of supported NMM, using an Argonaut measuring spoon;
Dilute with 2.5 ml of THF (dispenser);
Stir for 30 minutes at 50° C. (swelling of the resin);
Add 1.5 ml of a 0.1 M solution of freshly prepared acid chloride (CVI) in THF; and Stir for 3 hours at 50° C.

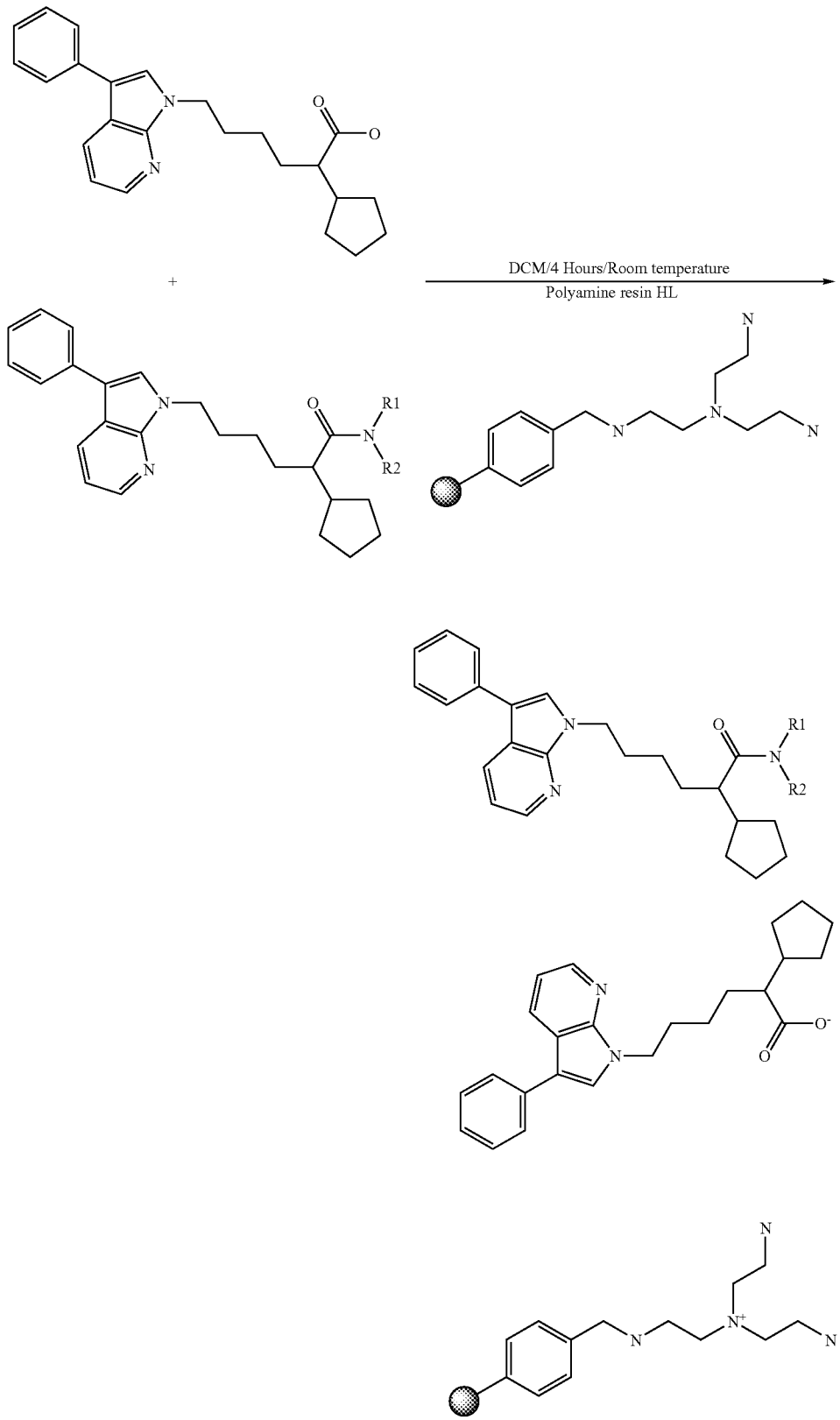

Step 2:

Into a reactor from the concentration step,

Add 6 equivalents (265 mg±10%) of polyamine resin, using an Argonaut measuring spoon.

Dilute with 5 ml of DCM (dispenser).

Stir for 4 hours at room temperature.

Filter automatically into a tared Corning tube according to the protocol below.

Take a sample for LC/MS.

Evaporate (Genevac).

Example 6

Synthesis of the Corresponding Acid Chloride 0.14 ml (1.8 mmol) of DMF are added to a solution of 6.8 g (18 mmol) of acid I in 200 ml of $CH_2Cl_2$, followed by addition of 3.2 ml (36 mmol) of oxalyl chloride. The resulting mixture stirred for 2 hours at room temperature, and then evaporated to dryness and dissolved in 180.6 ml of THF for automated production.

To make the acid chloride, it is also possible to use: bis(2-oxo-3-oxazolidinyl)phosphinic chloride, $Et_3N$; addition at 0° C., stirring overnight at room temperature.

Example 7

Palladium-Mediated Coupling (Route D)

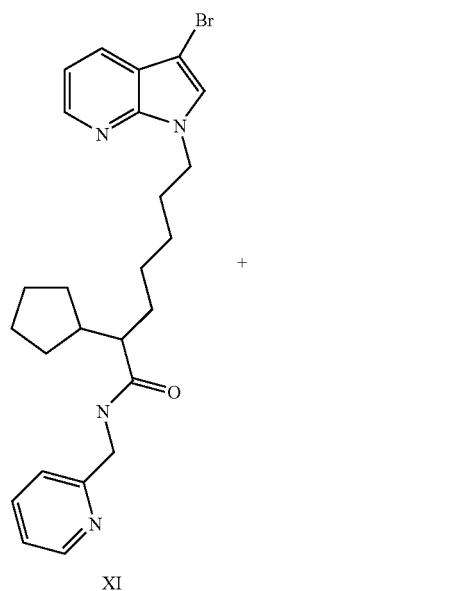

+

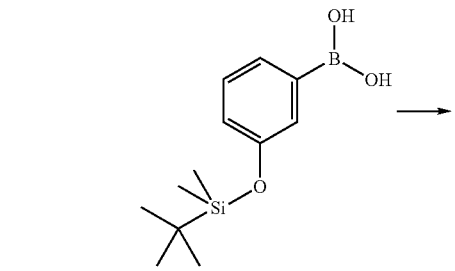

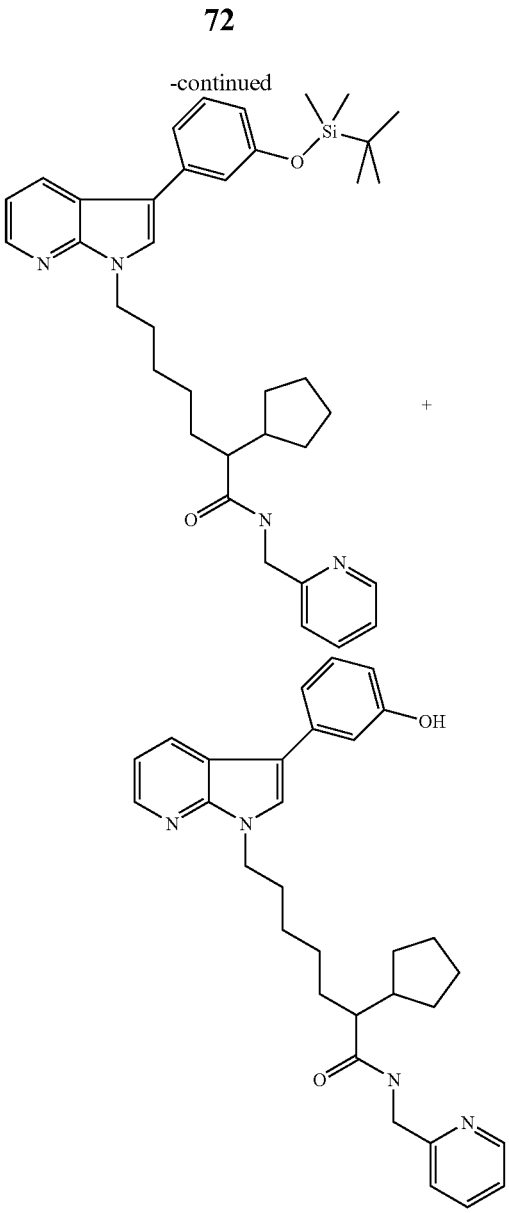

2.7 g (5.71 mmol) of XI, 1.73 g (6.85 mmol) of 3-(tert-butyldimethyl-silyloxy)phenylboronic acid, 3.63 g (34.25 mmol) of $Na_2CO_3$ and 0.198 g of tetrakis(diphenylphosphine)palladium are dissolved in a mixture of 85 ml of 1,2-dimethoxyethane and 13 ml of water.

The reaction mixture is refluxed for 8 hours. It is then diluted in ethyl acetate and water is added. The organic phase is washed with water and then dried over $Na_2SO_4$, and the product is evaporated to dryness.

After flash chromatography on silica gel, eluting with 1/1 EtOAc/$CH_2Cl_2$ and then 80/20 $CH_2Cl_2$/MeOH, 1.08 g of silyl product are obtained in the form of an oil, and 375 mg of desilylated product are also obtained.

1H NMR silyl product:

(DMSO-d6): 0.00 (6H, s); 0.74 (9H, s); 0.87-1.80 (18H, m); 4.00-4.20 (4H, m); 6.48-6.58 (1H, m); 6.86-7.20 (6H, m); 7.45-7.52 (1H, m); 7.74 (1H, s); 7.97-8.29 (4H, m).

$^1$H NMR deprotected product:

(DMSO-d6); 0.80-1.85 (18H, m); 4.00-4.20 (4H, m); 6.40-6.47 (1H, m); 6.85-7.10 (6H, m); 7.45-7.52 (1H, m); 7.66 (1H, s); 7.97-8.29 (4H, m); 9.17 (1H, s).

By application of this method, the following compounds were also prepared:

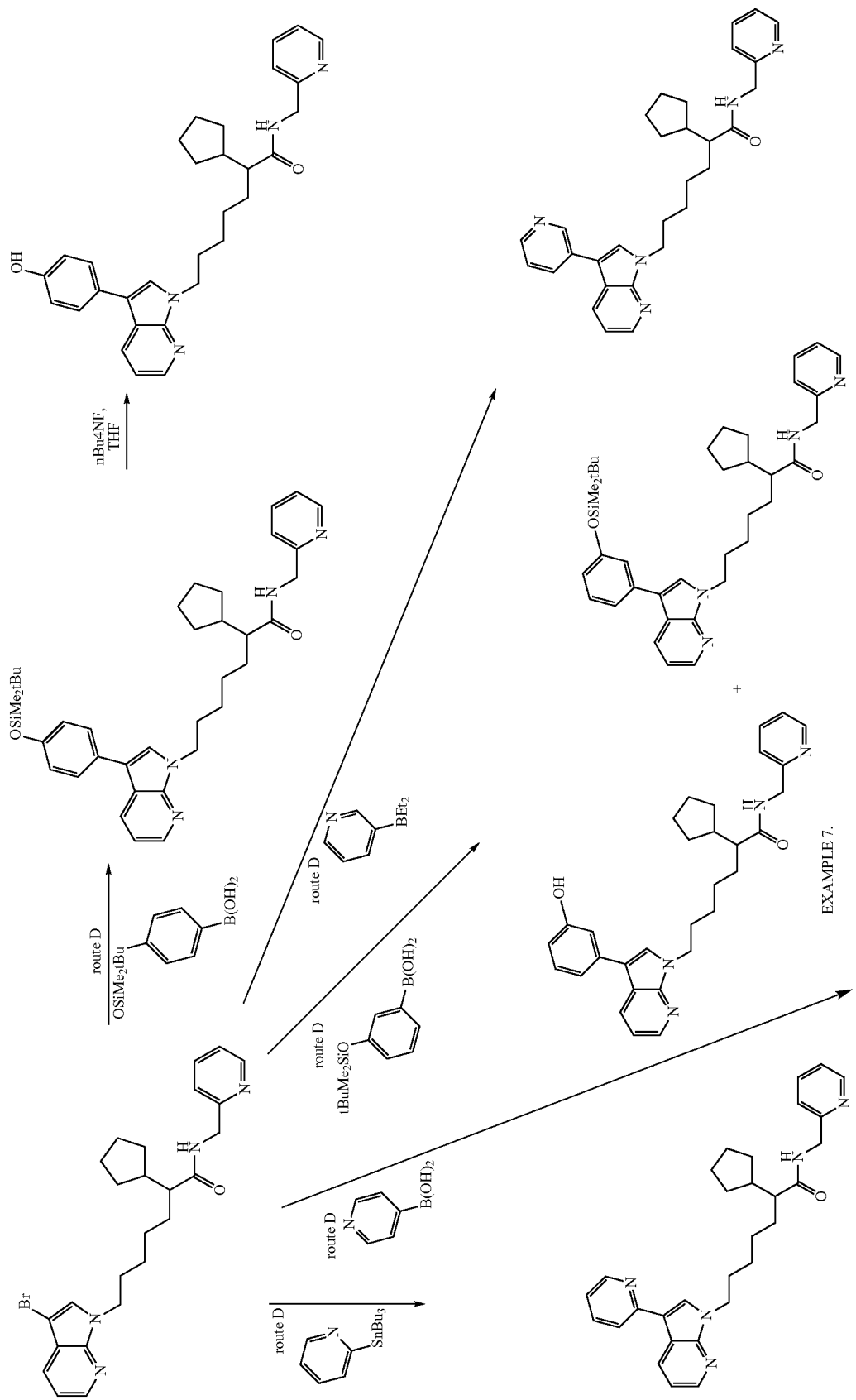

-continued
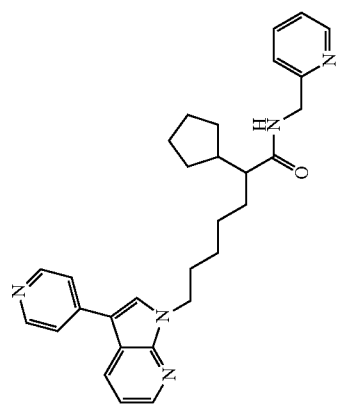

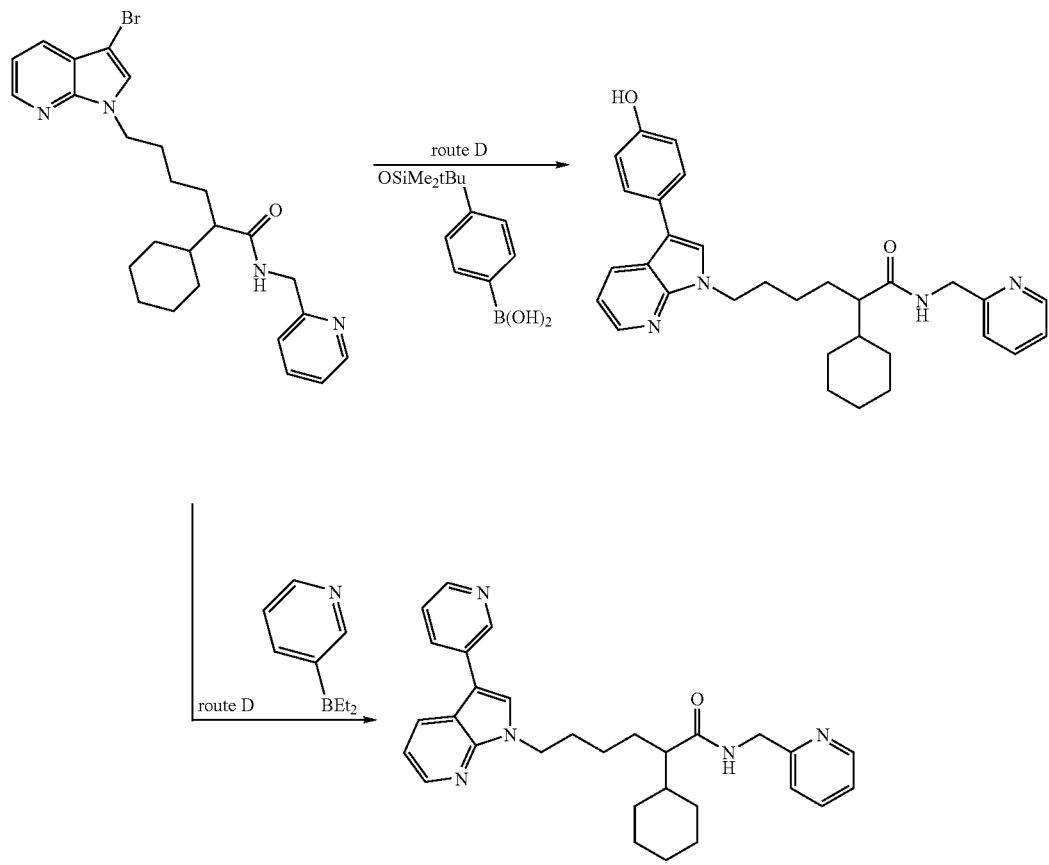
The data for compound XI are given in the description.
Compound XI can be obtained by application of methods that are known per se, starting from the following compounds:
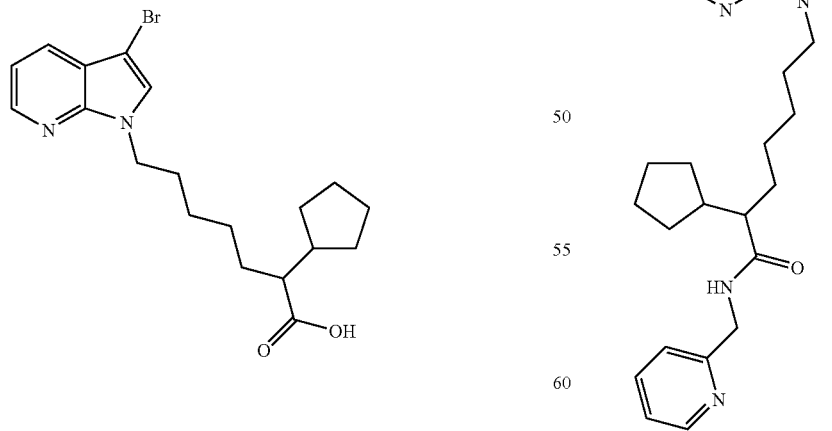
1H NMR (300 MHz, DMSO-D6) δ ppm 1.1 (m, 6H) 1.5 (m, 7H) 1.8 (m 4H) 2.0 (m, 1H) 3.6 (s, 3H) 4.2 (t, J=Hz, 2H) 7.2 (dd, J=7.9, 4.7 Hz, 1H) 7.8 (s, 1H) 7.8 (dd, J=7.9, 1.5 Hz, 1H) 8.3 (dd, J=4.7, 1.5 Hz, 1H)
and
1H NMR (300 MHz, DMSO-D6) 1.3 (m, 13H) 1.8 (m, 4H) 2.0 (m, 1H) 4.2 (t, J=7.1 Hz, 2H) 4.3 (d, J=5.9 Hz, 2H) 7.2 (m, 3H) 7.7 (m, 1H) 7.8 (s, 1H) 7.9 (dd, J=8.0, 1.5 Hz, 1H) 8.3 (dd, J=4.7, 1.4 Hz, 1H) 8.4 (m, 1H) 8.5 (d, J=4.6 Hz, 1H)

Example 8

Preparation of Derivatives of the Products Obtained from Route D

1)

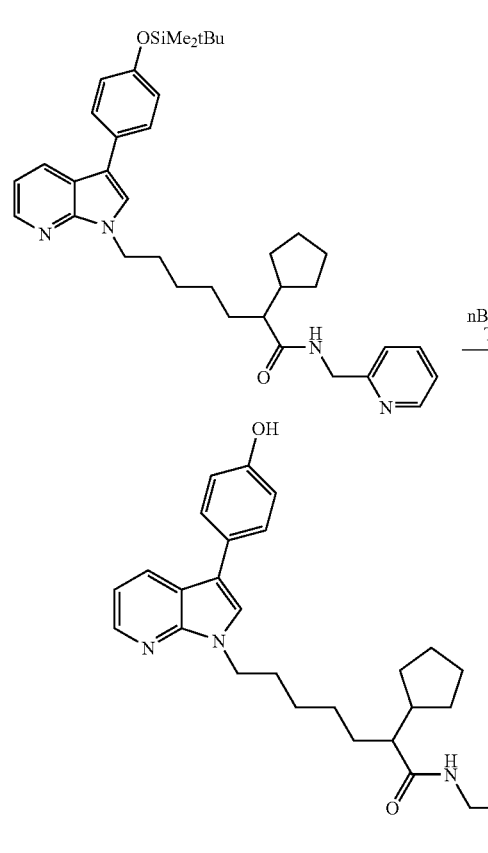

6.78 ml (6.78 mmol) of a 1M solution of TBAF in THF are added to a solution of 2.15 g (3.39 mmol) of silyl derivative obtained by application of Example 7 in 21 ml of THF, cooled to 0° C. The mixture is allowed to warm to room temperature and is then stirred for 60 hours. After aqueous treatment, extraction with EtOAc and washing with water, the organic solution is dried ($Na_2SO_4$). After filtration and evaporation, 2.02 g of an oil are obtained, and are purified by chromatography ($SiO_2$, 98/2 DCM/MeOH and then 95/5 DCM/MeOH) to give 977 mg (58%) of white crystals.

2)

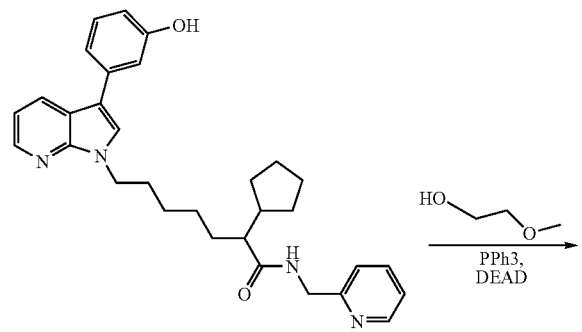

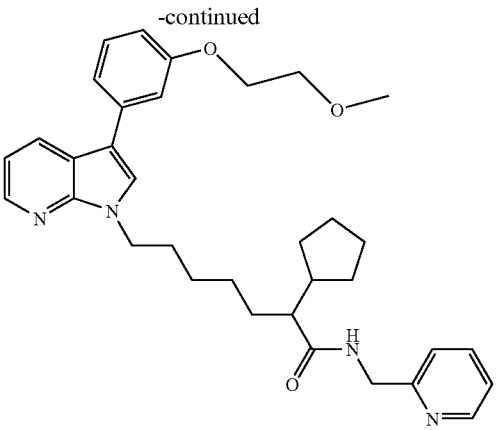

a)

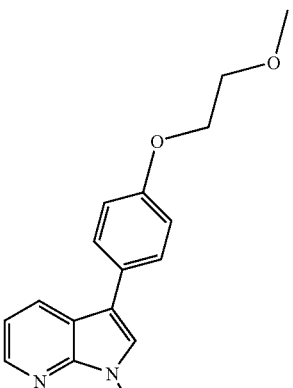

b)

a: A solution of 202 μl (1.25 mmol) of diethyl azodicarboxylate in 1 ml of THF is added to a mixture of 310 mg (0.624 mmol) of phenol, 94.9 mg (1.25 mmol) of methoxyethanol and 327 mg (1.25 mmol) of triphenylphosphine in 5 ml of THF, cooled in an ice bath. The mixture is allowed to warm to room temperature and is then stirred overnight, then heated at 50° C. for 6 hours, and then left to stand at room temperature for 60 hours. After evaporation to dryness, 1.02 g of an oil are obtained, which are purified by chromatography ($SiO_2$, 97/3 DCM/MeOH) to give 149 mg (43%) of an oil.

b: same procedure as a.

Example 9

Preparation of the N-Oxide Compounds

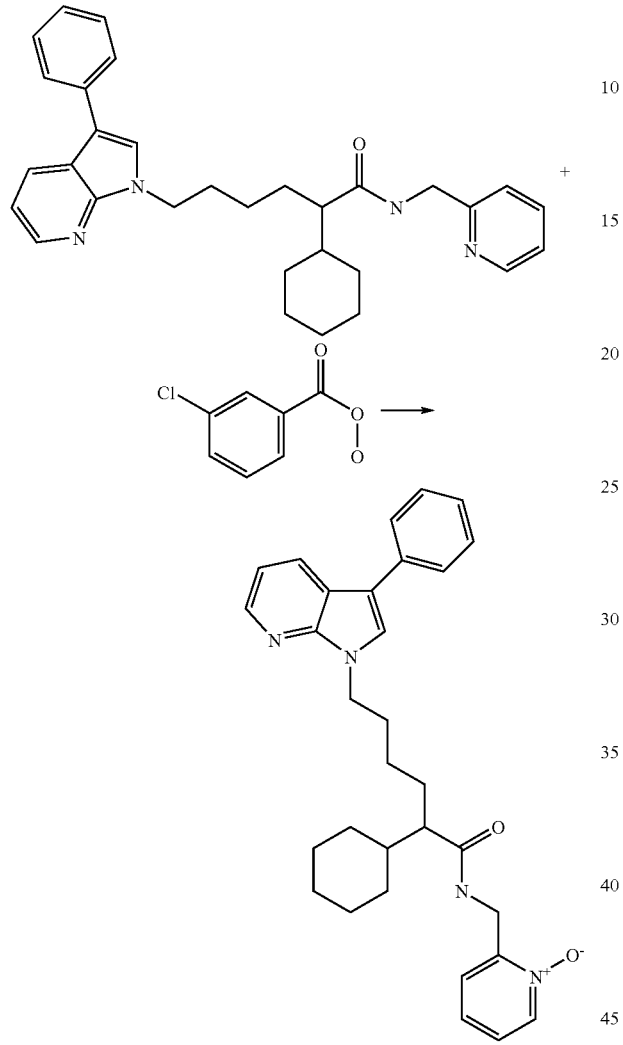

1.7 g (3.54 mmol) of amide are dissolved in 30 ml of THF and cooled to 0.5° C.

0.87 g (3054 mmol) of 3-chloroperbenzoic acid are then added at this temperature and stirring is continued at 0.5° C. for 1 hour and then overnight at room temperature.

The reaction mixture is diluted in CH$_2$Cl$_2$ and washed successively with Na$_2$SO$_3$ solution, with distilled water and finally with NaHCO$_3$ solution.

The organic phases are then dried with Na$_2$SO$_4$ and the product is evaporated to dryness.

After flash chromatography on silica gel, eluting with 1/1 EtOAc/CH$_2$Cl$_2$ and then 95/5 CH$_2$Cl$_2$/MeOH, 1.07 g of N-oxide are obtained in the form of crystals.

1H NMR: (DMSO-d6): 0.80-2.20 (18H, m); 4.15-4.40 (4H, m); 7.18-7.45 (5H, m); 7.46-7.59 (2H, m); 7.70-7.85 (2H, m); 8.02 (1H, s); 8.29-8.50 (4H, m).

Example 10

The azaindoles (A) can be prepared according to the following method:

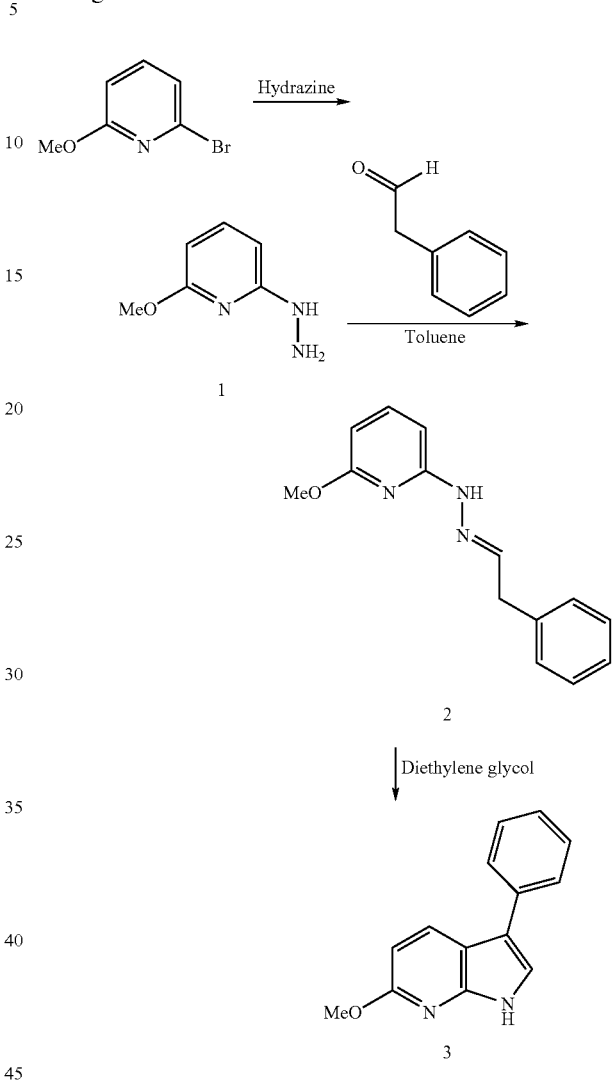

Synthesis of the hydrazine 1: 79 g of hydrazine monohydrate (1.58 mol) are added dropwise and with vigorous stirring to 30.6 g of 2-bromo-6-methoxypyridine (0.163 mol) in a 250 ml round-bottomed flask. After refluxing for 5 hours, the excess hydrazine is evaporated off. The medium is partitioned between 20 ml of water and 50 ml of ethyl acetate, and then re-extracted with ethyl acetate. After washing the organic phases with NaHCO$_3$, drying over Na$_2$SO$_4$ and concentrating, the oil obtained is distilled under vacuum. 11.6 g of a yellow oil are obtained (b.p.=70-85° C. at 0.5 mbar).

1H NMR (300 MHz, CDCl$_3$) 3.7 (s, 2H) 3.8 (s, 3H) 5.8 (s, 1H) 6.1 (d, J=7.8 Hz, 1H) 6.2 (d, J=7.8 Hz, 1H) 7.4 (t, J=7.9 Hz, 1H)

Synthesis of the hydrazide 2: 10.5 g of phenylacetaldehyde (87 mmol) are added to a solution of 11.6 g of hydrazine 1 (83 mmol) in 83 ml of toluene, in a 250 ml round-bottomed flask equipped with Dean-Stark apparatus. After removing the theoretical volume of water, the medium is concentrated and purified by chromatography on silica (eluting with CH$_2$Cl$_2$). 12.5 g of product are obtained.

1H NMR (300 MHz, CDCl$_3$) 3.6 (d, J=5.7 Hz, 2H) 3.8 (s, 3H) 6.1 (d, J=7.4 Hz, 1H) 6.7 (d, J=8.0 Hz, 1H) 7.1 (t, J=5.4 Hz, 1H) 7.2 (m, 5H) 7.4 (t, J=8.0 Hz, 1H) 7.7 (s, 1H)

Synthesis of the azaindole 3: 12.4 g of hydrazide 2 (51 mmol) dissolved in 50 ml of diethylene glycol are refluxed for 1 hour in a 250 ml round-bottomed flask fitted with a Vigreux column. After cooling to about 90° C., 250 ml of ice are added. The precipitate is filtered off by suction and recrystallised from 60 ml of ethanol. 3.5 g of azaindole 3 are obtained.

1H NMR (300 MHz, CDCl$_3$) 4.0 (s, 3H) 6.7 (d, J=8.6 Hz, 1H) 7.3 (m, 2H) 7.5 (m, 2H) 7.6 (m, 2H) 8.1 (d, J=8.6 Hz, 1H) 8.7 (s, 1H)

Alternative azaindoles may be chosen from:

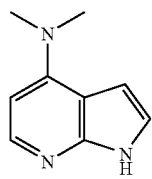

4

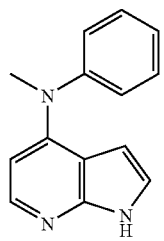

5

-continued

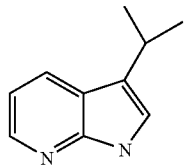

6

The 4-dimethylamino-7-azaindole 4 and 4-(N-methylanilino)-7-azaindole 5 were prepared according to the procedure described by N. Girgis et al. in *J. Heterocyclic Chem.*, 1989, 26, 317-325.

Compound 6 can be prepared according to the method described in Can. J. Chem., 1966, 44, 2455-2457. The product obtained presents the following data:

1H NMR (300 MHz, chloroform-d) 1.4 (m, 1.6 Hz, 6H) 3.2 (m, 1H) 7.1 (m, 1H) 7.1 (s, 1H) 8.0 (m, 1H) 8.3 (dd, J=3.2, 1.5 Hz, 1H) 10.4 (s, 1H).

The derivatives obtained containing an ester or acid function on R2 can be modified according to the desired final function on R2.

The following scheme illustrates, in a non-limiting manner, possible modifications on the representative example of the acid derivative for which X=Ph, Y=H, C$_6$ chain, R3=(rac) cycloheptyl, R4=H:

Scheme: route A + EDCl and modification of R2

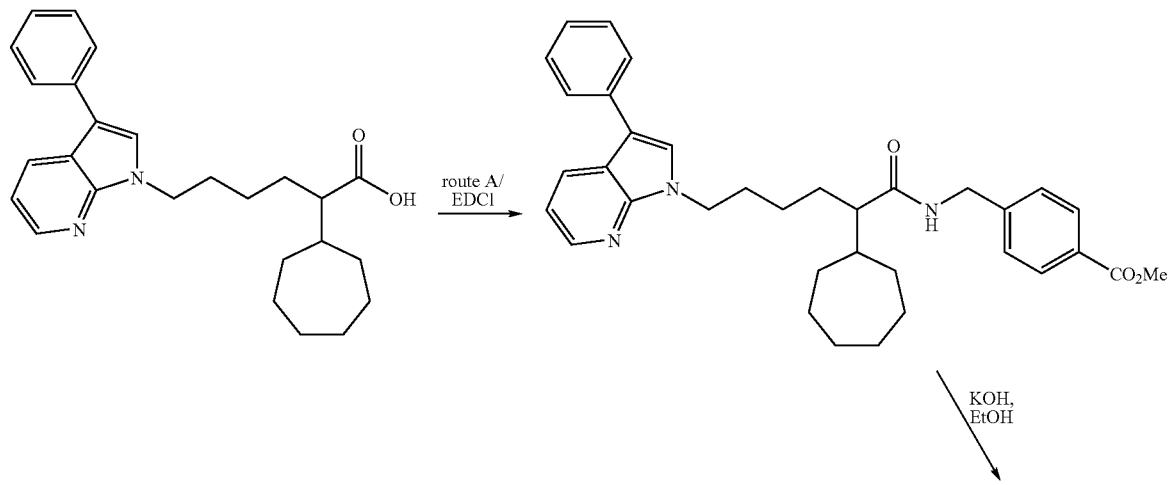

-continued
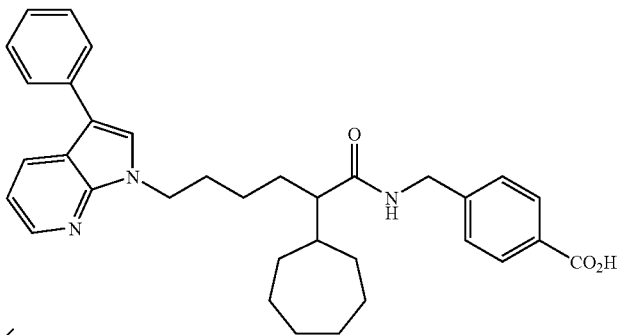
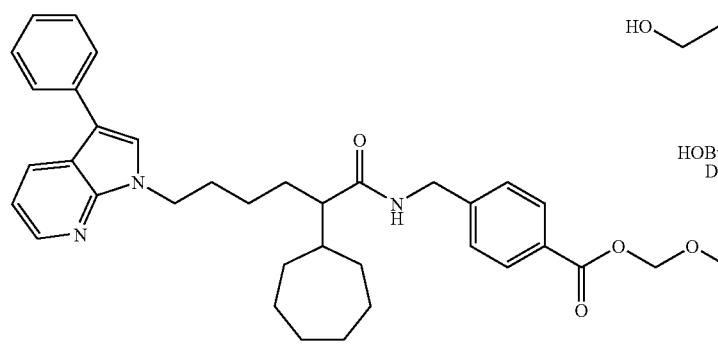
EXAMPLE 11
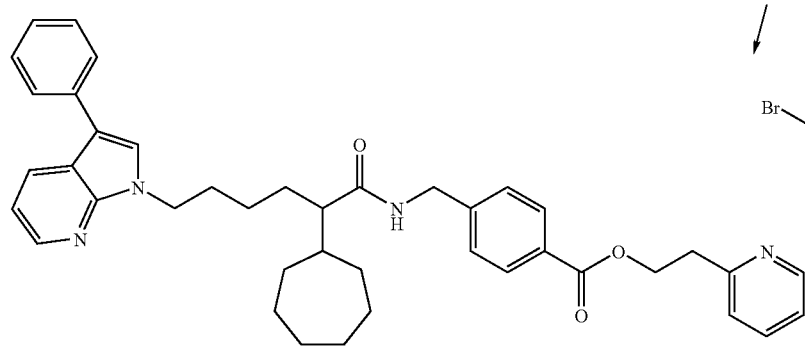
EXAMPLE 13

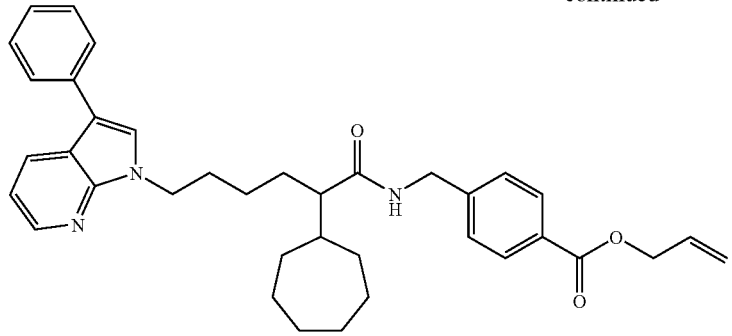

EXAMPLE 12

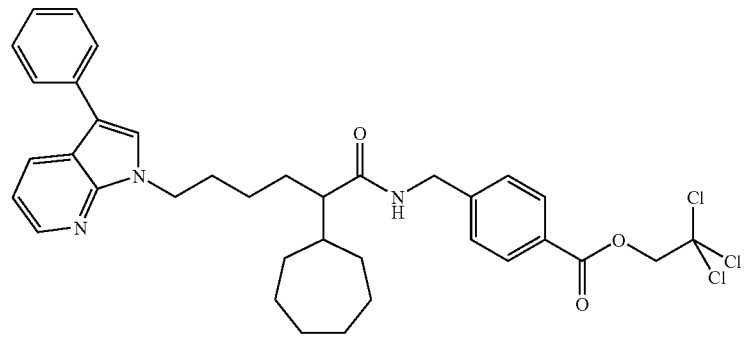

EXAMPLE 14

Example 11

A mixture of 134 mg (0.25 mmol) of acid in 40 ml of DCM and 42 µl (0.3 mmol) of triethylamine is cooled on a bath of ice-cold water. 23 µl (0.3 mmol) of chloro derivative are added thereto. The mixture is allowed to warm to room temperature and is stirred for 20 hours. After washing with water, drying ($Na_2SO_4$) and evaporating, a pasty oil is obtained, which is purified by chromatography ($SiO_2$, 1/1 EtOAc/heptane) to give 101 mg (69%) of an oil that crystallises.

Example 12

43.7 µl (0.5 mmol) of allyl bromide are added at room temperature to a mixture of 134 mg (0.25 mmol) of acid in 15 ml of DMF and 69 mg (0.5 mmol) of $K_2CO_3$. The mixture is stirred at room temperature for 20 hours and is then evaporated to dryness. The residue is taken up in DCM and washed with water. After drying ($Na_2SO_4$) and evaporating, a pasty oil is obtained, which is purified by chromatography ($SiO_2$, 2/3 EtOAc/heptane) to give 133 mg (92%) of a pasty oil.

Example 13

A mixture of 107.5 mg (0.2 mmol) of acid, 45.8 mg (0.22 mmol) of DCC and 6.9 mg (0.05 mmol) of HOBt in 50 ml of DCM is cooled in a bath of ice-cold water. 75.4 mg (0.6 mmol) of the required alcohol are added thereto. The mixture is allowed to warm to room temperature and is stirred for 20 hours. After washing with water, drying ($Na_2SO_4$) and evaporating, a pasty product is obtained, which is purified by chromatography ($SiO_2$, 1/1 EtOAc/heptane) to give 60 mg (46%) of a pasty product.

Example 14

A solution of 38 mg (0.25 mmol) of the required alcohol is added at room temperature to a mixture of 134 mg (0.25 mmol) of acid in 30 ml of DCM, 30.8 mg (0.25 mmol) of DMAP and 49 mg (0.25 mmol) of EDCl. The mixture is stirred for 20 hours at room temperature and is then evaporated to dryness. A pasty oil is obtained, which is purified by chromatography ($SiO_2$, 2/3 EtOAc/heptane) to give 127 mg (76%) of a pasty product.

Example 15

Analysis of the Inhibition of MTP Activity

The inhibition of the activity of microsomal triglyceride transfer protein (MTP) was tested by using the following operating protocol.

The inhibition of MTP activity with a compound can be quantified by observing the inhibition of the transfer of a labelled triglyceride, from a donor particle to an acceptor particle, in the presence of MTP. The procedure for the preparation of MTP is based on the method by Wetterau and Zilversmit (*Biochem. Biophys. Acta* (1986) 875, 610). A few grams of golden hamster liver are taken and then rinsed several times in a 250 mM sucrose solution at 0° C. All the following steps proceed at +4° C. A homogenate at a concentration of 50% in 250 mM sucrose is prepared using a Teflon mill and then centrifuged for 10 minutes at 10 000×g at +4° C. The supernatant is then centrifuged at 105 000×g for 75 minutes at +4° C. The supernatant is discarded and the microsomal pellet is taken up in 3 ml (per g of starting liver)

of Tris/HCl 150 mM pH 8.0. 1-ml aliquot fractions are stored at −80° C. until the time of use.

After thawing a fraction of microsomes (1 ml), 12 ml of refrigerated Tris/HCl 50 mM, KCl 50 mM, $MgCl_2$ 5 mM pH 7.4 buffers and 1.2 ml of deoxycholate (0.54% in water) are added. After incubation for 30 minutes at +4° C. with gentle agitation, the suspension is centrifuged at 105 00×g for 75 minutes. The supernatant comprising the soluble MTP is dialysed against Tris/HCl 150 mM, NaCl 40 mM, EDTA 1 mM, 0.02% sodium azide pH 7.4 buffer (5 times one litre over 2-3 days). The MTP is stored at +4° C., is stable for at least 30 days and is used in unmodified form in the test.

The donor particles (liposomes) are prepared from 208 µl of L-phosphatidylcholine at a concentration of 10 mg/ml in chloroform, and, 480 µl of [3H]-triolein at a concentration of 0.5 mCi/ml in toluene. After stirring, the solution is evaporated under nitrogen, taken up in 6 ml of Tris/HCl 50 mM, KCl 50 mM, $MgCl_2$ 5 mM pH. 7.4 buffer and incubated in an ultrasound bath for 30 minutes at room temperature. The liposomes are stored at +4° C. and sonicated again for 10 minutes before each use.

The acceptor particles are biotinylated low density lipoproteins (LDL-biot). These particles are supplied by the company Amersham.

The reaction mixture is prepared in untreated ½ well white plates (Corning Costar) by addition, in the following order, of: 5 µl of HEPES 50 mM, NaCl 150 mM, BSA 0.1% (w/v), 0.05% sodium azide (w/v), pH 7.4 buffer; 5 µl of liposomes; 5 µl of LDL-biot; 5 µl of test products in DMSO; 5 µl of MTP. After incubation for 18-24 hours at 37° C., the reaction is stopped adding 100 µl of Amersham SPA (Scintillation Proximity Assay) beads coupled to streptavidin, and the radioactivity is counted using a Top Count (Packard) machine at least one hour later. The inhibition of the transfer of the triglycerides with a compound is reflected by a reduction in the transferred radioactivity. The percentage of inhibition for a given compound is determined relative to controls that do not comprise compounds in the reaction mixture.

The results are expressed in terms of the $IC_{50}$, i.e. the concentration that allows a 50% inhibition of MTP. These results are summarised in Table 5 below for a number of representative compounds of the invention.

Example 16

Analysis of the Inhibition of ApoB Secretion

The activity of a compound according to the invention can be evaluated by measuring the inhibition of apo B secretion in HepG2 cells.

The HepG2 cells (ECACC No. 85011430) are used as model in the study of the in vitro hepatic secretion of lipoproteins (Dixon J. and Ginsberg H., *J. Lipid. Res.*, 1993, 34, 167-179).

The HepG2 cells are cultured in Dulbecco's modified Eagle's medium comprising 10% foetal calf serum (DMEM and FBS-Gibco) in 96-well plates under an atmosphere of 5% carbon dioxide for 24 hours (about 70% confluence).

The test compounds are dissolved at a concentration of 2 or 10 mM in dimethyl sulfoxide (DMSO). Serial dilutions (1:3.16) are made in DMSO and are added (1:200—Robot Multimek Beckman) to the growth medium (200 µL) and then finally incubated for 24 hours in the various wells containing the HepG2 cells.

The 24-hour culture supernatant diluted to 1:5 (phosphate-buffered saline: PBS comprising 1% bovine serum albumin) is tested according to a sandwich-ELISA method specific for human apo B.

The results are expressed in terms of $IC_{50}$, i.e. the concentration that produces a 50% inhibition of apo B secretion in the HepG2 cells.

These results are collated in Table 5 below for a number of representative compounds of the invention.

TABLE 5

| CHEMISTRY | IC50 MTP (nM) | IC50apo B (nM) |
|---|---|---|
| (structure) | 529 | 3 |

TABLE 5-continued

| CHEMISTRY | IC50 MTP (nM) | IC50apo B (nM) |
|---|---|---|
| (structure) | 175 | 15 |
| (structure) | 381 | 18 |

The invention claimed is:

1. A 7-azaindole-based compound of formula (I)

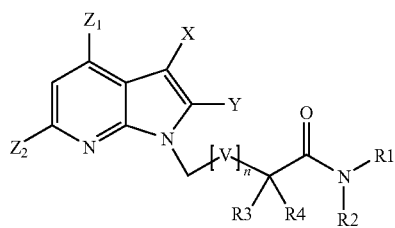

in which

V is —CH$_2$—;

n denotes the number of —CH$_2$— radicals, and is 3 or 4;

Z1 represents a hydrogen atom;

Z2 represents a hydrogen atom;

X is phenyl or substituted phenyl;

Y represents a hydrogen atom;

R1 is CH$_2$Ar or CH$_2$-heteroaryl;

R2 represents a hydrogen atom;

R3 is cyclopentyl, cyclohexyl or cycloheptyl; and

R4 represents a hydrogen atom;

or a salt, N-oxide, stereoisomer or a mixture of stereoisomers thereof.

2. A compound according to claim 1, in which

X is phenyl or substituted phenyl, substituted by OH, Pyridyl (2-, 3- or 4-), or Br;

and

R1 is CH$_2$Ar, wherein Ar is a substituted or unsubstituted phenyl, or CH$_2$-heteroaryl, wherein heteroaryl is pyridyl, pyrimidine, or pyridine-N-oxide.

3. A compound according to claim 2, in which

R1 is CH$_2$Ar, wherein Ar is an unsubstituted phenyl, or CH$_2$-heteroaryl, wherein heteroaryl is pyridyl, pyrimidine, or pyridine-N-oxide.

4. A compound, which is

N-(4-methylsulfonyl)phenylmethyl-2-cyclohexyl-6-(3-phenyl-7-azaindol-1-yl)hexanamide N-benzyl-2-cyclopentyl-7-(3-phenyl-7-azaindol-1-yl) hexanamide N-(4-pyridylmethyl)-2-cycloheptyl-6-(3-phenyl-7-azaindol-1-yl)heptanamide N-(4-pyridylmethyl)-2-cyclohexyl-6-(3-phenyl-7-azaindol-1-yl)heptanamide N-(4-pyridylmethyl)-2-cyclohexyl-6-(3-phenyl-7-azaindol-1-yl)hexanamide N-(4-methoxycarbonyl)phenyl-2-cycloheptyl-6-(3-phenyl-7-azaindol-1-yl)-hexanamide N-(4-methylsulfonyl)phenylmethyl-2-cycloheptyl-6-(3-phenyl-7-azaindol-1-yl)heptanamide N-(4-n-butyl)phenylmethyl-2-cycloheptyl-6-(3-phenyl-7-azaindol-1-yl)-heptanamide N-(4-methylsulfonyl)phenylmethyl-2-cyclopentyl-6-(3-phenyl-7-azaindol-1-yl)heptanamide N-(2-pyridylmethyl)-2-cyclohexyl-6-(3-phenyl-7-azaindol-1-yl)heptanamide N-(2-pyridylmethyl)-2-cycloheptyl-6-(3-phenyl-7-azaindol-1-yl)heptanamide N-(2-pyridylmethyl)-2-cyclohexyl-6-(3-phenyl-7-azaindol-1-yl)hexanamide N-benzyl-2-cyclohexyl-6-(3-phenyl-7-azaindol-1-yl)hexanamide N-benzyl-2-cycloheptyl-6-(3-phenyl-7-azaindol-1-yl)
hexanamide
N-(4-pyridylmethyl)-2-cycloheptyl-6-(3-phenyl-7-azain-
dol-1-yl)hexanamide (EMD=480030)
N-(4-methylsulfonyl)phenylmethyl-2-cyclopentyl-6-(3-
phenyl-7-azaindol-1-yl)hexanamide
N-(4-aminosulfonyl)phenylmethyl-2-cyclopentyl-6-(3-
phenyl-7-azaindol-1-yl)hexanamide
N-(4-pyridylmethyl)-2-cyclopentyl-6-(3-phenyl-7-azain-
dol-1-yl)heptanamide
N-(2-pyridylmethyl)-2-cyclopentyl-6-(3-phenyl-7-azain-
dol-1-yl)heptanamide
N-(4-methoxycarbonyl)phenyl-2-cyclopentyl-6-(3-phe-
nyl-7-azaindol-1-yl)-hexanamide
N-(2-pyridylmethyl)-2-cyclohexyl-6-(3-pyridyl-7-azain-
dol-1-yl)hexanamide
N-(2-fluoro)phenylmethyl-2-cycloheptyl-6-(3-phenyl-7-
azaindol-1-yl)hexan-amide
N-(1-phenylethyl)-2-cycloheptyl-6-(3-phenyl-7-azaindol-
1-yl)hexanamide
N-(6-fluoroquinol-2-ylmethylpiperidino)-2-cyclopentyl-
6-(3-phenyl-7-azaindol-1-yl)hexanamide
N-(2-pyridyl)-2-cycloheptyl-6-(3-phenyl-7-azaindol-1-
yl)hexanamide
N-benzyl-2-cyclopentyl-6-(3-phenyl-7-azaindol-1-yl)
hexanamide
N-(4-pyridyl)-2-cyclopentyl-6-(3-phenyl-7-azaindol-1-
yl)hexanamide
N-(4-methylsulfonyl)phenylmethyl-2-(2,3-cyclopente-
nyl)-6-(3-phenyl-7-azaindol-1-yl)hexanamide
N-(2-pyridylmethyl)-2-cyclohexyl-6-(3-phenyl-7-azain-
dol-1-yl)hexanamide (one enantiomer)
N-(2-pyridylmethyl)-2-cyclohexyl-6-(3-phenyl-7-azain-
dol-1-yl)hexanamide (the enantiomer of the above com-
pound)
N-(2-pyridyl)-2-cyclopentyl-6-[3-(pyrid-3-yl)-7-azain-
dol-1-yl)heptanamide
N-(2-pyridyl)-2-cyclopentyl-6-[3-(pyrid-4-yl)-7-azain-
dol-1-yl)heptanamide
N-(2-hydroxy-1-phenyl)ethyl-2-cycloheptyl-6-(3-phenyl-
7-azaindol-1-yl)-hexanamide
N-(4-fluorophenyl)methyl-2-cycloheptyl-6-(3-phenyl-7-
azaindol-1-yl)hexan-amide
N-(2'-pyridino)methyl-2-cyclohexyl-6-(3-phenyl-6-meth-
oxy-7-azaindol-1-yl)hexanamide or
N-(4'-pyridino)methyl-2-cyclohexyl-6-(3-phenyl-6-meth-
oxy-7-azaindol-1-yl)hexanamide or a salt, N-oxide, stereoisomer or a mixture of stereoisomers thereof.

5. A pharmaceutical composition comprising a compound according to claim 1 and at least one pharmaceutically acceptable vehicle.

6. A method for inhibiting and of ApoB secretion, comprising administering to a subject in need thereof an effective amount of a compound of claim 1.

7. A pharmaceutical composition comprising a compound according to claim 4 and at least one pharmaceutically acceptable vehicle.

8. A compound according to claim 4 or a pharmaceutically acceptable salt thereof.

9. A method for inhibiting MTP and of ApoB secretion, comprising administering to a subject in need thereof an effective amount of a compound of claim 8.

10. A pharmaceutical composition comprising a compound according to claim 8 and at least one pharmaceutically acceptable vehicle.

11. A compound according to claim 1 or a pharmaceutically acceptable salt thereof.

12. A compound according to claim 1 or a N-oxide thereof.

13. A compound according to claim 4 or a N-oxide thereof.

14. A pharmaceutical composition comprising a compound according to claim 11 and at least one pharmaceutically acceptable vehicle.

15. A method for inhibiting MTP and of ApoB secretion, comprising administering to a subject in need thereof an effective amount of a compound of claim 11.

* * * * *

UNITED STATES PATENT AND TRADEMARK OFFICE
CERTIFICATE OF CORRECTION

| | | |
|---|---|---|
| PATENT NO. | : 7,838,533 B2 | Page 1 of 1 |
| APPLICATION NO. | : 11/658596 | |
| DATED | : November 23, 2010 | |
| INVENTOR(S) | : Guevel et al. | |

It is certified that error appears in the above-identified patent and that said Letters Patent is hereby corrected as shown below:

Column 94, line 14 reads "A method for inhibiting and of ApoB secretion, com-" should read
-- A method for inhibiting MTP and of ApoB secretion, com- --

Signed and Sealed this
Eighteenth Day of January, 2011

David J. Kappos
*Director of the United States Patent and Trademark Office*